United States Patent
Brown et al.

(10) Patent No.: US 6,432,949 B1
(45) Date of Patent: Aug. 13, 2002

(54) AMIDE DERIVATIVES USEFUL AS INHIBITORS OF THE PRODUCTION OF CYTOKINES

(75) Inventors: Dearg S Brown; George R Brown, both of Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/762,107

(22) PCT Filed: Jul. 29, 1999

(86) PCT No.: PCT/GB99/02489

§ 371 (c)(1),
(2), (4) Date: Feb. 2, 2001

(87) PCT Pub. No.: WO00/07991

PCT Pub. Date: Feb. 17, 2000

(30) Foreign Application Priority Data

Aug. 4, 1998 (GB) .............................................. 9816838
Nov. 13, 1998 (GB) .............................................. 9824939

(51) Int. Cl.[7] ...................... C07D 413/12; C07C 233/00; A61K 31/44; A61K 31/47; A61P 43/00

(52) U.S. Cl. ......................... 514/232.2; 544/82; 544/86; 544/121; 544/131; 544/283; 544/353; 546/316; 546/323; 546/309; 546/194; 546/122; 546/169

(58) Field of Search ........................... 544/131, 82, 386; 514/235.5; 546/316

(56) References Cited

U.S. PATENT DOCUMENTS

| | | |
|---|---|---|
| 1,903,899 A | 4/1933 | Laska et al. |
| 1,909,960 A | 5/1933 | Hitch |
| 4,749,729 A | 6/1988 | Kohli et al. |

FOREIGN PATENT DOCUMENTS

| | | |
|---|---|---|
| DE | 28 12 252 | 10/1979 |
| EP | 0 849 256 A1 | 6/1998 |
| WO | WO 93/04170 | 3/1993 |
| WO | WO 97/05878 | 2/1997 |
| WO | WO 97/32853 | 9/1997 |
| WO | WO 98/06715 | 2/1998 |
| WO | WO 98/22103 | 5/1998 |
| WO | WO 99/15164 | 4/1999 |
| WO | WO 99/59959 | 11/1999 |
| WO | WO 99/59960 | 11/1999 |
| WO | WO 00/07980 | 2/2000 |
| WO | WO 00/7991 | 2/2000 |
| WO | WO 00/18738 | 4/2000 |
| WO | WO 00/20402 | 4/2000 |
| WO | WO 00/55120 | 9/2000 |
| WO | WO 00/55153 | 9/2000 |
| WO | WO 00/56738 | 9/2000 |
| WO | WO 99/56738 | 9/2000 |
| WO | WO 01/27089 | 4/2001 |

OTHER PUBLICATIONS

Ando et al., Magn. Reson.Chem. 639–45, 1995, Chemical Abstract: 123: 227514, 1995.
Ando et al., "Producing azo lake pigments"; Chemical Abstract, vol. 106, Abstract No., 215574, 1986.
Adams et al., "Search for trypanocides. III. Analogs of suramin.", Chemical Abstracts, vol. 51, 1957, col. 5068 and 5069.
Hanson, "Review—Pulmonary–Allergy, Dematological, Gastrointestinal & Arthritis—Inhibitors of p38 kinase", Exp. Opin. Ther. Patents, 1997, XP–002086152, pp. 729–733 1997.
Ito et al., Photosensitive material containing microencapsulated hydrazine derivatives; Chemical Abstract, vol. 118, Abstract No. 70021, 1992.
Makoto; "Amide and Its Use"; Patent Abstracts of Japan, Abstract No. 09124571, May 13, 1997, also attached: Abstract (Derwent); XP 002086154.
Sugawara et al., Kogyo Kagaku Zasshi 72(11) 2425–2429, 1969, Chemical Abstract; 72:66514, 1970.
Wang et al., "Low–valent Titanium–induced Reactions of Substituted Nitrobenzenes", J. Chem. Research, 1998, pp. 182–183.
Ashton, Michael J. Et Al: "New Low–Density Lipoprotein Receptor Upregulators Acting Via a Novel Mechanism" J. Med. Chem. (1996), 39(17), 3343–3356,XP002054111 cited in the application, compounds 6h, 6k, 6l, 6m.
Muehhlebach, Andreas: "Pyrazoles–a novel class of blocking agents for isocyanates" J. Polym. Sci., Part A: Polym, Chem. (1994), 32(4), 753–65, XP000424276 compounds 15, 16.
Chemical Abstract, vol. 76, No. 21, May 22, 1972 Columbus, Ohio, US; abstract No. 126704v, Lesiak, Tadeusz: "New amides of pyrrole–N–and indole–N–carboxylic acids" p. 471; XP002121335, compounds III abstract & Rocz. Chem. (1971), 45(10), 1755–9.

Primary Examiner—Robert W. Ramsuer
Assistant Examiner—Andrea D. Small
(74) Attorney, Agent, or Firm—Morgan, Lewis & Bockius LLP

(57) ABSTRACT

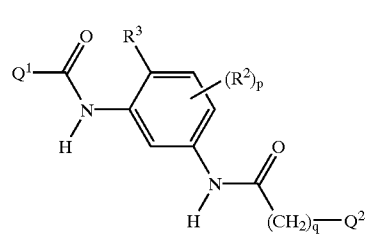

(I)

The invention concerns amide derivatives of formula (I) wherein $R^3$ is (1–6C)alkyl or halogeno; $Q^1$ is heteroaryl which is optionally substituted with 1, 2, 3, or 4 substituents such as hydroxy, halogeno, trifluoromethyl, (1–6C)alkyl, (1–6C)alkoxy, hydroxy-(1–6C)alkyl, (1–6C)alkoxy-(1–6C)alkyl, hydroxy-(2–6C)alkoxy, amino-(2–6C)alkylamino, N-(1–6C)alkyl-(1–6C)alkylamino-(2–6C)alkylamino, aryl, heteroaryl and heterocyclyl; p is 0–2 and $R^2$ is a substituent such as hydroxy and halogeno; q is 0–4; and $Q^2$ includes optionally substituted aryl, cycloalkyl, heteroaryl and heterocyclyl; or pharmaceutically-acceptable salts or in vivo-cleavable esters thereof; processes for their preparation, pharmaceutical compositions containing them and their use in the treatment of diseases or medical conditions mediated by cytokines.

11 Claims, No Drawings

AMIDE DERIVATIVES USEFUL AS INHIBITORS OF THE PRODUCTION OF CYTOKINES

This application is a 371 of PCT/GB99/02489 Jul. 29, 1999.

This invention concerns certain amide derivatives which are useful as inhibitors of cytokine mediated disease. The invention also concerns processes for the manufacture of the amide derivatives of the invention, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis and adult respiratory distress syndrome), and in the production and development of various cardiovascular and cerebrovascular disorders such as congestive heart failure, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet*, 1994, 344 1125 and *British Journal of Rheumatology*, 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFA and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G J Hanson in *Expert Opinions on Therapeutic Patents*, 1997, 7, 729–733. p38 kinase is known to exist in isoforms identified as p38α and p38β.

It is known from *J. Med. Chem.*, 1996, 39, 3343–3356, that certain benzanilide derivatives can upregulate the expression of the low density lipoprotein (LDL) receptor in human hepatocyte cells. The disclosed compounds included two pyridinecarboxamide derivatives, namely N-[5-(3-cyclohexylpropionamido)-2-methylphenyl]pyridine-3-carboxamide and N-[5-(3-cyclohexylpropionamido)-2-methylphenyl]pyridine-4-carboxamide.

The compounds disclosed in the present invention are inhibitors of the production of cytokines such as TNF, in particular of TNFα, and various interleukins, in particular IL-1.

According to one aspect of the present invention there is provided an amide derivative of the Formula I

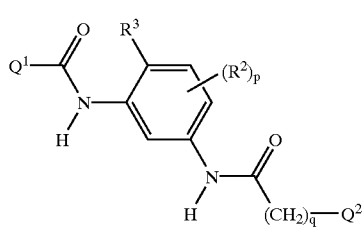

wherein

R³ is (1–6C)alkyl or halogeno;

Q¹ is heteroaryl which is optionally substituted with 1, 2, 3 or 4 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N1–6C)alkyl-N-(1–6C)alkylcarbamoyl1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl1–6C)alkylamino(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1 6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-( 1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C)alkanoylamino, and wherein any of the substituents on Q¹ defined hereinbefore which comprise a CH₂ group which is attached to 2 carbon atoms or a CH₃ group which is attached to a carbon atom may optionally bear on each said CH₂ or CH₃ group a substituent selected from hydroxy, amino, (1–6C)alkoxy, (1–6C)alkylamino, di-[(1–6C)alkyl]amino and heterocyclyl;

and wherein any aryl, heteroaryl or heterocyclyl group in a substituent on Q¹ may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

R² is hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alkylamino or di-[(1–6C)alkyl]amino;

p is 0, 1 or 2;

q is 0, 1, 2,3 or 4; and

Q² is aryl, aryl-(1–6C)alkoxy, aryloxy, arylamino, N-(1–6C)alkyl-arylamino, aryl-(1–6C)alkylamino, N-(1–6C)alkyl-aryl1–6C)alkylamino, aroylamino, arylsulphonylamino, N-arylsulphamoyl, aryl-(2–6C)alkanoylamino, cycloalkyl, heteroaryl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl or heterocyclyl-(2–6C)alkanoylamino and Q² is optionally substituted with 1, 2, 3 or 4 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(-6C)alkyl]amino-(2–6C)alkoxy, halogenlo-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(-6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkyamino(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-( 2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C)alkanoylamino, and wherein any of the substituents on $Q^2$ defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl;

and wherein any aryl, heteroaryl or heterocyclyl group in a substituent on $Q^2$ may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

or a pharmaceutically-acceptable salt or in-vivo-cleavable ester thereof;

except that N-[5-(3-cyclohexylpropionamido)2-methylphenyl]pyridine-3-carboxamide and N-[5-(3-cyclohexylpropionamido)-2-methylphenyl]pyridine4-carboxamide are excluded.

According to a further aspect of the invention there is provided a compound of the Formula I
wherein
$R^3$ is (1–6C)alkyl or halogeno;
$Q^1$ is heteroaryl which is optionally substituted with 1, 2, 3 or 4 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(-6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)ally-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C)alkanoylamino, and wherein any aryl, heteroaryl or heterocyclyl group in a substituent on $Q^1$ may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N-di-[(1–6C)alkyl]carbamoyl, (2–6C)alkanoyl, amino, (1–6C)alkylamino and di-[(1–6C)alkyl]amino;

$R^2$ is hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alkylamino or di-[(1–6C)alkyl]amino;

p is 0, 1 or 2;

q is 0, 1, 2, 3 or 4; and $Q^2$ is aryl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, cycloalkyl, heteroaryl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl or heterocyclyl-(2–6C)alkanoylamino and $Q^2$ is optionally substituted with 1, 2, 3 or 4 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy2–6C)alkylamino, N-(1–6C)alky-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(-6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)

alkanoylamino, heterocyclyl, heterocyclyl-(1–6C) alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C) alkanoylamino, and wherein any aryl, heteroaryl or heterocyclyl group in a substituent on $Q^2$ may optionally bear 1 or 2 substituents selected from hydroxy, halogeno, (1–6C)alkyl, (1–6C)alkoxy, carboxy, (1–6C) alkoxycarbonyl, N-(1–6C)alkylcarbamoyl, N,N-di-[(1–6C)alkyl]carbamoyl, (2–6C)alkanoyl, amino, (1–6C)alkylamino and di-[(1–6C)alkyl]amino;

or a pharmaceutically-acceptable salt or in-vivo-cleavable ester thereof

In this specification the generic term "alkyl" includes both straight-chain and branched-chain alkyl groups. However references to individual alkyl groups such as "propyl" fare specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

A suitable value for $Q^2$ or for a substituent on $Q^1$ or $Q^2$ when it is aryl or for the aryl group within a $Q^2$ group or within a substituent on $Q^1$ or $Q^2$ is, for example, phenyl or naphthyl, preferably phenyl.

A suitable value for $Q^1$ or $Q^2$ or for a substituent on $Q^1$ or $Q^2$ when it is heteroaryl or for the heteroaryl group within a $Q^2$ group or within a substituent on $Q^1$ or $Q^2$ is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl, preferably furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl, more preferably thienyl, isoxazolyl, pyridyl, benzothiazolyl, quinolyl, quinazolinyl, quinoxalinyl or naphthyridinyl.

A suitable value for $Q^2$ or for a substituent on $Q^1$ or $Q^2$ when it is heterocyclyl or for the heterocyclyl group within a $Q^2$ group or within a substituent on $Q^1$ or $Q^2$ is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, pyrrolinyl, pyrrolidinyl, morpholinyl, piperidinyl, homopiperidinyl, piperazinyl, homopiperazinyl, dihydropyridinyl, tetrahydropyridinyl, dihydropyrimidinyl or tetrahydropyrimidinyl, preferably pyrrolidin-1-yl, pyrrolidin-2-yl, morpholino, piperidino, piperazin-1-yl or homopiperazin-1-yl.

Suitable values for various $R^3$ or $R^2$ groups, or for various substituents on $Q^1$ or $Q^2$ or on an aryl, heteroaryl, heterocyclyl or other group in a substituent on $Q^1$ or $Q^2$ includes:

for halogeno: fluoro, chloro, bromo and iodo;

for (1–6C)alkyl: methyl, ethyl, propyl, isopropyl and tert-butyl;

for (2–6C)alkenyl: vinyl and allyl;

for (2–6C)alkynyl: ethynyl and 2-propynyl;

for (1–6C)alkoxy: methoxy, ethoxy, propoxy, isopropoxy and butoxy;

for (1–6C)alkoxycarbonyl: methoxycarbonyl, ethoxycarbonyl, propoxycarbonyl and tert-butoxycarbonyl;

for N-(1–6C)alkylcarbamoyl: N-methylcarbamoyl, N-ethylcarbamoyl and N-propylcarbamoyl;

for N,N-di-[(1–6C)alkyl]carbamoyl: N,N-dimethylcarbamoyl, N-ethyl-N-methylcarbamoyl and N,N-diethylcarbamoyl;

for (2–6C)alkanoyl: acetyl and propionyl;

for (1–6C)alkylamino: methylamino, ethylamino and propylamino;

for di-[(1–6C)alkyl]amino: dimethylamino, diethylamino and N-ethyl-N-methylamino;

for halogeno-(1–6C)alkyl: fluoromethyl, chloromethyl, bromomethyl, difluoromethyl, dichloromethyl, dibromomethyl, 2-fluoroethyl, 2-chloroethyl and 2-bromoethyl;

for hydroxy-(1–6C)alkyl: hydroxymethyl, 2-hydroxyethyl, 1-hydroxyethyl and 3-hydroxypropyl;

for (1 4C)alkoxy-(1–6C)alkyl: methoxymethyl, ethoxymethyl, 1-methoxyethyl, 2-methoxyethyl, 2-ethoxyethyl and 3-methoxypropyl;

for cyano-(1–6C)alkyl: cyanomethyl, 2-cyanoethyl, 1-cyanoethyl and 3-cyanopropyl;

for amino-(1–6C)alkyl: aminomethyl, 2-aminoethyl, 1-aminoethyl and 3-aminopropyl;

for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;

for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl.

A suitable value for $Q^2$ when it is cycloalkyl is, for example, a non-aromatic mono- or bicyclic 4- to 10-membered carbon ring such as cyclobutyl, cyclopentyl, cyclohexyl, cycloheptyl, bicyclo[2.2.1]heptyl and bicyclo [4.4.0]decyl, preferably cyclobutyl, cyclopentyl, cyclohexyl or cycloheptyl, more preferably cyclohexyl.

Suitable values for $Q^2$ and suitable values for a substituent on $Q^1$ or $Q^2$ include:

for aryl-(1–6C)alkyl: benzyl, 2-phenylethyl, 2-phenylpropyl and 3-phenylpropyl;

for aryl-(1–6C)alkoxy: benzyloxy and 2-phenylethoxy;
for aryloxy: phenoxy and 2-naphthyloxy;
for arylamino: anilino;
for N-(1–6C)alkyl-arylamino: N-methylanilino and N-ethylanilino;
for aryl-(1–6C)alkylamino: benzylamino, 2-phenethylamino, 2-phenylpropylamino and 3-phenylpropylamino;
for N-(1–6C)alkyl-aryl-(1–6C)alkylamino: N-benzyl-N-methylamino;
for aroylamino: benzamido and 2-naphthoylamino; arylsulphonylamino: benzenesulphonylamido;
for N-arylsulphamoyl: N-phenylsulphamoyl;
for aryl-(2–6C)alkanoylamino: phenylacetamido and 3-phenylpropionamido;
for heteroaryl-(1–6C)alkyl: heteroarylmethyl, 2-heteroarylethyl, 2-heteroarylpropyl and 3-heteroarylpropyl;
for heteroaryl-(1–6C)alkoxy: heteroarylmethoxy and 2-heteroarylethoxy;
for N-(1–6C)alkyl-heteroarylamino: N-methylheteroarylamino;
for heteroaryl-(1–6C)alkylamino: heteroarylmethylamino, 2-heteroarylethylamino and 3-heteroarylpropylamino;
for N-(1–6C)alkyl-heteroaryl-(1–6C)alkylamino: N-methylheteroarylmethylamino and N-methyl-2-heteroarylethylamino;
for heteroaryl-(2–6C)alkanoylamino: heteroarylacetamido and 3-heteroarylpropionamido;
for heterocyclyl-(1–6C)alkyl: heterocyclylmethyl and 2-heterocyclylethyl;
for heterocyclyl-(1–6C)alkoxy: heterocyclylmethoxy and 2-heterocyclylethoxy;
for N-(1–6C)alkyl-heterocyclylamino: N-methylheterocyclylamino;
for heterocyclyl-(1–6C)alkylamino: heterocyclylmethylamino, 2-heterocyclylethylamino and 3-heterocyclylpropylamino;
for N-(1–6C)alkyl-heterocyclyl-(1–6C)alkylamino: N-methylheterocyclylmethylamino and N-methyl-2-heterocyclylethylamino;
for heterocyclyl-(2–6C)alkanoylamino: heterocyclylacetamido and 3-heterocyclylpropionamido;
for (1–3C)alkylenedioxy: methylenedioxy, ethylenedioxy and propylenedioxy;
for (1–6C)alkylthio: methylthio, ethylthio and propylthio;
for (1–6C)alkylsulphinyl: methylsulphinyl, ethylsulphinyl and propylsulphinyl;
for (1–6C)alkylsulphonyl: methylsulphonyl, ethylsulphonyl and propylsulphonyl;
for (2–6C)alkanoyloxy: acetoxy and propionyloxy:
for (1–6C)alkanoylamino: formamido, acetamido and propionamido;
for N-(1–6C)alkylsulphamoyl: N-methylsulphamoyl and N-ethylsulphamoyl;
for N,N-di-[(1–6C)alkyl]sulphamoyl: N,N-1dimethylsulphamoyl;
for (1–6C)alkanesulphonylamino: methanesulphonylamino and ethanesulphonylamino;
for N-(1–6C)alkyl-(1–6C)alkanesulphonylamino: N-methynethanesulphonylamino and N-methylethanesulphonylamino;

for carboxy-(1–6C)alkyl: carboxymethyl, 1-carboxyethyl, 2-carboxyethyl, 3-carboxypropyl and 4-carboxybutyl;
for (1–6C)alkoxycarbonyl-(1–6C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;
for carbamoyl-(1–6C)alkyl: carbamoylmethyl, 1-carbamoylethyl, 2-carbamoylethyl and 3-carbamoylpropyl;
for N-(1–6C)alkylcarbamoyl-(1–6C)alkyl: N-methylcarbamoylmethyl, N-ethylcarbamoylmethyl, N-propylcarbamoylmethyl, 1-(N-methylcarbamoyl)ethyl, 1-ethylcarbamoyl)ethyl, 2-(N-methylcarbamoyl)ethyl, 2-(N-ethylcarbamoyl)ethyl and 3-(N-methylcarbamoyl)propyl;
for N,N-di-[(1–6C)alkyl]carbamoyl-(1–6C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4-(N,N-dimethylcarbamoyl)butyl;
for halogeno-(2–6C)alkoxy: 2-chloroethoxy, 2-bromoethoxy and 3-chloropropoxy;
for hydroxy-(2–6C)alkoxy: 2-hydroxyethoxy, 2-hydroxy-1-methylethoxy, 3-hydroxypropoxy, 2-hydroxypropoxy and 4-hydroxybutoxy;
for (1–6C)alkoxy-(2–6C)alkoxy: 2-methoxyethoxy, 2-ethoxyethoxy, 3-methoxypropoxy, 2-methoxy-1-methylethoxy and 4-ethoxybutoxy;
for cyano-(1–6C)alkoxy: cyanomethoxy, 2-cyanoethoxy and 3-cyanopropoxy;
for carboxy-(1–6C)alkoxy: carboxymethoxy, 1-carboxyethoxy, 2-carboxyethoxy and 3-carboxypropoxy;
for (1–6C)alkoxycarbonyl-(1–6C)alkoxy: methoxycarbonylmethoxy, ethoxycarbonylmethoxy, tert-butoxycarbonylmethoxy, 2-methoxycarbonylethoxy and 3-ethoxycarbonylpropoxy;
for carbamoyl-(1–6C)alkoxy: carbamoylmethoxy and 2-carbarmoylethoxy;
for N-(1–6C)alkylcarbamoyl-(1–6C)alkoxy: N-methylcarbamoylmethoxy, 2-(-ethylcarbamoyl)ethoxy and 3-(N-methylcarbamoyl)propoxy;
for N,N-di-[(1–6C)alkyl]carbamoyl-(1–6C)alkoxy, N,N-dimethylcarbamoylmethoxy, 2-(N,N-dimethylcarbamoyl)ethoxy and 3-(N,N-diethylcarbamoyl)propoxy;
for amino-(2–6C)alkoxy: 2-aminoethoxy, 2-amino-1-methylethoxy, 3-aminopropoxy, 2-amino-2-methylpropoxy and 4-aminobutoxy;
for (1–6C)alkylamino-(2–6C)alkoxy: 2-methylaminoethoxy, 2-methylamino-1-methylethoxy and 3-ethylaminopropoxy;
for di-[(1–6C)alkyl]amino-(2–6C)alkoxy: 2-dimethylaminoethoxy, 2-diethylaminoethoxy, 2-dimethylaminopropoxy, 2-dimethylamino-2-methylpropoxy, 3-dimethylaminopropoxy and 4-dimethylaminobutoxy;
for halogeno-(2–6C)alkylamino: 2-fluoroethylamino, 2-chloroethylamino, 2-bromoethylamino, 3-fluoropropylamino and 3-chloropropylamino;

for hydroxy-(2–6C)alkylamino: 2-hydroxyethylamino, 3-hydroxypropylamino, 2-hydroxy-2-methylpropylamino and 4-hydroxybutylamino;

for (1–6C)alkoxy-(2–6C)alkylamino: 2-methoxyethylamino, 2-ethoxyethylamino, 3-methoxypropylamino and 3-ethoxypropylamino;

for cyano-(1–6C)alkylamino: cyanomethylamino, 2-cyanoethylamino and 3-cyanopropylamino;

for carboxy-(1–6C)alkylamino: carboxymethylamino, 1-carboxyethylamino, 2-carboxyethylamino and 3-carboxypropylamino;

for (1–6C)alkoxycarbonyl-(1–6C)alkylamino: methoxycarbonylmethylamino, 2-(ethoxycarbonyl)ethylamino and 3-(tert-butoxycarbonyl)propylamino;

for carbamoyl-(1–6C)alkylamino: carbamoylmethylamino and 2-carbamoylethylamino;

for N-(1–6C)alkylcarbamoyl-(1–6C)alkylamino: N-methylcarbamoylmethylamino, N-ethylcarbamoylmethylamino and 2-(N-methylcarbamoyl)ethylamino;

for N,N-di-[(1–6C)alkyl]carbamoyl-(1–6C)alkylamino: N,) N-dimethylcarbamoyl-methylamino, N,N-diethylcarbamoylmethylamino and 2-(N,N-dimethylcarbamoyl)ethylamino;

for amino-(2–6C)alkylamino: 2-aminoethylamino, 3-aminopropylamino, 2-amino-2-methylpropylamino and 4-aminobutylamino;

for (1–6C)alkylamino-(2–6C)alkylamino: 2-methylaminoethylamino, 2-ethylaminoethylamino, 2-propylaminoethylamino, 3-methylaminopropylamino, 3-ethylaminopropylamino, 2-methylamino-2-methylpropylamino and 4-methylaminobutylamino;

for di-[(1–6C)alkyl]amino-(2–6C)alkylamino: 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino, 2-dimethylamino-2-methylpropylamino and 4dimethylaminobutylamino;

for N-(1–6C)alkyl-halogeno-(2–6C)alkylamino: N-(2-chloroethyl)-N-methylamino, N-(2-bromoethyl)-N-methylamino and N-(2-bromoethyl)-N-ethylamino;

for N-(1–6C)alkyl-hydroxy-(2–6C)alkylamino: N-(2-hydroxyethyl)-N-methylamino, N-(3-hydroxypropyl)-N-methylamino and N-ethyl-N-(2-hydroxyethyl)amino;

for N-(1–6C)alkyl-(1–6C)alkoxy-(2–6C)alkylamino: N-methyl-N-(2-methoxyethyl)amino, N-methyl-N-(3-methoxypropyl)amino and N-ethyl-N-(2-methoxyethyl)amino;

for N-(1–6C)alkyl-cyano-(1–6C)alkylamino: N-(cyanomethyl)-N-methylamino;

for N-(1–6C)alkyl-carboxy-(1–6C)alkylamino: N-carboxymethyl-N-methylamino and N-(2-carboxyethyl)-N-methylamino;

for N-(1–6C)alkyl-(1–6C)alkoxycarbonyl-(1–6C)alkylamino: N-methoxycarbonylmethyl-N-methylamino, N-(2-ethoxycarbonylethyl)-N-ethylamino and N-(2-tert-butoxycarbonylethyl)-N-methylamino;

for N-(1–6C)alkyl-carbamoyl-(1–6C)alkylamino: N-carbamoylmethyl-N-methylamino and N-(2-carbamoylethyl)-N-methylamino;

for N-(1–6C)alkyl-N-(1–6C)alkylcarbamoyl-(1–6C)alkylamino: N-(N-methylcarbanoylmethyl)-N-methylamino, N-(N-ethylcarbamoylmethyl)-N-methylamino and N-[2-(N-methylcarbamoyl)ethyl]-N-methylamino;

for N-(1–6C)alkyl-N,N-di-[(1–6C)alkyl]carbamoyl (1–6C)alkylamino: N-(N,N-dimethylcarbamoylmethyl)-N-methylamino and N-[2-(N-dimethylcarbamoyl)ethyl]-N-methylamino;

for N-(1–6C)alkyl-amino-(2–6C)alkylamino: N-(2-aminoethyl)-N-methylamino, N-(3-aminopropyl)-N-methylamino and N-(4-aminobutyl)-N-methylamino;

for N-(1–6C)alkyl-(1–6C)alkylamino-(2–6C)alkylainio: N-(2-methylaminoethyl)-N-methylamino, N-(2-ethylaminoethyl)-N-methylamino, N-(3-methylaminopropyl)-N-methylamino, N-(3-ethylaminopropyl)-N-ethylamino and N-(4-methylaminobutyl)-N-methylamino;

for N-(1–6C)alkyl-di-[(1–6C)alkyl]amino-(2–6C)alkylamino: N-(2-dimethylaminoethyl)-N-methylamino, N-(2-diethylaminoethyl)-N-methylamino, N-(3-dimethylaminopropyl)-N-methylamino and N-(4-dimethylaminobutyl)-N-methylamino;

for halogeno-(2–6C)alkanoylamino: 2-chloroacetamido and 3-chloropropionamido;

for hydroxy-(2–6C)alkanoylamino: 2-hydroxyacetamido and 3-hydroxypropionamido;

for (1–6C)alkoxy-(2–6C)alkanoylamino: 2-methoxyacetamido and 3-methoxypropionamido;

for cyano-(2–6C)alkanoylamino: 2-cyanoacetamido and 3-cyanopropionamido;

for carboxy-(2–6C)alkanoylamino: 2-carboxyacetamido and 3-carboxypropionamido;

for (1–6C)alkoxycarbonyl-(2–6C)alkanoylamino: 2-methoxycarbonylacetamido, 2-(tert-butoxycarbonyl)acetamido and 3-methoxycarbonylpropionamido;

for carbamoyl-(2–6C)alkanoylamino: 2-carbamoylacetamido, 3-carbamoylpropionamido and 4-carbamoylbutyramido;

for N-(1–6C)alkylcarbamoyl-(2–6C)alkanoylamino: 2-(N-methylcarbamoyl)acetamido and 3-(N-ethylcarbamoyl)propionamido;

for N,N-di-[(1–6C)alkyl]carbamoyl-(2–6C)alkanoylamino: 2-(N,N-dimethylcarbamoyl)acetamido, 2-(N,N-diethylcarbamoyl)acetamido and 3-(N,N-dimethylcarbamoyl)propionamido;

for amino-(2–6C)alkanoylamino: 2-aminoacetamido, 2-aminopropionamido and 3-aminopropionamido;

for (1–6C)alkylamino-(2–6C)alkanoylamino: 2-methylaminoacetamido, 2-ethylaminoacetamido, 2-methylaminopropionamido and 3-methylaminopropionamido;

for di-[(1–6C)alkyl]amino-(2–6C)alkanoylamino: 2-dimethylaminoacetamido, 2-diethylaminoacetamido, 2-dimethylaminopropionamido and 3-dimethylaminopropionamido.

When, as defined hereinbefore, any of the substituents on $Q^1$ or $Q^2$ which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, suitable substituents so formed include, for example, substituted heterocyclyl-(1–6C)alkoxy groups such as 2-hydroxy-3-piperidinopropoxy and 2-hydroxy-3-morpholinopropoxy, substituted amino-(2–6C)alkoxy groups such as 3-amino-2-hydroxypropoxy, substituted (1–6C)alkylamino-(2–6C)alkoxy groups such as 2-hydroxy-3-methylaminopropoxy, substituted di-[(1–6C)alkyl]amino-(2–6C)alkoxy groups such as 3-methylamino-2-hydroxypropoxy, 3-[N-(3-dimethylaminopropyl)-N-methylamino]propoxy and 3-[N-(3-dimethylaminopropyl)-N-methylamino]-2-hydroxypropoxy, substituted heterocyclyl-(1–6C)alkylamino groups such as 2-hydroxy-3-piperidinopropylamino and 2-hydroxy-3-morpholinopropylamino, substituted amino-(2–6C)alkylamino groups such as 3-amino-2-hydroxypropylamino, substituted (1–6C)alkylamino-(2–6C)alkylamino groups such as 2-hydroxy-3-methylaminopropylamino, substituted di-[(1–6C)alkyl]amino-(2–6C)alkylamino groups such as 3-dimethylamino-2-hydroxypropylamino, 3-[N-(3-dimethylaminopropyl)-N) -methylamino]propylamino and 3-[N-(3-dimethylaminopropyl)-N-methylamino]-2-hydroxypropylamino and substituted (1–6C)alkylamino-(1–6C)alkyl groups such as 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric, hydrobromic, sulphuric, trifluoroacetic, citric or maleic acid; or, for example a salt of a compound of the Formula I which is sufficiently acidic, for example an alkali or alkaline earth metal salt such as a calcium or magnesium salt, or an ammonium salt, or a salt with an organic base such as methylanine, dimethylamine, trimethylamnine, piperidine, morpholine or tris-(2-hydroxyethyl)amine.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, *Advanced Drug Delivery Reviews*, 8, 1–38 (1992);
d) H. Bundgaard, et al., *Journal of Pharmaceutical Sciences*, 77, 285 (1988); and
e) N. Kakeya, et al., *Chem. Pharm. Bull.*, 32, 692 (1984).

Examples of such pro-drugs may be used to form in-vivo-cleavable esters of a compound of the Formula I. An in-vivo-cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1–6C)alkoxymethyl esters, for example methoxymethyl;
(1–6C)alkanoyloxymethyl esters, for example pivaloyloxymethyl; phthalidyl esters; (3–8C) cycloalkoxycarbonyloxy(1–6C)alkyl esters, for example 1-cyclohexylcarbonyloxyethyl; 1,3-dioxolan-2-ylmethyl esters, for example 5-methyl-1,3-dioxolan-2-ylmethyl; and (1–6C)alkoxycarbonyloxyethyl esters, for example 1-methoxycarbonyloxyethyl; and may be formed at any carboxy group in the compounds of this invention.

Particular novel compounds of the invention include, for example, amide derivatives of the Formula I, or pharrnaceutically-acceptable salts thereof, wherein:

(a) $R^3$ is (1–6C)alkyl such as methyl, ethyl, propyl and isopropyl, preferably methyl and ethyl, more preferably methyl; and $Q^1$, $R^2$, $Q^2$, p and q have any of the meanings defined hereinbefore or in this section relating to particular novel compounds of the invention;

(b) $R^3$ is halogeno such as fluoro, bromo and chloro, preferably chloro and bromo, more preferably chloro; and $Q^1$, $R^2$, $Q^2$, p and q have any of the meanings defined hereinbefore or in this section relating to particular novel compounds of the invention;

(c) $Q^1$ is a heteroaromatic 5- or 6-membered monocyclic ring or a 9- or 10-membered bicyclic ring with up to five ring heteroatoms selected from oxygen, nitrogen and sulphur which optionally bears 1, 2 or 3 substituents selected from hydroxy, halogeno, trifluoromethyl, cyano, nitro, amino, carboxy, (1–6C)alkyl, (1–6C)alkoxy, (1–3C)alkylenedioxy, (1–6C)alkylamino, di-[(1–6C)alkyl]amino, (1–6C)alkoxycarbonyl, (2–6C)alkanoyl, halogeno-(1–6C)alkyl, (1–6C)alkoxy-(1–6C)alkyl, amino-(1-6C)alkyl, (1–6C)alkylamino-(1–6-C)alkyl, di-[(1–6C)alkyl]amino-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1-6C)alkoxy, (1–6C)alkoxycarbonyl-(1–6C)alkoxy, amino-(2–6C)alkoxy, (1-$^6$C)alkylamino-(2-6C)alkoxy, di-[(1–6C)alkyl]amino-(2–6C)alkoxy, pyridyl-(1–6C)alkyl, imidazolyl-(1–6C)alkyl, pyridyl-(1–6C)alkoxy, imidazolyl-(1–6C)alkoxy, pyrrolidinyl, piperidinyl, morpholinyl, piperazinyl, 4-(1–6C)alkylpiperazinyl, 4-(2–6C)alkanoylpiperazinyl, pyrrolidinyl-(1–6C)alkyl, piperidinyl-(1–6C)alkyl, morpholinyl-(1–6C)alkyl, piperazinyl-(1–6C)alkyl, 4-(1-6C)alkylpiperazinyl-(1–6C)alkyl, 4-(2–6C)alkanoylpiperazinyl-(1-6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1-6C)alkylpiperazinyl-(2–6C)alkoxy and 4-(2–6C)alkanoylpiperazinyl-(2–6C)alkoxy; and $R^2$, $R^3$, $Q^2$, p and q have any of the meanings defined hereinbefore or in this section relating to particular novel compounds of the invention;

(d) $Q^1$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, halogeno, trifluoromethyl, cyano, nitro, amino, carboxy, (1–6C)alkyl, (1–6C)alkoxy, (1–6C)alkylamino, di-[(1-6C)alkyl]amino and (1–6C)alkoxycarbonyl; and $R^2$, $R^3$, $Q^2$, p and q have any of the meanings defined hereinbefore or in this section relating to particular novel compounds of the invention;

(e) $Q^1$ is 2- or 3-furyl, 2- or 3-thienyl, 2-, 4- or 5-oxazolyl, 3-, 4 or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2-, 4- or 5-pyrimidinyl, 2-pyrazinyl, 2-, 3-, 5-, or 6-benzofuranyl, 2-, 3-, 5- or 6-indolyl, 2-, 3-, 5- or 6-benzothienyl, 2-, 5-, or 6-benzoxazolyl, 2-, 5- or 6-benzimidazolyl, 2-, 5- or 6-benzothiazolyl, 3-, 5- or 6-indazolyl, 5-bezofurazanyl, 2-, 3-, 6- or 7-quinolyl, 3-, 6- or 7-isoquinolyl, 2-, 6- or 7-quinazolinyl, 2-, 6-, or 7-quinoxalinyl, or 1,8-naphthyridin-2-yl or 1,8-naphthyridin-3-yl which optionally bears 1 or 2 substituents selected from hydroxy, halogeno, trifluoromethyl, cyano, nitro, amino, carboxy, (1–6C)alkyl, (1–6C)alkoxy, (1–6C)alkylamino, di-[(1-6C)alkyl]amino and (1–6C)alkoxycarbonyl; and $R^2$, $R^3$, $Q^2$, p and q have any of the meanings defined hereinbefore or in this section relating to particular novel compounds of the invention;

(f) p is 0; and $Q^1$, $R^3$, $Q^2$ and q have any of the meanings defined hereinbefore or in this section relating to particular novel compounds of the invention;

(g) q is 0, and $Q^2$ is phenyl which optionally bears 1, 2 or 3 substituents selected from hydroxy, halogeno, trifluoromethyl, cyano, amino, (1–6C)alkyl, (1–6C)alkoxy, (1–3C)alkylenedioxy, (1–6C)alkylamino, di-[(1–6C)alkyl]amino, (2–6C)alkanoyl, halogeno-(1 6C)alkyl, (1–6C)alkoxy-(1–6C)alkyl, (1–6C)alkylamino-(1–6C)alkyl, di-[(1–6C)alkyl]amino-(1-6C)alkyl, halogeno-(2–6C)alkoxy, hydroxy-(2–6C)alkoxy, (1–6C)alkoxy-(2–6C)alkoxy, cyano-(2–6C)alkoxy, carboxy-(2–6C)alkoxy, (1–6C)alkoxycarbonyl-(1–6C)alkoxy, amino-(2–6C)alkoxy, (1–6C)alkylamino-(2–6C)alkoxy, di-[(1–6)alkyl]amino-(2-6C)alkoxy, halogeno-(2–6C)alkylamino, hydroxy-(2–6C)alkylamino, (1–6C)alkoxy-(2–6C)alkylamino, amino-(2–6C)alkylamino, (1–6C)alkylamino-(2–6C)alkylamino, di-[(1–6C)alkyl]amino) -(2–6C)alkylamino, N-(1–6C)alkyl-halogeno-(2–6C)alkylamino, N-(1–6C)alkyl-hydroxy) -(2–6C)alkylamino, N-(1–6C)alkyl-(1–6C)alkoxy-(2-6C)alkylamino, N-(1-6C)alkyl-amino -(2–6C)alkylamino, N-(1–6C)alkyl-1–6C)alkylamino-(2-6C)alkylamino, N-1-6C)alkyl) -di-[(1–6C)alkyl]amino-(2–6C)alkylamino, phenyl, benzyl, benzyloxy, pyridyl, imidazolyl, pyridyl-(1–6C)alkyl, imidazolyl-(1–6C)alkyl, pyridyl-(1–6C)alkoxy, imidazolyl-(1–6C)alkoxy, pyrrolidinyl, piperidinyl, morpholinyl, piperazinyl, 4-(1–6C)alkylpiperazinyl, 4-(2–6C)alkanoylpiperazinyl, pyrrolidinyl-(1–6C)alkyl, piperidinyl-(1-6C)alkyl, morpholinyl-(1–6C)alkyl, piperazinyl-(1–6C)alkyl, 4-(1–6C)alkylpiperazinyl-(1–6C)alkyl, 4-(2–6C)alkanoylpiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1-6C)alkylpiperazinyl (2–6C)alkoxy and 4-(2–6C)alkanoylpiperazinyl-(2–6C)alkoxy; and $Q^1$, $R^2$, $R^3$ and p have any of the meanings defined hereinbefor* or in this section relating to particular novel compounds of the invention;

(h) q is 0, and $Q^2$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, halogeno, trifluoromethyl, cyano, nitro, amino, carboxy, (1–6C)alkyl, (1–6C)alkoxy, (1–6C)alkylamino, di-[(1-6C)alkyl]amino and (1–6C)alkoxycarbonyl; and $Q^1$, $R^2$, $R^3$ and p have any of the meanings defined hereinbefore or in this section relating to particular novel compounds of the invention;

(i) q is 0, and $Q^2$ is 2- or 3-furyl, 2- or 3-thienyl, 2-, 4- or 5-oxazolyl, 3-, 4-, or 5-isoxazolyl, 2-, 4- or 5-imidazolyl, 3- or 4-pyrazolyl, 2-, 4- or 5-thiazolyl, 3-, 4-, or 5-isothiazolyl, 2-, 3- or 4-pyridyl, 3- or 4-pyridazinyl, 2-, 4- or 5-pyrimidinyl, 2-pyrazinyl, 2-, 3-, 5- or 6-benzofuranyl, 2-, 3-, 5- or 6-indolyl, 2-, 3-, 5- or 6-benzothienyl, 2-, 5-, or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or or 7-quinazolinyl, 2-, 6- or 7-quinoxalinyl, 1,8-naphthyridin-2-yl or 1,8-naphthyridin-3-yl which optionally bears 1 or 2 substituents selected from hydroxy, halogeno, trifluoromethyl, cyano, nitro, amino, carboxy, (1–6C)alkyl, (1–6C)alkoxy, (1–6C)alkylamino, di-[(1–6C)alkyl]amino and (1–6C)alkoxycarbonyl; and $Q^1$, $R^2$, $R^3$ and p have any of the meanings defined hereinbefore or in this section relating to particular novel compounds of the invention;

(j) q is 0, and $Q^2$ is 4- or 5-oxazolyl, 4- or 5-isoxazolyl, 4- or 5-thiazolyl, 4- or 5-isothiazolyl, 2-, 3- or 4-pyridyl, 5- or 6-benzofuranyl, 5- or 6-benzothienyl, 5- or 6-benzothiazolyl, 2-, 3-, 6- or 7-quinolyl, 2-, 6- or 7-quinazolinyl, 2-, 6- or 7-quinoxalinyl, 1,8-naphthyridin-2-yl or 1,8-naphthyridin-3-yl which optionally bears 1, 2 or 3 substituents selected from hydroxy, fluoro, chloro, trifluoromethyl, cyano, methyl, ethyl, methoxy and ethoxy; and $Q^1$, $R^2$, $R^3$ and p have any of the meanings defined hereinbefore or in this section relating to particular novel compounds of the invention; and (k) q is 1, 2, 3 or 4, and $Q^2$ is cycloalkyl; and $Q^1$, $R^2$, $R^3$ and p have any of the meanings defined hereinbefore or in this section relating to particular novel compounds of the invention.

A preferred compound of the invention is an amide derivative of the Formula I
wherein
$R^3$ is methyl, ethyl, chloro or bromo;
$Q^1$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which optionally bears 1 or 2 substituents selected from hydroxy, fluoro, chloro, trifluoromethyl, cyano, methyl, ethyl, methoxy and ethoxy;

p is 0;

q is 0; and $Q^2$ is phenyl which bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, acetyl, propionyl, chloromethyl, methoxymethyl, 2-methoxyethyl, methylaminomethyl, ethylaminomethyl, dimethylaminomethyl, diethylaminomethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, cyanomethoxy, carboxymethoxy, methoxycarbonylmethoxy, ethoxycarbonylmethoxy, tert-butoxycarbonylmethoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-chloroethylamino, 2-hydroxyethylamino, 2-methoxyethylarmino, 2-ethoxyethylamino, 2-aminoethylamino, 2-methylaminoethylamino, 2-ethylaminoethylamino, 2-dimethylaminoethylamino, 2-diethylaminoethylamino, N-(2-chloroethyl)-N-methylamino, N-(2-hydroxyethyl)-N-methylamino, N-(2-methoxyethyl)-N-methylamino, N-(2-ethoxyethyl)-N-methylamino, N-(2-aminoethyl)-N-methylamino, N-(2-methylaminoethyl)-N-methylamino, N-(2-dimethylaminoethyl)-N-methylamino, N-(3-aminopropyl)-N-methylamino, N-(3-methylaminopropyl)-N-methylamino, N-(3-ethylaminopropyl)-N-methylamino, N-(3-dimethylaminopropyl)-N-methylamino, N-(3-diethylaminopropyl)-N-methylamino, phenyl, benzyl, benzyloxy, 2-pyridylmethoxy, 2-(imidazol-1-yl)ethoxy, 3-(imidazol-1-yl)propoxy, pyrrolidin-1-yl, piperidino, morpholino, piperazin-1-yl, 4-methylpiperazin-1-yl, 4-acetylpiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, piperidin-4-yloxy, 1-methylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4-acetylpiperazin-1-yl)propoxy, or $Q^2$ is oxazolyl, isoxazolyl, thiazolyl, isothiazolyl, pyridyl, benzofuranyl, benzothienyl, benzothiazolyl, quinolyl, quinazolinyl, quinoxalinyl or 1,8-naphthyridinyl which optionally bears 1 or 2 substituents selected from hydroxy, fluoro, chloro, trifluoromethyl, cyano, methyl, ethyl, methoxy and ethoxy;

or a pharmaceutically-acceptable salt thereof.

A further preferred compound of the invention is an amide derivative of the Formula I wherein $R^3$ is methyl or chloro;

$Q^1$ is 3-isoxazolyl, 4-thiazolyl, 3- or 4-pyridyl, 5- or 6-benzothiazolyl, 6- or 7-quinolyl, 6- or 7-quinazolinyl, 2-, 6- or 7-quinoxalinyl or 1,8-naphthyridin-3-yl which optionally bears 1 or 2 substituents selected from hydroxy, fluoro, chloro, methyl and ethyl;

p is 0;

q is 0; and $Q^2$ is phenyl which optionally bears 1 or 2 substituents selected from fluoro, chloro, trifluoromethyl, cyano, methoxy and dimethylamino;

or a pharmaceutically-acceptable salt thereof.

A further preferred compound of the Formula I wherein $R^3$ is methyl or chloro;

$Q^1$ is 3-isoxazolyl, 4-thiazolyl, 3- or 4-pyridyl, 5- or 6-benzothiazolyl, 6- or 7-quinolyl, 6- or 7-quinazolinyl, 2-, 6- or 7-quinoxalinyl or 1,8-naphthyridin-3-yl which optionally bears 1 or 2substituents selected from hydroxy, fluoro, chloro, methyl and ethyl;

p is 0;

q is 0; and $Q^2$ is 4- or 5-isoxazolyl, 4-thiazolyl, 3- or 4-pyridyl, 5- or 6-benzothiazolyl, 6- or 7-quinolyl, 6- or 7-quinazolinyl, 2-, 6- or 7-quinoxalinyl or 1,8-naphthyridin-3-yl which optionally bears a substituent selected from hydroxy, fluoro, chloro, methyl and ethyl;

or a pharmaceutically-acceptable salt thereof.

A further preferred compound of the invention is an amide derivative of the Formula I wherein $R^3$ is methyl or chloro;

$Q^1$ is 3-isoxazolyl, 4-thiazolyl, 3- or 4-pyridyl, 5- or 6-benzothiazolyl, 6- or 7-quinolyl, 6- or 7-quinazolinyl, 2-, 6- or 7quinoxalinyl or 1,8-naphthyridin-3-yl which optionally bears 1or 2 substituents selected from hydroxy, fluoro, chloro, methyl and ethyl;

p is 0;

q is 1 or 2; and $Q^2$ is cyclobutyl, cyclopentyl or cyclohexyl;

or a pharmaceutically-acceptable salt thereof.

A more preferred compound of the invention is an amide derivative of the Formula I wherein $R^3$ is methyl or chloro;

$Q^1$ is 3-isoxazolyl, 3-pyridyl, 6-benzothiazolyl, 6-quinolyl, 6-quinazolinyl, 6-quinoxalinyl or 1,8-naphthyridin-3-yl which optionally bears a substituent selected from hydroxy, chloro and methyl;

p is 0;

q is 0; and $Q^2$ is phenyl which optionally bears 1 or 2 substituents selected from fluoro, chloro, trifluoromethyl, cyano, methoxy and dimethylamino;

or a pharmaceutically-acceptable salt thereof

A further more preferred compound of the invention is an amide derivative of the Formula I wherein $R^3$ is methyl or chloro;

$Q^1$ is 3-isoxazolyl, 3-pyridyl, 6-benzothiazolyl, 6-quinolyl, 6-quinazolinyl, 6-quinoxalinyl or 1,8-naphthyridin-3-yl which optionally bears a substituent selected from hydroxy, chloro and methyl;

p is 0;

q is 0; and $Q^2$ is 5-isoxazolyl or 3-pyridyl which optionally bears a substituent selected from chloro and methyl;

or a pharmaceutically-acceptable salt thereof.

A further more preferred compound of the invention is an amide derivative of the Formula I wherein $R^3$ is methyl or chloro;

$Q^1$ is 3-isoxazolyl, 3-pyridyl, 6-benzothiazolyl, 6-quinolyl, 6-quinazolinyl, 6-quinoxalinyl or 1,8-naphthyridin-3-yl which optionally bears a substituent selected from hydroxy, chloro and methyl;

p is 0;

q is 2; and $Q^2$ is cyclohexyl;

or a pharmaceutically-acceptable salt thereof particular preferred compound of the invention is, for example 6-chloro-N-[5-(3-dimethylaminobenzamido)-2-methylphenyl]pyridine-3-carboxamide, N-[2-methyl-5-(3-trifluoromethylbenzamido)phenyl]quinoline-6-carboxamide, N-[5-(3-dimethylaminobenzamido)-2-methylphenyl]benzothiazole-6-carboxamide, N-[5-(4-cyanobenzamido)-2-methylphenyl]quinoline-6-carboxamide,
N-(5-benzamido-2-methylphenyl)quinoline-6-carboxamide,
N-[5-(3-dimethylaminobenzamido)-2-methylphenyl]-4-hydroxyquinazoline-6-carboxamide,
N-[5-(3-dimethylaminobenzamido)-2-methylphenyl]-2-methyl-1,8-naphthyridine-3-carboxamide,
N-[2-chloro-5-(4-cyanobenzamido)phenyl]quinoline-6-carboxamide or
N-[5-(5-isoxazolylcarbonylamino)-2-methylphenyl]quinoline-6-carboxamide;
or a pharmaceutically-acceptable salt thereof.

In a further aspect of the present invention there is provided a group of novel compounds of the Formula I wherein $Q^1$ is substituted by a basic substituent selected from the substituents for $Q^1$ defined hereinbefore. This group of compounds possesses improved TNFα inhibitory potency in one or both of the PBMC and Human Whole Blood (HWB) tests described hereinafter.

In a further aspect of the present invention there is provided a group of novel compounds of the Formula I wherein $Q^1$ is substituted by a basic substituent selected from the substituents for $Q^1$ defined hereinbefore and $Q^2$ is a phenyl or heteroaryl group as defined hereinbefore which also bears a basic substituent selected from the substituents for $Q^2$ defined hereinbefore. This group of compounds possesses improved TNFα inhibitory potency in one or both of the PBMC and Human Whole Blood tests described hereinafter.

Suitable basic substituents include, for example, amine derivatives such as amino, (1–6C)alkylamino, di-[(1–6C)alkyl]amino-(1–6C)alkyl, di-[(1–6C)alkyl]amino-(2–6C)alkoxy, di-[(1–6C)alkyl]amino-(2–6C)alkylamino, a heteroaryl group such as a nitrogen-containing heteroaryl group, for example imidazolyl and pyridyl and a heterocyclyl group such as a nitrogen-containing heterocyclyl group, for example morpholino.

Particular novel compounds of these further aspects of the invention include, for example, amide derivatives of the Formula I, or pharmaceutically-acceptable salts thereof, wherein:

(a) $R^3$ is (1–6C)alkyl such as methyl, ethyl, propyl and isopropyl, preferably methyl and ethyl, more preferably methyl; and $Q^1$, $R^2$, $Q^2$, p and q have any of the meanings defined in this section relating to particular novel compounds of the invention;

(b) $R^3$ is halogeno such as fluoro, bromo and chloro, preferably chloro and bromo, more preferably chloro; and $Q^1$, $R^2$, $Q^2$, p and q have any of the meanings defined in this section relating to particular novel compounds of the invention;

(c) $Q^1$ is a heteroaromatic 5- or 6-membered monocyclic ring or a 9- or 10-membered bicyclic ring with up to five ring heteroatoms selected from oxygen, nitrogen and sulphur which bears 1 or 2 basic substituents selected from amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2-6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino, di-[(1–6C)alkyl]amino-(2–6C) alkanoylamino, arylamino, N-(1–6C)alkyl-arylamino, aryl-(1–6C)alkylamino, N-(1–6C)alkyl-aryl-(1–6C)alkylamino, heteroaryl, heteroaryl-1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino and N-(1–6C)alkyl-heterocyclyl-(1–C)alkylamino, and wherein any of the basic substituents on $Q^1$ as defined hereinbefore which comprise a $CH_2$ group which is attached to 2 carbon atoms or a $CH_3$ group which is attached to a carbon atom may optionally bear-on each said $CH_2$ or $CH_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a basic substituent on $Q^1$ may optionally bear 1 or 2 substituents selected from hydroxy, halogeno, (1–6C)alkyl, (1–6C)alkoxy, (2–6C)alkanoyl, amino, (1–6C)alkylamino, di-[(1–6C)alkyl]amino, hydroxy-(1–6C)alkyl, (1–6C)alkoxy-1–6C)alkyl, amino-(1–6C)alkyl, (1–6C)alkylamino-1–6C)alkyl, di-[(1–6C)alkyl]amino-(1–6C)alkyl, aryl and aryl-(1–6C)alkyl, and wherein $Q^1$ may optionally bear 1 further substituent selected from hydroxy, halogeno, trifluoromethyl, cyano, (1–6C)alkyl and (1–6C)alkoxy; and $R^3$, $R^2$, $Q^2$, p and q have any of the meanings defined in this section relating to particular novel compounds of the invention;

(d) $Q^1$ is a heteroaromatic 5- or 6-membered monocyclic ring or a 9- or 10-membered bicyclic ring with up to five ring heteroatoms selected from oxygen, nitrogen and sulphur which bears 1 basic substituent selected from amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino, di-[(1–6C)alkyl]amino-(2–6C)alkanoylamino, pyridyl, pyridyl-(1–6C)alkyl, pyridyloxy, pyridyl-(1–6C)alkoxy, pyridylamino, N-(1–6C)alkyl-pyridylamino, pyridyl-(1–6C)alkylamino, N-(1–6C)alkyl-pyridyl-(1–6C)alkylamino, pyrrolidinyl, piperidinyl, morpholinyl, piperazinyl, 4-(1–6C)alkylpiperazinyl, homopiperazinyl, 4-(1–6C)alkylhomopiperazinyl, pyrrolidinyl-(1–6C)alkyl, piperidinyl-(1–6C)alkyl, morpholinyl-(1–6C)alkyl, piperazinyl-(1–6C)alkyl, 4-(1–6C)alkylpiperazinyl-(1–6C)alkyl, homopiperazinyl-(1–6C)alkyl, 4-(1–6C)alkylhomopiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl2–6C)alkoxy, 4-(1–6C)alkylpiperazinyl-(2–6C)alkoxy, pyrrolidinylamino, piperidinylamino, N-(1–6C)alkyl-pyrrolidinylamino, N-(1–6C)alkyl-piperidinylamino, pyrrolidinyl-(1–6C)alkylamino, piperidinyl-(1–6C)alkylamino, morpholinyl-(1–6C)alkylamino, piperazinyl-(1–6C)alkylamino, 4-(1–6C)alkylpiperazinyl-(1–6C)alkylamino, N-(1–6C)alkyl-pyrrolidinyl-(1–6C)alkylamino, N-(1–6C)alkyl-piperidinyl-(1–6C)alkylamino, N-(1–6C)alkyl-morpholinyl-(1–6C)alkylamino, N-(1–6C)alkyl-piperazinyl-(1–6C)alkylamino and N-(1–6C)alkyl-4-(1–6C)alkylpiperazinyl-(1–6C)alkylamino, and wherein any of the basic substituents on $Q^1$ as defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkylamino and di-[(1–6C)alkyl]amino, and wherein any pyridyl or heterocyclyl group in a basic substituent on $Q^1$ may optionally bear 1 or 2 substituents selected from hydroxy, (1–6C)alkyl, (1–6C)alkoxy, (2–6C)alkanoyl, hydroxy-(1–6C)alkyl and benzyl, and wherein $Q^1$ may optionally bear 1 further substituent selected from hydroxy, halogeno, trifluoromethyl, cyano, (1–6C)alkyl and (1–6C)alkoxy; and $R^3$, $R^2$, $Q^2$, p and q have any of the meanings defined in this section relating to particular novel compounds of the invention;

(e) $Q^1$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which bears 1 or 2 basic substituents selected from those defined in paragraph (c) or (d) inmmediately hereinbefore and optionally bears 1 further substituent selected from those defined in paragraph (c) or (d) immediately hereinbefore; and $R^3$, $R^2$, $Q^2$, p and q have any of the meanings defined in this section relating to particular novel compounds of the invention;

(f) $Q^1$ is 2- or 3-furyl, 2- or 3-thienyl, 2-, 4- or 5-oxazolyl, 3-, 4- or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2-, 4- or 5-pyrimidinyl, 2-pyrazinyl, 2-, 3-, 5- or 6-benzofuranyl, 2-, 3-, 5- or 6-indolyl, 2-, 3-, 5- or 6-benzothienyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or 7-quinazolinyl, 2-, 6- or 7-quinoxalinyl, 1,8-naphthyridin-2-yl or 1,8-naphthyridin-3-yl which bears 1 or 2 basic substituents selected from those defined in paragraph (c) or (d) immediately hereinbefore and optionally bears 1 further substituent selected from those defined in paragraph (c) or (d) immediately hereinbefore; and $R^3$, $R^2$, $Q^2$, p and q have any of the meanings defined in this section relating to particular novel compounds of the invention;

(g) $Q^1$ is 2-, 3- or 4-pyridyl which bears 1 basic substituent selected from those defined in paragraph (c) or (d) immediately hereinbefore and optionally bears 1 further substituent selected from those defined in paragraph (c) or (d) immediately hereinbefore; and $R^3$, $R^2$, $Q^2$, p and q have any of the meanings defined in this section relating to particular novel compounds of the invention;

(h) p is 0; and $Q^1$, $R^3$, $Q^2$ and q have any of the meanings defined in this section relating to particular novel compounds of the invention;

(i) q is 0, and $Q^1$, $R^3$, $R^2$, $Q^2$ and m have any of the meanings defined in this section relating to particular novel compounds of the invention;

(j) $Q^2$ is aryl or a heteroaromatic 5- or 6-membered monocyclic ring or a 9- or 10-membered bicyclic ring with up to five ring heteroatoms selected from oxygen, nitrogen and sulphur which optionally bears 1 or 2 basic substituents selected from amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino, di-[(1–6C)alkyl]amino-(2–6C)alkanoylamino, arylamino, N-(1–6C)alkyl-arylamino, aryl-(1–6C)alkylamino, N-(1–6C)alkyl-aryl-(1–6C)alkylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N-(1–6C)alkyl-heteroaryl-(1–6C)alkylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino and N-(l-6C)alkyl-heterocyclyl-(1–6C)alkylamino, and wherein any of the basic substituents on $Q^2$ as defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl, and wherein any aryl, heteroaryl or heterocyclyl group in a basic substituent on $Q^2$ may optionally bear 1 or 2 substituents selected from hydroxy, halogeno, (1–6C)alkyl, (1–6C)alkoxy, (2–6C)alkanoyl, amino, (1–6C)alkylamino, di-[(1–6C)alkyl]amino, hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl, and wherein $Q^2$ may optionally bear 1 further substituent selected from hydroxy, halogeno, trifluoromethyl, cyano, (1–6C)alkyl and (1–6C)alkoxy; and $Q^1$, $R^3$, $R^2$, p and q have any of the meanings defined in this section relating to particular novel compounds of the invention;

(k) $Q^2$ is aryl or a heteroaromatic 5- or 6-membered monocyclic ring or a 9- or 10-membered bicyclic ring with up to five ring heteroatoms selected from oxygen, nitrogen and sulphur which optionally bears 1 basic substituent selected from amino, (1–6C)alkylamino, di-[(1–6C)alkyl]amino, amino-(1–6C)alkyl, (1–6C)alkylamino-(1–6C)alkyl, di-[(1–6C)alkyl]amino-(1–6C)alkyl, amino-(2–6C)alkoxy, (1–6C)alkylamino-(2–6C)alkoxy, di-[(1–6C)alkyl]amino-(2–6C)alkoxy, amino-(2–6C)alkylamino, (1–6C)alkylamino-(2–6C)alkylamino, di-[(1–6C)alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, amino-(2–6C)alkanoylamino, (1–6C)alkylamino-(2–6C)alkanoylamino, di-[(1–6C)alkyl]amino-(2–6C)alkanoylamino, pyridyl, pyridyl-(1–6C)alkyl, pyridyloxy, pyridyl-(1–6C)alkoxy, pyridylamino, N-(1–6C)alkyl-pyridylamino, pyridyl-(1–6C) alkylamino, N-(1–6C)alkyl-pyridyl-(1–6C)alkylamino, pyrrolidinyl, piperidinyl, morpholinyl, piperazinyl, 4-(1–6C)alkylpiperazinyl, homopiperazinyl, 4-(1–6C) alkylhomopiperazinyl, pyrrolidinyl-(1–6C)alkyl, piperidinyl(1–6C)alkyl, morpholinyl-(1–6C)alkyl, piperazinyl-(1–6C)alkyl, 4(1–6C)alkylpiperazinyl-(1–6C)alkyl, homopiperazinyl-(1–6C)alkyl, 4-(1–6C) alkylhomopiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy, pyrrolidinylamino, piperidinylamino, N-(1–6C)alkyl-pyrrolidinylamino, N-(1–6C)alkyl-piperidinylamino, pyrrolidinyl-(1–6C)alkylamino, piperidinyl-(1–6C) alkylamino, morpholinyl-(1–6C)alkylamino, piperazinyl-(1–6C)alkylamino, 4-(1–6C) alkylpiperazinyl-(1–6C)alkylamino, N-(1–6C)alkyl-pyrrolidinyl-(1–6C)alkylamino, N-(1–6C)alkyl-piperidinyl-(1–6C)alkylamino, N-(1–6C)alkyl-morpholinyl-(1–6C)alkylamino, N-(1–6C)alkyl-piperazinyl-(1–6C)alkylamino and N-(1–6C)alkyl4-(1–6C)alkylpiperazinyl-(1–6C)alkylamino, and wherein any of the basic substituents on $Q^2$ as defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkylamino and di-[(1–6C) alkyl]amino, and wherein any pyridyl or heterocyclyl group in a basic substituent on $Q^2$ may optionally bear 1 or 2 substituents selected from hydroxy, (1–6C)alkyl, (1–6C)alkoxy, (2–6C)alkanoyl, hydroxy-(1–6C)alkyl and benzyl, and wherein $Q^2$ may optionally bear 1 further substituent selected from hydroxy, halogeno, trifluoromethyl, cyano, (1–6C)alkyl and (1–6C)alkoxy; and $Q^1$, $R^3$, $R^2$, p and q have any of the meanings defined in this section relating to particular novel compounds of the invention;

(l) $Q^2$ is aryl or a heteroaromatic 5- or 6-membered monocyclic ring with up to five ring heteroatoms selected from oxygen, nitrogen and sulphur which bears 1 basic substituent selected from amino, (1–6C) alkylamino, di-[(1–6C)alkyl]amino, amino-(1–6C) alkyl, (1–6C)alkylamino-(1–6C)alkyl, di-[(1–6C) alkyl]amino-(1–6C)alkyl, amino-(2–6C)alkoxy, (1–6C)alkylamino-(2–6C)alkoxy, di-[(1–6C)alkyl] amino-(2–6C)alkoxy, amino-(2–6C)alkylamino, (1–6C)alkylamino-(2–6C)alkylamino, di-[(1–6C) alkyl]amino-(2–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl] amino-(2–6C)alkylamino, amino-(2–6C) alkanoylamino, (1–6C)alkylamino-(2–6C) alkanoylamino, di-[(1–6C)alkyl]amino-(2–6C) alkanoylamino, pyridyl, pyridyl-(1–6C)alkyl, pyridyloxy, pyridyl-(1–6C)alkoxy, pyridylamino, N-(1–6C)alkyl-pyridylamino, pyridyl-(1–6C) alkylamino, N-(1–6C)alkyl-pyridyl-(1–6C)alkylamino, pyrrolidinyl, piperidinyl, morpholinyl, piperazinyl, 4-(1–6C)alkylpiperazinyl, homopiperazinyl, 4-(1–6C) alkylhomopiperazinyl, pyrrolidinyl-(1–6C)alkyl, piperidinyl-(1–6C)alkyl, morpholinyl-(1–6C)alkyl, piperazinyl-(1–6C)alkyl, 4-(1–6C)alkylpiperazinyl-(1–6C)alkyl, homopiperazinyl-(1–6C)alkyl, 4-(1–6C) alkylhomopiperazinyl-(1–6C)alkyl, pyrrolidinyloxy, piperidinyloxy, 1-(1–6C)alkylpiperidinyloxy, pyrrolidinyl-(2–6C)alkoxy, piperidinyl-(2–6C)alkoxy, morpholinyl-(2–6C)alkoxy, piperazinyl-(2–6C)alkoxy, 4-(1–6C)alkylpiperazinyl-(2–6C)alkoxy, pyrrolidinylamino, piperidinylamino, N-(1–6C)alkyl-pyrrolidinylamino, N1–6C)alkyl-piperidinylamino, pyrrolidinyl-(1–6C)alkylamino, piperidinyl-(1–6C) alkylamino, morpholinyl-(1–6C)alkylamino, piperazinyl-(1–6C)alkylamino, 4-(1–6C) alkylpiperazinyl-(1–6C)alkylamino, N-(1–6C)alkyl-pyrrolidinyl-(1–6C)alkylamino, N-(1–6C)alkyl-piperidinyl-(1–6C)alkylamino, N-(1–6C)alkyl-morpholinyl-(1–6C)alkylamino, N-(1–6C)alkyl-piperazinyl(1–6C)alkylamino and N-(1–6C)alkyl-4-(1–6C)alkylpiperazinyl-(1–6C)alkylamino, and wherein any of the basic substituents on $Q^2$ as defined hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkylamino and di-[(1–6C) alkyl]amino, and wherein any pyridyl or heterocyclyl group in a basic substituent on $Q^2$ may optionally bear 1 or 2 substituents selected from hydroxy, (1–6C)alkyl, (1–6C)alkoxy, (2–6C)alkanoyl, hydroxy-(1–6C)alkyl and benzyl, and wherein $Q^2$ may optionally bear 1 further substituent selected from hydroxy, halogeno, trifluoromethyl, cyano, (1–6C)alkyl and (1–6C)alkoxy; and $Q^1$, $R^3$, $R^2$, p and q have any of the meanings defined in this section relating to particular novel compounds of the invention;

(m) $Q^2$ is furyl, thienyl, oxazolyl, isoxazolyl, imidazolyl, pyrazolyl, thiazolyl, isothiazolyl, pyridyl, pyridazinyl, pyrimidinyl, pyrazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl or naphthyridinyl which bears 1 or 2 basic substituents selected from those defined in paragraph (j), (k) or (l) immediately hereinbefore and optionally bears 1 further substituent selected from those defined in paragraph (j), (k) or (l) immediately hereinbefore; and $Q^1$, $R^3$, $R^2$, p and q have any of the meanings defined in this section relating to particular novel compounds of the invention;

(n) $Q^2$ is 2- or 3-furyl, 2- or 3-thienyl, 2-, 4- or 5-oxazolyl, 3-, 4- or 5-isoxazolyl, 2-, 4- or 5-imidazolyl, 3- or 4-pyrazolyl, 2-, 4- or 5-thiazolyl, 3-, 4- or 5-isothiazolyl, 2-, 3- or 4-pyridyl, 3- or 4-pyridazinyl, 2-, 4- or 5-pyrimidinyl, 2-pyrazinyl, 2-, 3-, 5- or 6-benzofuranyl, 2-, 3-, 5- or 6-indolyl, 2-, 3-, 5- or 6-benzothienyl, 2-, 5- or 6-benzoxazolyl, 2-, 5- or 6-benzimidazolyl, 2-, 5- or 6-benzothiazolyl, 3-, 5- or 6-indazolyl, 5-benzofurazanyl, 2-, 3-, 6- or 7-quinolyl, 3-, 6- or 7-isoquinolyl, 2-, 6- or 7-quinazolinyl, 2-, 6- or 7-quinoxalinyl, 1,8-naphthyridin-2-yl or 1,8-naphthyridin-3-yl which bears 1 or 2 basic substituents selected from those defined in paragraph (j), (k) or (l) immediately hereinbefore and optionally bears 1 further substituent selected from those defined in paragraph (j), (k) or (l) immediately hereinbefore; and $Q^1$, $R^3$, $R^2$, p and q have any of the meanings defined in this section relating to particular novel compounds of the invention; and (o) $Q^2$ is phenyl or 2-, 3- or 4-pyridyl which bears 1 basic substituent selected from those defined in paragraph (j), (k) or (l) immediately hereinbefore and optionally bears 1 further substituent selected from those defined in paragraph (j), (k) or (l) immediately hereinbefore; and $Q^1$, $R^3$, $R^2$, p and q have any of the meanings defined in this section relating to particular novel compounds of the invention;

A preferred compound of this aspect of the invention is an amide derivative of the Formula I
wherein
$R^3$ is methyl, ethyl, chloro or bromo;
$Q^1$ is 2-, 3- or 4-pyridyl which bears 1 basic substituent selected from amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-amino-2-methylpropylamino, 4-aminobutylamino, 3-methylaminopropylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-dimethylaminopropyl)-N-methylamino, 4-pyridyl, 2-pyridylmethyl, 2-pyridylmethoxy, pyrrolidin-1-yl, piperidino, morpholino, piperazin-1-yl, 4-methylpiperazin-1-yl, 4-ethylpiperazin-1-yl, 4-acetylpiperazin-1-yl, homopiperazin-1-yl, 4-methylhomopiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, 4-(2-hydroxyethyl) piperazin-1-yl, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-yl)ethoxy, 3-(4-acetylpiperazin-1-yl)propoxy, 1-benzylpiperidin-4-ylamino, 2-pyrrolidin-1-ylethylamino, 3-pyrrolidin-1-ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl) propylamino, 2-(1-methylpyrrolidin-2-ylethylamino, 3-(1-methylpyrrolidin-2-yl)propylamino, 3-amino-2-hydroxypropoxy, 2-hydroxy-3-methylaminopropoxy, 3-dimethylamino-2-hydroxypropoxy, 3-amino-2-hydroxypropylamino, 2-hydroxy-3-methylaminopropylamino, 3-dimethylamino-2-hydroxypropylamino, 3-[N-(3-dimethylaminopropyl)-N-methylamino]-2-hydroxypropoxy, 2-hydroxy-3-pyrrolidin-1-ylpropoxy, 2-hydroxy-3-piperidinopropoxy, 2-hydroxy-3-morpholinopropoxy, 2-hydroxy-3-pyrrolidin-1-ylpropylamino, 2-hydroxy-3-piperidinopropylamino, 2-hydroxy-3-morpholinopropylamino, 3-[N-(3-dimethylaminopropyl)-N-methylamino]-2-hydroxypropylamino, 2-aminoethylaminomethyl, 3-aminopropylaminomethyl, 2-methylaminoethylaminomethyl, 3-methylaminopropylaminomethyl, 2-dimethylaminoethylaminomethyl, 3-dimethylaminopropylaminomethyl, 2-pyrrolidin-1-ylethylaminomethyl, 3-pyrrolidin-1-ylpropylaminomethyl, 2-piperidinoethylaminomethyl, 3-piperidinopropylaminomethyl, 2-morpholinoethylaminomethyl, 3-morpholinopropylaminomethyl, 2-piperazin-1-ylethylaminomethyl, 3-piperazin-1-ylpropylaminomethyl, 2-(4-methylpiperazin-1-yl) ethylaminomethyl and 3-(4-methylpiperazin-1-yl) propylaminomethyl, and wherein $Q^1$ may optionally bear 1 further substituent selected from hydroxy, fluoro, chloro, trifluoromethyl, cyano, methyl, ethyl, methoxy and ethoxy;

p is 0;

q is 0; and $Q^2$ is phenyl, 5-isoxazolyl or 3- or 4-pyridyl which optionally bears 1 or 2 substituents selected from hydroxy, fluoro, chloro, trifluoromethyl, cyano, amino, methyl, ethyl, methoxy, ethoxy, methylamino, dimethylamino, aminomethyl, methylaminomethyl, dimethylaminomethyl, 2-aminoethoxy, 3-aminopropoxy, 2-methylaminoethoxy, 3-methylaminopropoxy, 2-methylaminoethoxy, 3-dimethylaminopropoxy, 2-aminoethylamino, 3-aminopropylamino, 4-aminobutylamino, 3-methylaminopropylamino, 2-dimethylaminoethylamino, 3-dimethylaminopropylamino, 4-dimethylaminobutylamino, N-(2-dimethylaminoethyl)-N-methylamino, N-(3-dimethylaminopropyl)-N-methylamino, 4-pyridyl, 2-pyridylmethoxy, pyrrolidin-1-yl, morpholino, piperidino, piperazin-1-yl, 4-methylpiperazin-1-yl, 4-ethylpiperazin-1-yl, 4-acetylpiperazin-1-yl, homopiperazin-1-yl, 4-methylhomopiperazin-1-yl, pyrrolidin-1-ylmethyl, piperidinomethyl, morpholinomethyl, piperazin-1-ylmethyl, 4-methylpiperazin-1-ylmethyl, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-pyrrolidin-1-ylethylamino, 3-pyrrolidin-1-ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino and 3-(4-methylpiperazin-1-yl) propylamino; or a pharmaceutically-acceptable salt thereof.

A further preferred compound of this aspect of the invention is an amide derivative of the Formula I
wherein
$R^3$ is methyl or chloro;
$Q^1$ is 3-pyridyl or 4-pyridyl which bears a substituent selected from 2-aminoethylamino, 3-aminopropylamino, 2-amino-2-methylpropylamino, 4-aminobutylamino, 3-methylaminopropylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-aminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, 4-methylhomopiperazin-1-yl, 1-benzylpiperidin-4-ylamino, 2-pyrrolidin-1ylethylamino, 3-pyrrolidin-1ylpropylamino, 2-morpholinoethylio, 3-morpholinopropylamino, 2-piperidinoethylamino, 3-piperidinopropylamin, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino or 3-amino-2-hydroxypropylamino;

p is 0;

q is 0; and $Q^2$ is phenyl, 5-isoxazolyl, 3-pyridyl or 4-pyridyl which optionally bears 1 or 2 substituents selected from hydroxy, fluoro, chloro, trifluoromethyl, cyano, amino, methyl, ethyl, methoxy, ethoxy, methylamino, dimethylamino, pyrrolidin-1-yl, morpholino, piperidino, piperazin-1-yl or 4-methylpiperazin-1-yl;

or a pharmaceutically-acceptable salt thereof.

A further preferred compound of this aspect of the invention is an amide derivative of the Formula I wherein $R^3$ is methyl or chloro;

$Q^1$ is 3-pyridyl or 4-pyridyl which bears a substituent selected from 2-aminoethylamino, 3-aminopropylamino, 2-amino-2-methylpropylamino, 4-aminobutylamino, 3-methylaminopropylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, 4-methylhomopiperazin-1-yl, 1-benzylpiperidin-4-ylamino, 2-pyrrolidin-1ylethylamino, 3-pyrrolidin-1ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino or 3-amino-2-hydroxypropylamino;

p is 0;

q is 0, and $Q^2$ is phenyl or 4-pyridyl which bears a substituent selected from pyrrolidin-1-yl, morpholino and piperidino;

or a pharmaceutically-acceptable salt thereof

A further preferred compound of this aspect of the invention is an amide derivative of the Formula I wherein $R^3$ is methyl or chloro;

$Q^1$ is 3-pyridyl or 4-pyridyl which bears a substituent selected from 2-aminoethylamino, 3-aminopropylamino, 2-amino-2-methylpropylamino, 4-aminobutylamino, 3-methylaminopropylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, homopiperazin-1-yl, 4-methylhomopiperazin-1-yl, 1-benzylpiperidin-4-ylamino, 2-pyrrolidin-1ylethylamino, 3-pyrrolidin-1ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino or 3-amino-2-hydroxypropylamino;

p is 0;

q is 0; and $Q^2$ is phenyl or 4-pyridyl which bears a substituent selected from pyrrolidin-1-yl, morpholino and piperidino and which optionally bears a further substituent selected from fluoro and trifluoromethyl;

or a pharmaceutically-acceptable salt thereof.

A further more preferred compound of this aspect of the invention is an amide derivative of the Formula I wherein $R^3$ is methyl;

$Q^1$ is 3-pyridyl or 4-pyridyl which bears a substituent selected from 2-aminoethylamino, 3-aminopropylamino, 2-amino-2-methylpropylamino, 4-aminobutylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-dimethylaminopropyl)-N-methylamino, 4-methylpiperazin-1-yl, 4-(2-hydroxyethyl)piperazin-1-yl, 3-morpholinopropylamino or 2-(1-methylpyrrolidin-2-yl)ethylamino;

p is 0;

q is 0; and $Q^2$ is 2-morpholinopyrid-4-yl;

or a pharmaceutically-acceptable salt thereof.

A further more preferred compound of this aspect of tie invention is an amide derivative of the Formula I wherein $R^3$ is methyl or chloro;

$Q^1$ is 3-pyridyl or 4-pyridyl which bears a substituent selected from 2-aminoethylamino, 3-aminopropylamino, 2-amino-2-methylpropylamino, 4-aminobutylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3dimethylaminopropyl)-N-methylamino, homopiperazin-1-yl, 4-methylpiperazin-1-yl, 4-ethylpiperazin-1-yl, 4-(2-hydroxyethyl)piperazin-1-yl, 3-morpholinopropylamino or 2-(1-methylpyrrolidin-2-yl)ethylamino;

p is 0;

q is 0; and $Q^2$ is 2-morpholinopyrid-4-yl, 3-fluoro-5-morpholinophenyl or 3-morpholino-5-trifluoromethylphenyl;

or a pharmaceutically-acceptable salt thereof.

A particular preferred compound of these further aspects of the invention is, for example:

6-[-(2-dimethylaminoethyl)-N-methylamino]-N-[2-methyl-5-(2-morpholinopyrid-4-ylcarbonylamino)phenyl]pyridine-3-carboxamide, 6-(2-amino-2-methylpropylamino)-N-[2-methyl-5-(2-morpholinopyrid-4-ylcarbonylamino)phenyl]pyridine-3-carboxamide, 6-(2-diethylaminoethylamino)-N-[2-methyl-5-(2-morpholinopyrid-4-ylcarbonylamino)phenyl]pyridine-3-carboxamide, 6-(3-dimethylaminopropylamino)-N-[2-methyl-5-(2-morpholinopyrid-4-ylcarbonylamino)phenyl]pyridine-3-carboxamide, 6-[2-(1-methylpyrrolidin-2-yl)ethylamino]-N[2-methyl-5-(2-morpholinopyrid-4-ylcarbonylamino)phenyl]pyridine-3-carboxamide, 6-(3-morpholinopropylamino)-N-[2-methyl-5-(2-morpholinopypid-4-ylcarbonylamino)phenyl]pyridine-3-carboxamide, 6-(4-dimethylaminobutylamino)-N-[2-methyl-5-(2-morpholopyrid-4-ylcarbonylamino)phenyl]pyridine-3-carboxamide, 2(4-methylpipezin-1-yl)-N-[2-methyl-5-(2-morpholinopyrid-4-ylcarbonylamino)phenyl]-pyridine-4-carboxamide or 2-[4-(2-hydroxyethyl)piperazin-1-yl]-N-[2-methyl-5-(2-morpholinopyrid-4-ylcarbonylamino)phenyl]pyridine-4-carboxamide;

or a pharmaceutically-acceptable salt thereof

A further particular preferred compound of these further aspects of the invention is, for example:

6-(3-morpholinopropylamino)-N-[2-methyl-5-(3-fluoro-5-morpholinobenzamido)phenyl]pyridine-3carboxamide, 6-(4-methylpiperazin-1-yl)-N-[2-methyl-5-(3-fluoro-5-morpholinobenzamido)phenyl]pyridine-3-carboxamide, 6-(4-ethylpiperazin-1-yl)-N-[2-methyl-5-(2-morpholinopyrid-4-ylcarbonylamino)phenyl]pyridine-3-carboxamide, N-[2-chloro-5-(2-morpholinopyrid-4-ylcarbonylamino)phenyl]-2-(4-methylpiperazin-1-yl)pyridine-4-carboxamide or N-[2-chloro-5-(2-morpholinopyrid-4-ylcarbonylamino)phenyl]-2-[4-(2-hydroxyethyl)piperazin-1-yl]pyridine-4-carboxamide;

or a pharmaceutically-acceptable salt thereof.

An amide derivative of the Formula I, or a pharmaceutically-acceptable salt or in-vivo-cleavable ester thereof, may be prepared by any process known to be applicable to the preparation of chemically-related compounds. Such processes, when used to prepare a novel amide derivative of the Formula I are provided as a further feature of the invention and are illustrated by the following representative process variants in which, unless otherwise stated, $Q^1$, $R^2$, $R^3$, p, q and $Q^2$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt or in-vivo-cleavable ester thereof, may be prepared by reacting an aniline of the Formula II

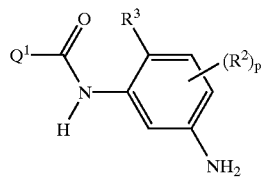

with an acid of the Formula III, or a reactive derivative thereof,

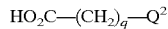

under standard amide bond forming conditions, wherein variable groups are as defined hereinbefore and wherein any functional group is protected if necessary, and:

(i) removing any protecting groups; and
(ii) optionally forming a pharmaceutically-acceptable salt or in-vivo-cleavable ester.

A suitable activated derivative of an acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as N-hydroxybenzotriazole; an acyl azide, for example an azide formed by the reaction of the lo acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, methylene chloride, 1,2-dimethoxyethane, N,N-dimethylformamide, N,N-dimethylacetamide, N-methylpyrrolidin-2-one, dimethylsulphoxide or acetone, and at a temperature in the range, for example, −78 to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 14 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl); and (2–6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, 12-nitrobenzyloxycarbonyl; tri-alkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The aniline of Formula II may be prepared by reduction of the corresponding nitro compound of Formula IV.

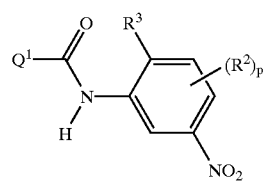

IV

Typical reaction conditions include the use of ammonium formate in the presence of a catalyst (for example palladium-on-carbon) in the presence of an organic solvent (preferably a polar protic solvent), preferably with heating, for example to about 60° C. Any functional groups are protected and deprotected as necessary.

The nitrobenzene of Formula IV may be prepared by the reaction of a benzoic acid of Formula V, or an activated derivative thereof as defined hereinbefore,

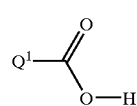

V with an aniline of Formula VI

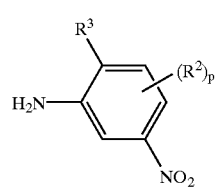

VI under suitable amide bond forming conditions as defined hereinbefore.

Typical conditions include activating the carboxy group of the compound of Formula V, for example by treatment with a halo reagent (for example oxalyl chloride) to form an acyl halide in an organic solvent at ambient temperature and then reacting the activated compound with the aniline of Formula VI. Any functional groups are protected and deprotected as necessary.

(b) A compound of the Formula I, or a pharmaceutically-acceptable salt or in-vivo- cleavable ester thereof, may be prepared by reacting an acid of the Formula V, or an activated derivative thereof as defined hereinbefore,

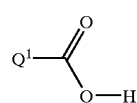

V with an aniline of the Formula VII

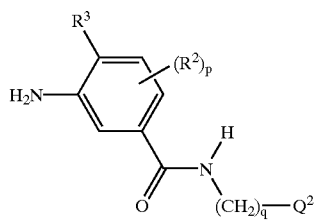

under standard amide bond forming conditions as defined hereinbefore, wherein variable groups are as defined hereinbefore and wherein any functional group is protected, if necessary, and:
(i) removing any protecting groups;
(ii) optionally forming a pharmaceutically-acceptable salt or in-vivo-cleavable ester.

The aniline of Formula VII may be prepared by reduction of the corresponding nitro compound using convention procedures as defined hereinbefore or as illustrated in the Examples.

(c) A compound of the Formula I wherein a substituent on $Q^1$ or $Q^2$ is (1–6C)alkoxy or substituted (1–6C)alkoxy, (1–6C)alkylthio, (1–6C)alkylamino, di-[(1–6C)alkyl]amino or substituted (1–6C)alkylamino, may be prepared by the alkylation, conveniently in the presence of a suitable base as defined hereinbefore, of an amide derivative of the Formula I wherein a substituent on $Q^1$ or $Q^2$ is hydroxy, mercapto or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, in the presence of a suitable base as defined hereinbefore, in a suitable inert solvent or diluent as defined hereinbefore and at a temperature in the range, for example, 10 to 140° C., conveniently at or near ambient temperature.

(d) A compound of the Formula I wherein a substituent on $Q^1$ or $Q^2$ is (1–6C)alkanoylamino or substituted (2–6C)alkanoylamino may be prepared by the acylation of a compound of the Formula I wherein a substituent on $Q^1$ or $Q^2$ is amino.

A suitable acylating agent is, for example, any agent known in the art for the acylation of amino to acylamino, for example an acyl halide, for example a (1–6C)alkanoyl chloride or bromide, conveniently in the presence of a suitable base, as defined hereinbefore, an alkanoic acid anhydride or mixed anhydride, for example a (1–6C)alkanoic acid anhydride such as acetic anhydride or the mixed anhydride formed by the reaction of an alkanoic acid and a (1–6C)alkoxycarbonyl halide, for example a (1–6C)alkoxycarbonyl chloride, in the presence of a suitable base as defined hereinbefore. In general the acylation is carried out in a suitable inert solvent or diluent as defined hereinbefore and at a temperature, in the range, for example, –30 to 120° C., conveniently at or near ambient temperature.

(e) A compound of the Formula I wherein a substituent on $Q^1$ or $Q^2$ is (1–6C)alkanesulphonylamino may be prepared by the reaction of a compound of the Formula I wherein a substituent on $Q^1$ or $Q^2$ is amino with a (1–6C)alkanesulphonic acid, or an activated derivative thereof.

A suitable activated derivative of a (1–6C)alkanesulphonic acid is, for example, an alkanesulphonyl halide, for example an alkanesulphonyl chloride formed by the reaction of the sulphonic acid and an inorganic acid chloride, for example thionyl chloride. The reaction is preferably carried out in the presence of a suitable base as defined hereinbefore, particularly pyridine, and in a suitable inert solvent or diluent as defined hereinbefore, particularly methylene chloride.

(f) A compound of the Formula I wherein a substituent on $Q^1$ or $Q^2$ is carboxy, carboxy-(1–6C)alkyl, carboxy-(1–6C)alkoxy, carboxy-(1–6C)alkylamino, N-(1–6C)alkyl-carboxy-(1–6C)alkylamino or carboxy-(2–6C)alkanoylamino may be prepared by the cleavage of a compound of the Formula I wherein a substituent on $Q^1$ or $Q^2$ is (1–6C)alkoxycarbonyl, (1–6C)alkoxycarbonyl-(1–6C)alkyl, (1–6C)alkoxycarbonyl-(1–6C)alkoxy, (1–6C)alkoxycarbonyl-(1–6C)alkylamino, N-(1–6C)alkyl-(1–6C)alkoxycarbonyl-(1–6C)alkylamino or (1–6C)alkoxycarbonyl-(2–6C)alkanoylamino as appropriate.

The cleavage reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10 to 150° C., preferably at or near ambient temperature.

(g) A compound of the Formula I wherein a substituent on $Q^1$ or $Q^2$ is amino, (1–6C)alkylamino, di-[(1–6C)alkyl]amino, substituted (1–6C)alkylamino, substituted N-(1–6C)alkyl-(1–6C)alkylamino or a N-linked heterocyclyl group may be prepared by the reaction, conveniently in the presence of a suitable base as defined hereinbefore, of an amide derivative of the Formula I wherein a substituent on $Q^1$ or $Q^2$ is a suitable leaving group with an appropriate amine or a N-containing heterocycle.

A suitable N-containing heterocycle is, for example, pyrrolidine, morpholine, piperidine, piperazine, homopiperazine or a 4-(1–6C)alkylpiperazine.

A suitable leaving group is, for example, a halogeno group such as fluoro, chloro or bromo, a (1–6C)alkanesulphonyloxy group such as methanesulphonyloxy or an arylsulphonyloxy group such as 4-toluenesulphonyloxy.

The reaction is conveniently carried out in the presence of a suitable inert diluent or carrier as defined hereinbefore and at a temperature in the range, for example, 20 to 200° C., conveniently in the range 75 to 150° C.

The following biological assays and Examples serve to illustrate the present invention.

Biological Assays

The following assays can be used to measure the p38 kinase-inhibitory, the TNF-inhibitory and anti-arthritic effects of the compounds of the present invention:

In vitro Enzyme Assay

The ability of compounds of the invention to inhibit the enzyme p38 kinase was assessed. Activity of test compounds against each of the p38α and p38μ isoforms of the enzyme was determined.

Human recombinant MKK6 (GenBank Accesion Number G1209672) was isolated from Image clone 45578 (*Genomics* 1996, 33, 151) and utilised to produce protein in the form of a GST fusion protein in a pGEX vector using analogous procedures to those disclosed by J. Han et al., *Journal of Biological Chemistry*, 1996, 271, 2886–2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p388α and p38β genes using analogous procedures to those described by J. Han et al., *Biochimica et Biolphysica Acta,* 1995, 1265, 224–227 and Y. Jiang et al., *Journal of Biological Chemistry,* 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforns of p38. The activation incubate comprised p38α (10 μl of 10 mg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM Mg(OCOCH$_3$)$_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)] was then added followed by 'Labelled ATP' [10 μl; comprising 50 μM ATP, 0.1 μCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In Vitro Cell-Based Assays (i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 μg/ml streptomycin, 2 mM glutamine and 1% heat-inactivated human AB serum (Sigma H-1 513)]. Compounds were solubilised in DMSO at a concentration of 50 mM, diluted 1:100 in culture medium and subsequently serial dilutions were made in culture medium containing 1% DMSO. PBMCs (2.4×10$^5$ cells in 160 μl culture medium) were incubated with 20 μl of varying concentrations of test compound (triplicate cultures) or 20 μl culture medium containing 1% DMSO (control wells) for 30 minutes at 37° C. in a humidified (5%CO$_2$/95% air) incubator (Falcon 3072; 96 well flat-bottom tissue culture plates). 20 μl lipopolysaccharide [LPS *E.Coli* 0111:B4 (Sigma L4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H. and Endres, S., Int. *J. Immunopharmac.* (1993), 15(3), 409–413) or an inhibitor of proTNFα convertase (for example, see McGeehan, G. M. et al. *Nature* (1994) 370, 558–561). Plates were incubated for 7 hours at 37° C. (humidified incubator) after which 100 μl of the supernatant was removed from each well and stored at –70° C. (96 well round-bottom plates; Corning 25850). TNFα levels were determined in each sample using a human TNFα ELISA (see WO92/10190 and *Current Protocols in Molecular Biology*, vol 2 by Frederick M. Ausbel et al., John Wiley and Sons Inc.).

% inhibition=(*LPS* alone–medium alone)–(test concentration–medium alone)×100(*LPS* alone–medium alone)

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin, 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20 μl LPS (final concentration 10 μg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology,* vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex vivo/In vivo assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 mm at 4° C. and the harvested plasmas frozen at −20° C. for subsequent assay of their effect on TNFα production by LPS-stimulated human blood. The rat plasma samples were thawed and 175 μl of each sample was added to a set format pattern in a 96 well round bottom plate (Corning 25850). 50 μl of heparinized human blood was then added to each well, mixed and the plate was incubated for 30 min at 37° C. (humidified incubator). LPS (25 μl; final concentration 10 μg/ml) was added to the wells and incubation continued for a further 5.5 hours. Control wells were incubated with 25 μl of medium alone. Plates were then centrifuged for 10 min at 2000 rpm and 200 μl of the supernatants were. transferred to a 96 well plate and frozen at −20° C. for subsequent analysis of TNF concentration by ELISA.

Data analysis by dedicated software calculates for each compound/dose:

% inhibition of *TNFα*=Mean *TNFα*(Controls)−Mean *TNFα*(Treated)×100Mean *TNFα*(Controls)

Alternatively, mice could be used instead of rats in the above procedure.

Test as Anti-Arthritic Agent

Activity of a compound as an anti-arthritic agent was tested as follows. Acid soluble native type II collagen was shown by Trentham et al. [1] to be arhritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Ex,. Med.,* 146, 857.
2. Williams, R. O. et al., (1992) *Proc. Natl. Acad. Sci.* 89, 9784.
3. Williams, R. O. et al., (1995) *Immunology,* 8, 433.
4 Badger, M. B. et al., (1996) *The Journal of Pharmacology and Experimental Therapeutics* 279, 1453–1461.

Although the pharmacological properties of the compounds of the Formula I vary with structural change as expected, in general a compound of the Formula I gives over 30% inhibition of p38α and/or p38β at concentrations up to 10 μM and over 30% inhibition in the PBMC test at concentrations up to 50 μM. No physiologically unacceptable toxicity was observed at the effective dose for compounds tested of the present invention.

By way of example, 6-chloro-N-[5-(3-dimethylaminobenzamido)-2-methylphenyl]pyridine-3-carboxamide [Example 1] has an $IC_{50}$ of approximately 1 μM against p38α and an $IC_{50}$ of approximately 9 μM in the PBMC test;

N-[5-(3dimethylaminobenzamido)-2-methylphenyl] benzothiazole-6-carboxamide [Example 8, Compound No. 2] has an $IC_{50}$ of approximately 0.1 μM against p38α and an $IC_{50}$ of approximately 5 μM in the PBMC test;

N-[2-chloro-5-(4-cyanoberzamido)phenyl]quinoline-6-carboxamnide [Example 10] has an $IC_{50}$ of approximately 0.05 μM against p38α and an $IC_{50}$ of approximately 2 μM in the PBMC test and N[5-(5-isoxazolylcarbonylamino)-2-methylphenyl]quinoline-6carboxamide [Example 14] has an $IC_{50}$ of approximately 0.1 μM against p38α and an $IC_{50}$ of approximately 3 μM in the PBMC test.

As disclosed hereinbefore, a further aspect of the present invention concerns compounds of the Formula I wherein $Q^1$ is substituted by a basic substituent selected from the substituents for $Q^1$ defined hereinbefore and $Q^2$ is a phenyl or heteroaryl group as defined hereinbefore which also bears a basic substituent selected from the substituents for $Q^2$ defined hereinbefore, which compounds possess improved TNFα inhibitory potency in one or both of the PBMC and HWB tests. By way of example, 6-[2-(1-methylpyrrolidin-2-yl)ethylamino]-N-[2-methyl-5 (2-morpholinopyrid-4-ylcarbonylamino)phenyl]pyridine-3-carboxamide [Example 22(18)] has an $IC_{50}$ of approximately 0.05 μM against p38α, an $IC_{50}$ of approximately 0.3 μM in the PBMC test and an $IC_{50}$ of approximately 2 μM in the HWB test; and 6-(3-dimethylaminopropylamino)-N-[2-methyl-5-(2-morpholinopyrid-4-ylcarbonylamino)phenyl]pyridine-3-carboxamide [Example 22(14)] has an $IC_{50}$ of approximately 0.05 μM against p38α and an $IC_{50}$ of approximately 3 μM in the HWB test.

According to a further aspect of the invention there is provided a pharmaceutical composition which comprises an amide derivative of the Formula I, or a pharmaceutically-acceptable or in-vivo-cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided an amide derivative of the Formula I, or a pharmaceutically-acceptable salt or in-vivo-cleavable ester thereof, as defined hereinbefore for use in a method of treatment of the human or animal body by therapy.

According to a further aspect of the invention there is provided the use of an amide derivative of the Formula I, or a pharmaceutically-acceptable salt or in-vivo-cleavable ester thereof, as defined hereinbefore in the manufacture of a medicament for use in the treatment of medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in-vivo-cleavable ester thereof, as defined hereinbefore.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula 1, or a pharmaceutically-acceptable salt or in-vivo-cleavable ester thereof, in the manufacture of a medicament for use in inhibiting TNF, IL-1, IL-6 or IL-8.

In a further aspect the present invention provides a method of inhibiting TNF, IL-1, IL-6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in vivo-cleavable ester thereof In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of rheumatoid arthritis, asthma, irritable bowel disease, multiple sclerosis, AIDS, septic shock, congestive heart failure, ischaemic heart disease or psoriasis.

In a further aspect the present invention provides a method of treating rheumatoid arthritis, asthma, irritable bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt or in-vivo-cleavable ester thereof.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis, AIDS, septic shock, congestive heart failure, ischaemic heart disease, psoriasis and the other disease states mentioned earlier in this specification.

For example, by virtue of their ability to inhibit cytokines, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a flirther feature of the invention there is provided a pharmaceutical composition which comprises a compound of the Formula I, or a pharmaceutically-acceptable salt or in-vivocleavable ester thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase.

The compounds of the Formula I may also be used in the treatment of conditions such as rheumatoid arthritis in combination with antiartlritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiastlunatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
DMF N,N-dimethylformamide
DMSO dimethylsulphoxide

EXAMPLE 1

6-chloro-N-[5-(3-dimethylaminobenzamido)-2-methylphenyl]pyridine-3-carboxamide

6-Chloropyrid-3-ylcarbonyl chloride (0.37 g) was added to a mixture of N-(3-amino4-methylphenyl)-3-dimethylaminobenzamide (0.54 g), potassium carbonate (0.304 g), DMF (5 ml) and methylene chloride (20 ml) and the resultant mixture was stirred at ambient temperature for 16 hours. The mixture was poured into water and extracted with ethyl acetate. The organic extracts were washed with a saturated aqueous sodium chloride solution, dried over magnesium sulphate and evaporated. The residue was purified by column chromatography on silica using a 3:2:1 mixture of isohexane, ethyl acetate and methylene chloride as eluent. There was thus obtained the title compound as a solid (0.122 g); NMR Spectrum: (DMSOd$_6$) 2.19 (s, 6H), 3.28 (s, 3H), 6.88 (m, 1H), 7.25 (m, 4H), 7.57 (m, 1H), 7.7 (d, 1H), 7.84 (d, 1H), 8.36 (m, 1H), 8.95 (d,1H), 10.11 (s, 1H), 10.16 (s, 1H); Mass Spectrum: M+H$^+$ 409 and 411.

The N-(3-amino4-methylphenyl)-3-dimethylaminobenzamide used as starting material was prepared as follows:

Oxalyl chloride (13.0 ml) was added dropwise to a stirred mixture of 3-dimethylaminobenzoic acid (20.3 g) and DMF (a few drops) which had been cooled to 0° C. The mixture was allowed to warm to ambient temperature and was stirred for 4 hours. The resultant mixture was evaporated and the residue was dissolved in methylene chloride (150 ml). 4-Methyl-3-nitroaniline (15.2 g) and triethylamine (27.9 ml) were added in turn and the resultant mixture was stirred at ambient temperature for 16 hours. The reaction mixture was washed in turn with water, with a saturated aqueous solution of sodium bicarbonate and with a saturated aqueous sodium chloride solution, dried over magnesium sulphate and evaporated. The residue was triturated under a mixture of ethyl acetate and isohexane. The solid so obtained was filtered off and recrystallised from ethanol to give N-(3-nitro4-methylphenyl)-3-dimethylamino-benzamnide (6.1 g); NMR Spectrum: (DMSOd$_6$) 2.46 (s, 3H), 2.95 (s, 6H), 6.92 (d, 1H), 7.22 (m, 2H), 7.32 (t, 1H), 7.45 (d, 1H), 7.97 (d, 1H), 8.53 (s, 1H), 10.43 (s, 1H).

After repetition of the previous reactions, a sample (8.25 g) was added to a stirred suspension of ammonium formate (17.4 g), and 10% palladium-on-carbon (1 g) in methanol (250 ml). The mixture was stirred and heated to reflux for 4 hours. The mixture was allowed to cool and then filtered. The filtrate was evaporated and water was added to the residue. The resultant solid was isolated and washed in turn with water, with ethyl acetate and with diethyl ether. The solid was dried in a vacuum oven at 40° C. to give N-(3-amino-4-methylphenyl)-3-dimethylaminobenzamide (6.89 g); NMR Spectrum: (DMSOd$_6$) 2.0 (s, 3H), 2.94 (s, 6H), 4.78 (s, 2H), 6.82 (m, 3H), 7.07 (s, 1H), 7.17 (m, 2H), 7.25 (m, 1H), 9.74 (s, 1H).

The 6-chloropyrid-3-ylcarbonyl chloride used as starting material was prepared by the reaction of 6-chloropyridine-3-carboxylic acid and oxalyl chloride using an analogous procedure to that described hereinbefore in the first part of the portion of this Example which is concerned with the preparation of starting materials.

EXAMPLE 2

N-[2-chloro-5-(4-cyanobenzamido)phenyl]pyridine-3-carboxamide

A mixture of pyrid4-ylcarbonyl chloride (prepared by the reaction of pyridine-4-carboxylic acid and oxalyl chloride; 0.213 g), N-3-amino4-chlorophenyl)-4-cyanobenzamide (0.27 g) and pyridine (4 ml) was stirred and heated to 110° C. for 16 hours. After cooling, the mixture was poured into water (25 ml). The resultant precipitate was collected, washed with water and dried to give the title compound as a solid (0.32 g); NMR Spectrum: (DMSOd$_6$) 7.58 (d, 1H), 7.75 (m, 1H), 7.85 (d, 2H), 8.01 (d, 2H), 8.10 (m, 3H), 8.80(d, 2H); Mass Spectrum: M+H$^+$ 377.

The N-(3-amino4chlorophenyl)-4cyanobenzamide used as starting material was prepared as follows:

4-Cyanobenzoyl chloride (11.92 g) was added slowly to a stirred solution of 4-chloro-3-nitroaniline (10.4 g) in pyridine (20 ml) and the mixture was stirred and heated to 115° C. for 18 hours. The mixture was cooled to ambient temperature and poured into water (150 ml) and stirred for 30 minutes. The resultant precipitate was isolated, washed with water and dried to give N-[4chloro-3-nitrophenyl]4-cyanobenzamide (18 g), m.p. 213° C.; NMR Spectrum: (DMSOd$_6$) 7.78 (d, 1H), 8.05 (m, 3H), 8.1 (d, 2H), 8.58 (s, 1H), 10.93 (s, 1H).

A portion (3.6 g) of the material so obtained was added to a stirred suspension of iron powder (10 g) in a mixture of ethanol (130 ml), water (30 ml) and glacial acetic acid (4 ml). The mixture was heated to 75° C. for 1 hour and thereafter, whilst hot, basified by the addition of sodium carbonate. The mixture was filtered and the filtrate was evaporated. The resultant solid was stirred in water for 3 hours. The solid was isolated and dried to give the required starting material (2.7 g), m.p. 237.7° C.; NMR Spectrum: (DMSOd$_6$) 5.44 (s, 2H), 6.98 (m, 1H), 7.21 (d, 1H), 7.42 (d, 1H), 8.07 (d, 2H), 8.14 (d, 2H), 10.36 (s, 1H).

EXAMPLE 3

N-[5-(3-dimethylaminobenzamido)-2-methylphenyl]quinoxaline-2-carboxamide

Triethylamine (0.28 ml) was added to a stirred mixture of N-(3-amino-4-methylphenyl)-3-dimethylaminobenzamide (0.27 g), 2-quinoxalinylcarbonyl chloride (0.29 g) and methylene chloride (10 ml) and the resultant mixture was stirred at ambient temperature for 16 hours. The reaction mixture was partitioned between methylene chloride and water. The organic phase was washed with a saturated aqueous solution of sodium bicarbonate and evaporated. The residue was triturated under ethyl acetate. There was thus obtained the title compound as a solid (0.175 g); NMR Spectrum: (DMSOd$_6$) 2.31 (s, 3H), 2.95 (s, 6H), 3.31 (s, 3H), 6.91 (d, 1H) 7.27 (m, 4H), 7.59 (d, 1H), 8.01 (m, 2H), 8.24 (m, 3H), 9.56 (s, 1H), 10.15 (s, 1H), 10.42 (s, 1H); Mass Spectrum: M+H$^+$ 416.

EXAMPLE 4

N-[5-(4-chlorobenzamido)-2-methylphenyl]quinoline-6-carboxamide

Triethylamine (0.28 ml) was added to a stirred mixture of 4-chlorobenzoyl chloride (0.29 g), N-(5-amino-2-methylphenyl)quinoline-6-carboxamide (0.28 g) and methylene chloride (10 ml) and the resultant mixture was stirred at ambient temperature for 16 hours. The precipitate was isolated, washed with water and with methylene chloride. There was thus obtained the title compound as a solid (0.208 g); NMR Spectrum: (DMSOd$_6$) 2.24 (s, 3H), 7.24 (d, 1H), 7.52–7.62 (m, 4H), 7.87 (s, 1H), 7.98 (d, 2H), 8.12 (d 1H) 8.46 (d, 1H), 8.52 (d, 1H), 8.65 (s, 1H) 9.00 (s, 1H), 10.15 (s, 1H) 10.31 (s, 1H); Mass Spectrum: M+H$^+$ 416.

The N-(5-amino-2-methylphenylquinoline-6-carboxamide used as starting material was prepared as follows:

Oxalyl chloride (12.73 ml) was added to a solution of 6-quinolinecarboxylic acid (20.3 g) in a mixture of methylene chloride (150 ml) and DMF (1 ml) which had been cooled to 0° C. The mixture was allowed to warm to ambient temperature and was stirred for 4 hours. The mixture was evaporated and the residue was dissolved in a mixture of methylene chloride (150 ml) and DMF (5 ml). 2-Methyl-5-nitroaniline (14.3 g) and triethylamnine (20.35 ml) were added in turn and the mixture was stirred at ambient temperature for 16 hours. The precipitate was isolated, washed with water and with ethyl acetate and dried under vacuum at 55° C. There was thus obtained N-(2-methyl-5-nitrophenyl) quinoline-6-carboxamide as a solid (26.7 g); NMR Spectrum: (DMSOd$_6$) 2.43 (s, 3H), 7.59 (d, 1H), 7.84 (m, 1H), 8.06 (m, 1H), 8.3 (m, 1H), 8.4 (m, 2H), 8.83 (m, 2H), 9.16 (m, 1H), 10.53 (s, 1H).

A mixture of the material so obtained, 10% palladium-on-carbon (1.29 g), ammonium formate (36.5 g) and methanol (500 ml) was stirred and heated to reflux for 2 hours. The mixture was cooled to ambient temperature and filtered through diatomaceous earth. The solvent was evaporated and the residue was triturated under water. The resultant solid was isolated and dried under vacuum at 55° C. to give N-(5-amino-2-methylphenyl)quinoline-6-carboxamide as a solid (14.7 g); NMR Spectrum: (DMSOd$_6$) 2.08 (s, 3H), 6.41 (m, 1H), 6.64 (d, 1H), 6.89 (d, 1H), 7.62 (m, 1H), 8.1 (d, 1H), 8.23 (d, 1H), 8.5 (d, 1H), 8.6 (s, 1H), 8.99 (d, 1H), 9.86 (s, 1H).

EXAMPLE 5

N-[5-(3-dimethylaminobenzamido)-2-methylphenyl]quinoline-6carboxamide

6-Quinolinecarboxylic acid (0.173 g) was added to a stirred suspension of N-(3-amino4-methylphenyl)3- dimethylaminobenzamide (0.135 g), diisopropylethylamine (0.325 ml), 2-(7-azabenzotriazol-1-yl)-1,1,3,3-tetramethyluronium hexafluorophosphate(V) (0.39 g) in DMF (10 ml) and the resultant mixture was stirred at ambient temperature for 16 hours. The solvent was evaporated and the residue was dissolved in methylene chloride and washed with a saturated aqueous sodium bicarbonate solution, dried over magnesium sulphate and evaporated. The residue was triturated under a mixture of ethyl acetate and isohexane. There was thus obtained the title compound as a solid (0.052 g); NMR Spectrum: (DMSOd$_6$) 2.24 (s, 3H), 2.95 (s, 6H), 6.89 (d, 1H), 7.25 (m, 4H), 7.6 (m, 2H), 7.85 (s, 1H), 8.12 (d, 1H), 8.4 (d, 1H), 8.52 (d, 1H), 8.65 (m, 1H), 8.99 (d, 1H), 10.11 (s, 1H), 10.16 (s, 1H); Mass Spectrum: M+H$^+$ 425.

EXAMPLE 6

N-[5-(3,4-dichlorobenzamido)-2-methylphenyl]quinoline-6-carboxamide

Using an analogous procedure to that described in Example 4, 3,4-dichlorobenzoyl chloride was reacted with N-(5-amino-2-methylphenyl)quinoline-6-carboxamide in the presence of triethylamine. The reaction mixture was stirred at ambient temperature for 16 hours and then evaporated. The residue was purified by column chromatography on silica using increasingly polar mixtures of methylene chloride and methanol as eluent. There was thus obtained the title compound in 57% yield; Mass Spectrum: M+H$^+$ 450.

EXAMPLE 7

N-[2-methyl-5-(3-trifluoromethylbenzamido)phenyl]quinoline-6-carboxamide

Phosphoryl chloride (0.045 ml) was added to a stirred mixture of 6-quinolinecarboxylic acid (0.084 g), N-(3-amino4methylphenyl)-3-trifluoromethylbenzamide (0.119 g) and pyridine (1 ml) which had been cooled to 0° C. The reaction mixture was allowed to warm to ambient temperature and was stirred for 16 hours. The mixture was poured into 2N aqueous hydrochloric acid solution. The resultant precipitate was isolated, washed in turn with a saturated aqueous sodium bicarbonate solution and isohexane and dried at 55° C. under vacuum. There was thus obtained the title compound as a solid (0.128 g); NMR Spectrum: (DMSOd$_6$) 2.25 (s, 3H), 7.25 (d, 1H), 7.61 (m, 2H), 7.77 (t, 1H), 7.87 (d, 1H), 7.94 (d, 1H), 8.14 (d, 1H), 8.28 (m, 3H), 8.56 (d, 1H), 8.65 (broad s, 1H), 9.01 (broad s, 1H), 10.17 (s, 1H), 10.46 (s, 1H); Mass Spectrum: M−H$^-$ 448.

The N-(3-amino4-methylphenyl)-3-trifluoromethylbenzamide used as a starting material was obtained as follows:

A mixture of 3-trifluoromethylbenzoyl chloride (9.9 ml), 3-nitro-4-methylaniline (10 g) and pyridine (100 ml) was stirred and heated to 80° C. for 2 hours. The reaction mixture was evaporated and the residue was triturated under 2N aqueous hydrochloric acid solution. The resultant solid was isolated, washed in turn with a saturated aqueous sodium bicarbonate solution, water and isohexane and dried under vacuum at 55° C. There was thus obtained N-(4-methyl-3-nitrophenyl)-3-trifluoromethylbenzamide as a solid (21.91 g); NMR Spectrum: (DMSOd$_6$) 7.49 (d, 1H), 7.78 (m, 1H), 7.99 (m, 2H), 8.27 (m, 2H), 8.51 (s, 1H), 10.77 (s, 1H).

A mixture of a portion (10 g) of the material so obtained, 10% palladium-on-carbon (1.0 g), ammonium formate (19 g) and methanol (250 ml) was stirred and heated to reflux for 1 hour. The mixture was filtered through diatomaceous earth and the filtrate was evaporated. The residue was triturated under water. The resultant solid was isolated and dried under vacuum at 55° C. to give N-(3-amino4-methylphenyl)-3-trifluoromethylbenzamnide as a solid (7.98 g); NMR Spectrum: (DMSOd$_6$) 2.01 (s, 3H), 4.83 (s, 2H), 6.85 (m, 2H), 7.08 (s, 1H), 7.74 (t, 1H), 7.92 (d, 1H), 8.2 (d, 1H), 10.11 (s, 1H).

EXAMPLE 8

Using analogous procedures to those described in the previous Examples, the appropriate acyl chloride was reacted with the appropriate aniline to give the compounds described in Table I. Where required, heteroarylcarbonyl chlorides were prepared from the corresponding heteroarylcarboxylic acids by reaction with oxalyl chloride using an analogous procedure to that described in the first part of the portion of Example 4 which is concerned with the preparation of starting materials.

TABLE I

Heteroaryl—CONH—[Me-substituted phenyl]—NHCO—[phenyl]—R

| No. | Heteroaryl | R | Method | Note |
|-----|------------|---|--------|------|
| 1 | 5-methylisoxazol-3-yl | 3-dimethylamino | Ex. 3 | (a) |
| 2 | 6-benzothiazolyl | 3-dimethylamino | Ex. 3 | (b) |
| 3 | 6-quinolyl | 4-cyano | Ex. 4 | (c) |
| 4 | 6-quinolyl | hydrogen | Ex. 4 | (d) |
| 5 | 6-quinolyl | 4-methoxy | Ex. 6 | (e) |
| 6 | 6-quinolyl | 3-fluoro | Ex. 6 | (f) |
| 7 | 6-quinolyl | 2,4-dimethoxy | Ex. 4 | (g) |
| 8 | 4-hydroxyquinazolin-6-yl | 3-dimethylamino | Ex. 4 | (h) |
| 9 | 6-quinoxalinyl | 3-dimethylamino | Ex. 3 | (i) |
| 10 | 2-methyl-1, 8-naphthyridin-3-yl | 3-dimethylamino | Ex. 3 | (j) |

Notes
(a) The reactants were 5-methylisoxazol-3-ylcarbonyl chloride and N-(3-amino-4-methylpenyl)-3-dimethylaminobenzamide. The product gave the following data: NMR Spectrum: (DMSOd$_6$) 2.17 (s, 3H), 2.94 (s, 6H), 6.63 (s, 1H), 6.9 (d, 1H), 7.19–7.29 (m, 4H), 7.57 (d 1H) 7.81 (s, 1H), 10.09 s, 1H), 10.12 (s, 1H); Mass Spectrum: M + H$^+$ 379.
(b) The reactants were benzothiazol-6-ylcarbonyl chloride and N-(3-amino-4-methylphenyl)-3-dimethylaminobenzamide. The product gave the following data: NMR Spectrum: (DMSOd$_6$) 2.22 (s, 3H), 2.95 (s, 6H), 6.9 (d, 1H), 7.21–7.28 (m, 4H), 7.58 (d 1H) 7.84 (s, 1H), 8.12 (d 1H) 8.2 (d, 1H), 8.79 (s, 1H), 9.55 (s, 1H) 10.04 (s, 1H), 10.1 (s, 1H); Mass Spectrum: M + H$^+$ 431.
(c) The reactants were N-(5-amino-2-methylphenyl)quinoline-6-carboxamide and 4-cyanobenzoyl chloride. The product gave the following data: NMR Spectrum: (DMSOd$_6$) 2.25 (s, 3H), 7.26 (d, 1H), 7.58–7.64 (m, 2H), 7.89 (s, 1H), 8.0 (d, 2H), 8.09–8.14 (m, 3H), 8.28 (d, 1H), 8.49 (d, 1H), 8.65 (s, 1H), 9.0 (s, 1H), 10.16 (s, 1H), 10.48 (s, 1H); Mass Spectrum: M + H$^+$ 407.
(d) The reactants were 6-quinolylcarbonyl chloride and N-(3-amino-4-methylphenyl)benzamide. The product gave the following data: NMR Spectrum: (DMSOd$_6$) 2.24 (s, 3H), 7.24 (d, 1H), 7.5–7.7 (m, 5H), 7.89–7.97 (m, 3H), 8.12 (d, 1H), 8.25 (d, 1H) 8.49 (d, 1H), 8.65 (s, 1H) 9.01 (s, 1H), 10.16 (s, 1H) 10.25 (s, 1H); Mass Spectrum: M + H$^+$ 382.

The N-(3-amino4-methylphenyl)benzamide used as a starting material was prepared as follows:

Benzoyl chloride (1.9 ml) was added to a stirred mixture of 2,4-diaminotoluene (2 g), triethylamine (5.57 ml) and methylene chloride (80 ml) and the mixture was stirred at ambient temperature for 16 hours. The mixture was washed with a saturated aqueous solution of sodium bicarbonate.

The organic phase was dried over magnesium sulphate and evaporated. The residue was triturated with a mixture of ethyl acetate and diethyl ether. There was thus obtained the required starting material (1.32 g); NMR Spectrum: (DMSOd$_6$) 2.01 (s, 3H), 4.8 (s, 2H), 6.82 (m 2H), 7.11 (s, 1H), 7.5 (m, 3H), 7.91 (m, 2H), 9.86 (s, 1H).

(e) The reactants were N-(5-amino-2-methylphenyl) quinoline-6-carboxamide and 4-methoxybenzoyl chloride. The product gave the following data: Mass Spectrum: M+H$^+$ 412.

(f) The reactants were N-(5-amino-2-methylphenyl) quinoline-6-carboxamide and 3-fluorobenzoyl chloride. The product gave the following data: Mass Spectrum: M+H$^+$ 398.

(g) The reactants were N-(5-amino-2-methylphenyl) quinoline-6-carboxamide and 2,4-dimethoxybenzoyl chloride. The product gave the following data: NMR Spectrum: (DMSOd$_6$) 2.22 (s, 3H), 3.82 (s, 3H), 3.94 (s, 3H), 6.6–6.69 (m, 2H), 7.2 (d, 1H), 7.51 (d, 1H), 7.6–7.65 (m, 1H), 7.73 (d, 1H), 7.83 (s, 1H), 8.11 (d, 1H), 8.26 (d, 1H), 8.57 (d,1H), 8.66 (s, 1H), 9.0 (s, 1H), 9.89 (s, 1H), 10.17 (s, 1H); Mass Spectrum: M+H$^+$ 442.

(h) The reactants were 4-oxo-3,4-dihydroquinazolin-6-ylcarbonyl chloride [prepared by the reaction of the corresponding acid (*J. Amer. Chem. Soc.* 1907, 29 85) and oxalyl chloride] and N-(3-amino4-methylphenyl)-3dimethylaminobenzamide. The product gave the following data: NMR Spectrum: (DMSOd$_6$) 2.21 (s, 3H), 2.95 (s, 6H), 6.9 (d, 1H), 7.19–7.32 (m, 4H), 7.58–7.69 (m, 2H), 7.79 (s, 1H), 8.18 (s 1H), 8.24 (d, 1H), 8.74 (s, 1H), 10.1 (s, 1H), 10.11 (s, 1H); Mass Spectrum: M+H$^+$ 442.

(i) The reactants were 6-quinoxalinylcarbonyl chloride and N-(3-amino-4-methylphenyl)3-dimethylaminobenzamide. The product gave the following data: NMR Spectrum: (DMSOd$_6$) 2.24 (s, 3H), 3.05 (s, 6H), 6.9 (d, 1H), 7.23–7.32 (m, 4H), 7.6 (d, 1H), 7.86 (s, 1H), 8.22 (d, 1H), 8.36 (d, 1H), 8.76 (s, 1H), 9.05 (s, 2H), 10.12 (s, 1H), 10.3 (s, 1H); Mass Spectrum: M+H$^+$ 426.

The 6-quinoxalinylcarbonyl chloride used as a starting material was prepared as follows:

A 2N aqueous sodium hydroxide solution (7.95 ml) was added to a solution of methyl quinoxaline-6-carboxylate (1 g) in a mixture of methanol (30 ml) and water (5 ml) and the mixture was stirred at ambient temperature for 16 hours. The reaction mixture was evaporated and the residue was dissolved in water. The solution was acidified to pH3.5 by the addition of dilute aqueous hydrochloric acid and extracted with ethyl acetate. The organic extracts were evaporated and the residue was triturated under a mixture of ethyl acetate and isohexane. There was thus obtained quinoxaline-6-carboxylic acid a solid (0.5 g); NMR Spectrum: (DMSOd$_6$) 8.16 (d, 1H), 8.28 (d, 1H), 8.59 (s, 1H), 9.02 (s, 2H).

Oxalyl chloride (0.065 ml) was added dropwise to a stirred solution of a portion (0.181 g) of the acid so obtained in a mixture of methylene chloride (20 ml) and DMF (a few drops) which had been cooled to 0° C. The mixture was allowed to warm to ambient temperature and was stirred for 4 hours. The solvent was evaporated to give 6-quinoxalinylcarbonyl chloride which was used without further purification.

(j) The reactants were 2-methyl-1,8-naphthyridin-3-ylcarbonyl chloride and N-(3-amino4-methylphenyl)-3-dimethylaminobenzamide. The product gave the following data: NMR Spectrum: (DMSOd$_6$) 2.29 (s, 3H), 2.82 (s, 3H), 2.95 (s, 6H), 6.9 (d, 1H), 7.21–7.28 (m, 4H), 7.58–7.67 (m, 2H) 7.95 (s, 1H), 8.54 (d, 1H) 8.62 (s, 1H), 9.1 (s, 1H), 10.13 (s, 2H); Mass Spectrum: M+H$^+$ 440.

EXAMPLE 9

N-(5-benzamido-2-chlorophenyl)quinoline6-carboxamide

Using an analogous procedure to that described in Example 7, quinoline-6-carboxylic acid was reacted with N-(3-amino4chlorophenyl)benzamide to give the title compound in 47% yield; NMR Spectrum: (DMSOd$_6$) 7.57 (m, 6H), 7.75 (m, 1H), 7.95 (d, 2H), 8.15 (d, 1H), 8.17 (d, 1H), 8.55 (d, 1H), 8.78 (s, 1H), 9.01 (m, 1H), 10.33 (s, 1H), 10.44 (s, 1H); Mass Spectrum: M–H$^-$ 400.

The N-(3-amino4-chlorophenyl)benzamide used as a staring material was obtained as follows:

Benzoyl chloride (5.2 ml) was added to a stirred mixture of 2,4-diaminochlorobenzene (6.42 g), triethylamine (12.5 ml) and methylene chloride (100 ml) which had been cooled to 0° C. The mixture was allowed to warm to ambient temperature and was stirred for 16 hours. The mixture was evaporated and the residue was triturated under a saturated aqueous sodium bicarbonate solution. The resultant solid was isolated, washed in turn with water and isohexane and dried under vacuum at 55° C. There was thus obtained N-(3-aminochlorophenyl)benzamide as a solid (10.38 g); NMR Spectrum: (DMSOd$_6$) 5.32 (s, 2H), 6.9 (m, 1H), 7.1 (d, 1H), 7.37 (d, 1H), 7.52 (m, 3H), 7.9 (d, 2H), 10.05 (s, 1H).

EXAMPLE 10

N-[2-chloro-5-(4-cyanobenzamido)phenyl] quinoline6-carboxamide

Using an analogous procedure to that described in Example 3, quinoline-6-carboxylic acid was reacted with N-(3-amino-4-chlorophenyl)-4-cyanobenzamide. The crude reaction product was purified by column chromatography on silica using a 97:3 mixture of methylene chloride and methanol as eluent. There was thus obtained the title compound in 18% yield; NMR Spectrum: (DMSOd$_6$) 7.58 (d, 1H), 7.62 (m, 1H), 7.77 (m, 1H), 8.01 (d, 2H), 8.12 (t, 4H), 8.28 (d, 2H), 8.56 (d, 1H), 8.67 (s, 1H), 9.01 (d, 1H), 10.34 (s, 1H), 10.67 (s, 1H); Mass Spectrum: M–H$^-$ 425.

EXAMPLE 11

6-chloro-N-[5-(3-cyclohexylpropionamido)-2-methylphenyl]pyridine-3-carboxamide

Using an analogous procedure to that described in Example 3, 6-chloropyrid-3-ylcarbonyl chloride was reacted with N-(3-amino-4-methylphenyl)-3-cyclohexylpropionamide (*J. Med. Chem.* 1996, 39, 3343–3356) to give the title compound; Mass Spectrum: M+H$^+$ 400.

EXAMPLE 12

N-[5-(3-cyclohexylpropionamido)-2-methylphenyl] quinoline-6carboxamide

Using an analogous procedure to that described in Example 5, quinoline-6-carboxylic acid was reacted with N-(3-amino-4-methylphenyl)-3-cyclohexylpropionamide to give the title compound; NMR Spectrum: (DMSOd$_6$) 0.76–1.28 (m, 6H), 1.42–1.78 (m, 7H), 2.2 (s, 3H), 2.28 (t, 2H), 7.17 (d, 1H), 7.39 (d, 1H), 7.6 (m, 1H)), 7.69 (s, 1H), 8.12 (d, 1H), 8.24 (d, 1H), 8.49 (d, 1H), 8.63 (s, 1H), 9.0 (m, 1H), 9.82 (s, 1H), 10.09 (s, 1H); Mass Spectrum: M+H$^+$ 437.

EXAMPLE 13

N-[5-(3-cyclohexylpropionamido)-2-methylphenyl] quinoxaline-6-carboxamide

Using an analogous procedure to that described in Example 5, quinoxaline-6-carboxylic acid was reacted with N-(3-amino4-methylphenyl)-3-cyclohexylpropionamide to give the title compound; NMR Spectrum: (DMSOd$_6$) 0.76–0.97 (m, 2H), 1.04–1.24 (m, 3H), 1.40–1.78 (m, 8H), 2.2 (s, 3H), 2.28 (t, 2H), 7.17 (d, 1H), 7.39 (d, 1H), 7.69 (s, 1H), 8.22 (d, 1H), 8.44 (d, 1H), 8.74 (s, 1H), 9.05 (m, 2H), 9.84 (s, 1H), 10.25 (s, 1H); Mass Spectrum: M+H$^+$ 417.

EXAMPLE 14

N-[5-(5-isoxazolylcarbonylamino)2-methylphenyl] quinoline-6-carboxamide

Using an analogous procedure to that described in Example 4, 5-methylisoxazol-3-ylcarbonyl chloride was reacted with N-(5-amino-2-methylphenyl)quinoline-6-carboxamide in the presence of triethylamine. The reaction mixture was stirred at ambient temperature for 16 hours and then evaporated. The residue was purified by column chromatography on silica using increasingly polar mixtures of methylene chloride and methanol as eluent. There was thus obtained the title compound; Mass Spectrum: M–H$^-$ 425.

EXAMPLE 15

N-[5-(6-chloropyrid-3-ylcarbonylamino)-2-methylphenyl]quinoline-6-carboxamide Using an analogous procedure to that described in Example 4, 6-chloropyrid-3-ylcarbonyl chloride was reacted with N-(5-amino-2-methylphenyl)quinoline-6-carboxamide in the presence of triethylamine. The reaction mixture was stirred at ambient temperature for 16 hours and then evaporated. The residue was purified by column chromatography on silica using increasingly polar mixtures of methylene chloride and methanol as eluent. There was thus obtained the title compound; Mass Spectrum: M–H$^-$ 415.

EXAMPLE 16

N-[2-methyl-5-(3-morpholinobenzamido)phenyl] thiophene-2-carboxamide

Thiophene-2-carbonyl chloride (0.069 g) was added to a stirred suspension of N-(3-amino-4-methylphenyl)-3-morpholinobenzamide (0.104 g), triethylamine (0.15 ml) and methylene chloride (20 ml) and the resultant mixture was stirred at ambient temperature for 4 hours. The organic phase was washed with water and with a saturated aqueous sodium bicarbonate solution, dried (MgSO$_4$) and evaporated. The residue was dissolved in methylene chloride (2 ml) and diethyl ether (20 ml) was added to give a precipitate which was isolated by filtration, washed with diethyl ether and dried. There was thus obtained the title compound (0.047 g); NMR Spectrum: (DMSOd$_6$) 2.18 (t, 3H), 3.18 (t, 4H), 3.76 (t, 4H), 7.14 (d, 1H), 7.20 (m, 2H), 7.38 (m, 2H), 7.41 (s, 1H), 7.58 (m, 1H), 7.78 (s, 1H), 7.82 (d, 1H), 7.98 (d, 1H), 9.93 (s, 1H), 10.13 (s, 1H); Mass Spectrum: M+H$^+$ 422.

The N-(3-amino4-methylphenyl)-3-morpholinobenzamide used as a starting material was prepared as follows:

A mixture of ethyl 3-bromobenzoate (1.92 ml), morpholine (1.25 ml), 2,2'-bis(diphenylphosphino)-1,1'-binaphthyl (0.336 g), sodium tert-butoxide (1.615 g) and tris (dibenzylideneacetone)dipalladium(0) (0.33 g) and toluene (25 ml) was stirred and heated to 90° C. for 18 hours under argon. The reaction mixture was allowed to cool to ambient temperature and extracted with 1N aqueous hydrochloric acid. The aqueous phase was basified with concentrated sodium hydroxide solution and extracted with ethyl acetate. The organic phase was dried (MgSO$_4$) and evaporated. The residual oil was purified by column chromatography on silica gel using a 47:3 mixture of methylene chloride and methanol as eluent. There was thus obtained N-(3-morpholinobenzoyl)morpholine (0.45 g).

A mixture of the material so obtained, SM sodium hydroxide solution (2.5 ml) and butanol (2 ml) was stirred and heated to 115° C. for 18 hours. The mixture was evaporated and the residue was acidified by the addition of 1N aqueous hydrochloric acid solution (12.5 ml). The resultant precipitate was isolated, washed with water and dried to give 3-morpholinobenzoic acid (0.15 g); NMR Spectrum: (DMSOd$_6$) 3.1 (t, 4H), 3.73 (t, 4H), 7.19 (d, 1H), 7.32 (d, 1H), 7.38 (t, 1H), 7.42 (s, 1H).

Oxalyl chloride (0.14 ml) was added to a solution of 3-morpholinobenzoic acid (0.28 g) in methylene chloride (10 ml) which contained DMF (2 drops). The reaction mixture was stirred for 18 hours at ambient temperature. The mixture was evaporated and azeotroped with toluene to give 3-morpholinobenzoyl chloride (0.3 g); Mass Spectrum: M+H$^+$ 222.

A solution of 3-morpholinobenzoyl chloride (0.24 g) in methylene chloride (5 ml) was added to a stirred mixture of 4-methyl-3-nitroaniline (0.15 g), pyridine (0.24 ml) and methylene chloride (10 ml). The reaction mixture was stirred at ambient temperature for 16 hours. The organic phase was washed with water and with a saturated aqueous sodium bicarbonate solution. The organic layer was dried (MgSO$_4$) and evaporated. The residual solid was triturated under diethyl ether and the resultant solid was isolated and dried to give N-(3-nitro-4-methylphenyl)-3-morpholinobenzamide (0.28 g); NMR Spectrum: (DMSOd$_6$) 3.2 (t, 4H), 3.3 (s, 3H), 3.78 (t, 4H), 7.19 (s, 1H), 7.4 (m, 2H), 7.47 (d, 2H). 8.0 (d, 1H), 8.83 (s, 1H), 10.23 (s, 1H).

10% Palladium-on-carbon (0.035 g) was added to a stirred solution in methanol (40 ml) of the nitro compound so obtained. (0.28 g) and the mixture was stirred at ambient temperature under 1 atmosphere pressure of hydrogen. After uptake of hydrogen had ceased, the catalyst was removed by filtration and the filtrate was evaporated to give N-(3-amino4-methylphenyl)-3-morpholinobenzamide; NMR Spectrum: (DMSOd$_6$) 2.0 (s, 3H), 3.19 (t, 4H), 3.78 (t, 4H), 4.8 (s, 2H), 6.8 (q, 2H), 7.08 (s, 1H), 7.1 (d, 1H), 7.34 (m, 2H), 7.4 (s, 1H), 9.8 (s, 1H); Mass Spectrum: M+H$^+$ 312.

EXAMPLE 17

2-chloro-N-[2-methyl-5-(2-morpholinopyrid-4-ylcarbonylamino)phenyl]pyridine4 carboxamide 2-Chloropyridine4-carbonyl chloride (0.143 g) was added to a stirred mixture of N-(3-amino4-methylphenyl)-2-morpholinopyridine4 carboxamide (0.211 g), triethylamine (0.164 g) and methylene chloride (10 ml) and the mixture was stirred at ambient temperature for 16 hours. The precipitate was isolated, washed with a saturated aqueous sodium bicarbonate solution and with methylene chloride and dried under vacuum at 40° C. There was thus obtained the title compound (0.276 g); NMR Spectrum: (DMSOd$_6$) 2.2 (s, 3H), 3.50–3.53 (m, 4H), 3.69–3.73 (m, 4H), 7.08 (d, 1H), 7.24 (d, 2H), 7.34 (d, 1H) 7.81 (s, 1H), 7.88 (d, 1H), 7.98 (s, 1H), 8.26 (d, 1H), 8.6 (d, 1H); Mass Spectrum M+H$^+$ 452 and 454.

The N-(3-amino4-methylphenyl)-2-morpholinopyridine 4carboxamide used as a starting material was prepared as follows:

Triethylamine (31.8 ml) was added to a stirred mixture of 4-methyl-3-nitroaniline (15.8 g), 2-chloropyridine4-carbonyl chloride (20 g) and methylene chloride (1 liter) and the resultant mixture was stirred at ambient temperature for 16 hours. The precipitate was isolated, washed with a saturated aqueous sodium bicarbonate solution and with methylene chloride and dried under vacuum at 40° C. There was thus obtained 2-chloro-N-(4-methyl-3-nitrophenyl) pyridine-4-carboxamide (10.2 g). The organic filtrate was washed with a saturated aqueous sodium bicarbonate solution, dried (MgSO$_4$) and evaporated. The residue was triturated under methylene chloride and the resultant solid was isolated and dried under vacuum at 40° C. There was thus obtained a second crop (8.13 g) of 2-chloro-N-(4-methyl-3-nitrophenyl)pyridine-4-carboxamide; NMR Spectrum: (DMSOd$_6$) 2.48 (s, 3H), 7.51 (d, 1H), 7.86 (m, 1H), 7.96 (m, 2H), 8.49 (m, 1H), 8.64 (m, 1H), 10.85 (s, 1H); Mass Spectrum: M+H$^+$ 292 and 294.

A mixture of the pyridine-4-carboxamide so produced and morpholine (250 ml) was stirred and heated to 100° C. for 18 hours. The mixture was poured into water (250 ml) and stirred for 10 minutes. Methylene chloride (30 ml) was added and the resultant mixture was stirred for 30 minutes. The resultant solid was isolated, washed with methylene chloride and dried in a vacuum oven at 40° C. for 18 hours. There was thus obtained N-(4-methyl-3-nitrophenyl)-2-morpholinopyridine-4-carboxamide (17.34 g); NMR Spectrum: (DMSOd$_6$) 2.48 (s, 3H), 3.52 (m, 4H), 3.71 (m, 4H), 7.1 (d, 1H), 7.25 (s, 1H), 7.49 (d, 1H) 7.97 (m, 1H), 8.29 (m, 1H), 8.49 (m, 1H), 10.62 (s, 1H), Mass Spectrum: M+H$^+$ 343.

A mixture of a portion (8.5 g) of the material so obtained, 5% palladium-on-carbon catalyst (0.85 g) and methanol (600 ml) was stirred under an atmosphere pressure of hydrogen gas for 18 hours. Methylene chloride (400 ml) was added and the reaction mixture was filtered through diatomaceous earth. The filtrate was evaporated to give N-(3-amino4-methylphenyl)-2-morpholinopyridine-4carboxamide (6.41 g); NMR Spectrum: (DMSOd$_6$) 2.01 (s, 3H), 3.52 (m, 4H), 3.73 (m, 4H), 4.83 (s, 2H), 6.78 (d, 1H). 6.84 (d, 1H) 7.04–7.08 (m, 2H), 7.2 (s, 1H), 8.24 (d, 1H), 9.95 (s, 1H); Mass Spectrum M+H$^+$ 313.

EXAMPLE 18

6-chloro-N-[2-methyl-5-(2-morpholinopyrid-4-ylcarbonylamino)phenyl]pyridine3-carboxamide Using an analogous procedure to that described in Example 17, 6-chloropyridine-3-carbonyl chloride was reacted with N-(3-amino4methylphenyl)-2-morpholinopyridine-4-carboxamide to give the title compound in 56% yield; NMR Spectrum: (DMSOd$_6$): 2.21 (s, 3.53 (m, 4H), 3.69–3.73 (m, 4H), 7.08 (d, 1H), 7.25 (d, 2H), 7.56 (d, 1H) 7.69 (d, 1H), 7.82 (d, 1H), 8.26 (d, 1H), 8.37 (d, 1H), 8.96 (d, 1H); Mass Spectrum M+H$^+$ 452 and 454.

EXAMPLE 19

Using an analogous procedure to that described in Example 17, the appropriate heteroarylcarbonyl chloride was reacted with the appropriate aniline to give the compounds described in Table II. Where required, heteroarylcarbonyl chlorides were prepared from the corresponding heteroarylcarboxylic acids by reaction with oxalyl chloride using an analogous procedure to that described in the first part of the portion of Example 4 which is concerned with the preparation of starting materials.

TABLE II

| No. | Heteroaryl | R | Note |
|---|---|---|---|
| 1 | 6-chloropyrid-3-yl | 3-trifluoromethyl | (a) |
| 2 | 6-chloropyrid-3-yl | 4-cyano | (b) |
| 3 | 2-chloropyrid-4-yl | 3-trifluoromethyl | (c) |
| 4 | 2-chloropyrid-4-yl | 4-cyano | (d) |

Notes
(a) The product gave the following data: NMR Spectrum: (DMSOd$_6$) 2.22 (s, 3H), 7.26 (d, 1H), 7.59 (d, 1H), 7.69 (d, 1H), 7.77 (t, 1H), 7.85 (s, 1H), 7.95 (d, 1H) 8.26 (m, 2H), 8.34 (m, 1H), 8.96 (s, 1H); Mass Spectrum: M + H$^+$ 434 and 436.
(b) The product gave the following data: NMR Spectrum: (DMSOd$_6$) 2.21 (s, 3H), 7.24 (d, 1H), 7.76 (d, 1H), 7.69 (d, 1H), 7.86 (s, 1H), 8.0 (d, 2H), 8.1 (d, 2H), 8.36 (m, 1H), 8.96 (s, 1H); Mass Spectrum: M + H$^+$ 391 and 393.

The N-(3-amino4-methylphenyl)4-cyanobenzamide used as a starting material prepared as follows:

Triethylamine (23 ml) was added to a suspension of 3-nitro-4-methylaniline (10 g), 4-cyanobenzoyl chloride (13.1 g), 4-dimethylaminopyridine (0.8 g) in methylene chloride (200 ml) which had been cooled to 0° C. The reaction mixture was allowed to warm to ambient temperature and was stirred for 5 hours. The mixture was partitioned between methylene chloride and 0.5N hydrochloric acid solution. The organic phase was dried (MgSO$_4$) and evaporated and the residue was triturated under isohexane. The solid was isolated and dried under vacuum at 55° C. There was thus obtained N-(3-nitro-4-methylphenyl)4-cyanobenzamide (18.3 g); NMR Spectrum: (DMSOd$_6$) 2.5 (s, 3H), 7.49 (d, 1H), 7.96 (m, 1H), 8.05 (d, 2H), 8.12 (d, 2H), 8.51 (d, 1H), 10.77 (s, 1H).

A solution of tin(II) chloride dihydrate (15.4 g) in concentrated hydrochloric acid (80 ml) was added to a suspension of N-(3-nitro-4-methylphenyl)-4-cyanobenzamide (6.39 g) in acetic acid (120 ml). The mixture was stirred and heated to reflux for 2 hours. The mixture was allowed to cool to ambient temperature and was basified by the addition of 2N sodium hydroxide solution. The precipitated solid was isolated and dried under vacuum at 55° C. to give N-(3-amino-4-methylphenyl)-4-cyanobenzamide (5.62 g); NMR Spectrum: (DMSOd$_6$) 2.01 (s, 3H), 4.85 (s, 2H), 6.8 (d, 1H), 6.86 (d, 1H), 7.11 (s, 1H), 7.96 (d, 2H), 8.06 (d, 2H), 10.11 (s, 1H).

(c) The product gave the following data: NMR Spectrum: (DMSOd$_6$) 2.21 (s, 3H), 7.26 (d, 1H), 7.59 (d, 1H), 7.77 (t, 1H), 7.83–7.90 (m, 2H), 7.92–7.99 (m, 2H), 8.20–8.29 (m, 2H), 8.61 (d, 1H), 10.38 (s, 2H); Mass Spectrum: M+H$^+$ 434 and 436.
(d) The product gave the following data: NMR Spectrum: (DMSOd$_6$) 2.21 (s, 3H), 7.26 (d, 1H), 7.58 (s, 1H), 7.87 (m, 2H), 8.0 (d, 3H), 8.09 (d, 2H), 8.61 (d, 1H), 10.27 (s, 1H), 10.48 (s, 1H); Mass Spectrum: M+H$^+$ 391 and 393.

EXAMPLE 20

N-[2-chloro-5-(4-cyanobenzamido)phenyl]pyridine-3-carboxamide

Using an analogous procedure to that described in Example 2, pyridine-3-carbonyl chloride was reacted with N-(3-amino-4-chlorophenyl)4-cyanobenzamide to give the title compound in 67% yield; NMR Spectrum: (DMSOd$_6$) 7.57 (d, 1H), 7.59 (m, 1H), 7.73 (d, 1H), 8.01 (d, 2H), 8.10 (m, 3H), 8.34 (d, 1H), 8.79 (d, 1H), 9.15 (d, 1H), 10.33 (s, 1H), 10.66 (s, 1H); Mass Spectrum M+H$^+$ 377.

EXAMPLE 21

6-(4-dimethylaminobutylamino)-N-[2-methyl-5-(2-morpholinopyrid-4-ylcarbonylamino)phenyl]pyridine-3-carboxamide A mixture of 4-dimethylaminobutylamine (5 ml) and 6-chloro-N-[2-methyl-5-morpholinopyrid-4-ylcarbonylamino)phenyl]pyridine-3-carboxamide (0.181 g) was stirred and heated to 100° C. for 16 hours. The mixture was poured into water (50 ml) and stirred for 20 minutes. The resultant solid was isolated, washed with diethyl ether and dried under vacuum at 40° C. There was thus obtained the title compound (0.17 g); NMR Spectrum: (DMSOd$_6$) 1.4–1.6 (m, 4H), 2.1 (s, 6H), 2.19 (s, 3H), 2.21 (m, 2H), 3.52 (m, 6H), 3.72 (m, 4H), 6.49 (d, 1H), 7.14 (m, 2H), 7.21 (m, 2H), 7.54 (d, 1H), 7.78 (s, 1H), 7,85 (d, 1H), 8.27 (d, 1H), 8.64 (s, 1H), 9.51 (s, 1H), 10.26 (s, 1H); Mass Spectrum M+H$^+$ 532.

EXAMPLE 22

Using an analogous procedure to that described in Example 21, the appropriate chloro-substituted heteroarylcarboxamide was reacted with the appropriate amine to give the compounds described in Table III.

TABLE III

Q$^1$—CONH—[2-Me-phenyl-5]—NHCO—Q$^2$

| No. | Q$^1$ | Q$^2$ | Note |
|---|---|---|---|
| 1 | 6-morpholinopyrid-3-yl | 3-trifluoromethylphenyl | (a) |
| 2 | 6-(2-aminoethylamino)-pyrid-3-yl | 3-trifluoromethylphenyl | (b) |
| 3 | 6-(3-morpholinopropyl-amino)pyrid-3-yl | 3-trifluoromethylphenyl | (c) |
| 4 | 6-morpholinopyrid-3-yl | 4-cyanophenyl | (d) |
| 5 | 6-(2-aminoethylamino)-pyrid-3-yl | 4-cyanophenyl | (e) |
| 6 | 6-(3-morpholinopropyl-amino)pyrid-3-yl | 4-cyanophenyl | (f) |
| 7 | 6-(1-benzylpiperidin-4-ylamino)pyrid-3-yl | 4-cyanophenyl | (g) |
| 8 | 6-(2-aminoethylamino)-pyrid-3-yl | 2-morpholinopyrid-4-yl | (h) |
| 9 | 6-(2-dimethylaminoethyl-amino)pyrid-3-yl | 2-morpholinopyrid-4-yl | (i) |
| 10 | 6-[N-(2-dimethylamino-ethyl)-N-methylamino]-pyrid-3-yl | 2-morpholinopyrid-4-yl | (j) |
| 11 | 6-(2-amino-2-methyl-propylamino)pyrid-3-yl | 2-morpholinopyrid-4-yl | (k) |
| 12 | 6-(2-diethylaminoethyl-amino)pyrid-3-yl | 2-morpholinopyrid-4-yl | (l) |
| 13 | 6-(3-aminopropylamino)-pyrid-3-yl | 2-morpholinopyrid-4-yl | (m) |
| 14 | 6-(3-dimethylamino-propylamino)pyrid-3-yl | 2-morpholinopyrid-4-yl | (n) |
| 15 | 6-(3-methylaminopropyl-amino)pyrid-3-yl | 2-morpholinopyrid-4-yl | (o) |
| 16 | 6-(3-morpholinopropyl-amino)pyrid-3-yl | 2-morpholinopyrid-4-yl | (p) |
| 17 | 6-[N-(3-dimethylamino-propyl)-N-methylamino]-pyrid-3-yl | 2-morpholinopyrid-4-yl | (q) |
| 18 | 6-[2-(N-methyl-pyrrolidin-2-yl)ethyl-amino]-pyrid-3-yl | 2-morpholinopyrid-4-yl | (r) |
| 19 | 6-(4-aminobutylamino)-pyrid-3-yl | 2-morpholinopyrid-4-yl | (s) |
| 20 | 6-(4-methylpiperazin-1-yl)pyrid-3-yl | 2-morpholinopyrid-4-yl | (t) |
| 21 | 6-(4-ethylpiperazin-1-yl)pyrid-3-yl | 2-morpholinopyrid-4-yl | (u) |
| 22 | 6-(4-methylhomo-piperazin-1-yl)pyrid-3-yl | 2-morpholinopyrid-4-yl | (v) |
| 23 | 6-[4-(2-hydroxyethyl)-piperazin-1-yl]pyrid-3-yl | 2-morpholinopyrid-4-yl | (w) |
| 24 | 6-(3-amino-2-hydroxy-propylamino)pyrid-3-yl | 2-morpholinopyrid-4-yl | (x) |
| 25 | 2-morpholinopyrid-4-yl | 3-trifluoromethylphenyl | (y) |
| 26 | 2-(2-aminoethylamino)-pyrid-4-yl | 3-trifluoromethylphenyl | (z) |
| 27 | 2-morpholinopyrid-4-yl | 4-cyanophenyl | (aa) |
| 28 | 2-(2-aminoethylamino)-pyrid-4-yl | 4-cyanophenyl | (bb) |
| 29 | 2-(4-methylpiperazin-1-yl)pyrid-4-yl | 2-morpholinopyrid-4-yl | (cc) |
| 30 | 2-[4-(2-hydroxyethyl)-piperazin-1-yl]-pyrid-4-yl | 2-morpholinopyrid-4-yl | (dd) |

Notes (a) The reactants were 6-chloro-N-[2-methyl-5-(3-trifluoromethyl-benzamido)phenyl]-pyridine-3-carboxamide [Example 19(1)] and morpholine. The product gave the following data: NMR Spectrum: (DMSOd$_6$) 2.05 (s, 3H), 3.57 (m, 4H), 3.69 (m, 4H), 6.9 (d, 1H), 7.23 (d, 1H), 7.58 (d, 1H), 7.76–7.82 (m, 2H), 7.94 (d, 1H), 8.1 (d, 1H), 8.21–8.28 (m, 2H), 9.67 (s, 1H), 10.42 (s, 1H); Mass Spectrum: M + H$^+$ 485.

(b) The reactants were 6-chloro-N-[2-methyl-5-(3-trifluoromethyl-benzamido)phenyl]-pyridine-3-carboxamide and ethylenediamine. The product gave the following data: NMR Spectrum: (DMSOd$_6$) 2.19 (s, 3H), 2.69 (m, 2H), 3.26 (m, 2H), 6.52 (d, 1H), 7.08–7.24 (m, 2H), 7.58 (d, 1H), 7.72–7.82 (m, 2H), 7.92 (t, 2H), 8.27 (m, 2H), 8.62 (s, 1H), 9.58 (s, 1H), 10.41 (s, 1H); Mass Spectrum: M + H$^+$ 458.

(c) The reactants were 6-chloro-N-[2-methyl-5-(3-trifluoromethyl-benzamido)phenyl]-pyridine-3-carboxamide and 3-morpholino-propylamine. The product gave the following data: NMR Spectrum: (DMSOd$_6$) 1.62–1.76 (m, 2H), 2.19 (s, 3H), 3.28–3.33 (m, 8H), 3.56 (m, 4H), 6.5 (d, 1H), 7.11 (t, 1H), 7.21 (d, 1H), 7.58 (d, 1H), 7.78 (m, 2H), 7.84–7.98 (m, 2H), 8.25 (m, 2H), 8.64 (s, 1H), 9.52 (s, 1H), 10.41 (s, 1H), Mass Spectrum: M + H$^+$ 542.

(d) The reactants were 6-chloro-N-[2-methyl-5-(4-cyano-benzamido)phenyl]pyridine-3-carboxamide [Example 19(2)] and morpholine. The product gave the following data: NMR Spectrum: (DMSOd$_6$) 2.2 (s, 3H), 3.48 (m, 4H), 3.69 (m, 4H), 6.84 (d, 1H), 7.12 (d, 1H), 7.68 (d, 1H), 7.82 (s, 1H), 7.99 (d, 2H), 8.09 (d, 3H), 8.75 (s, 1H), 9.67 (s, 1H), 10.43 (s, 1H); Mass Spectrum: M + H$^+$ 442.

(e) The reactants were 6-chloro-N-[2-methyl-5-(4-cyano-benzamido)phenyl]pyridine-3-carboxamide and ethylenediamine. The product gave the following data: NMR Spectrum: (DMSOd$_6$) 2.18 (s, 3H), 2.65–2.72 (m, 2H), 3.63–3.79 (m, 2H), 6.48 (d, 1H), 7.08 (t, 1H), 7.2 (m, 1H), 7.57 (d, 1H), 7.8 (s, 1H) 7.88–8.0 (m, 5H), 8.62 (s, 1H), 9.52 (s, 1H), 10.23 (s, 1H); Mass Spectrum: M + H$^+$ 415.

(f) The reactants were 6-chloro-N-[2-methyl-5-(4-cyano-benzamido)phenyl]pyridine-3-carboxamide and 3-morpholino-propylamine. The product gave the following data: NMR Spectrum: (DMSOd$_6$) 1.62–1.79 (m, 2H), 2.18 (s, 3H), 3.31 (m, 8H), 3.55 (m, 4H), 6.5 (d, 1H), 7.05 (t, 1H), 7.21 (d, 1H), 7.44 (s, 1H), 7.52 (d, 1H) 7.81 (s, 1H), 7.84–8.02 (m, 3H), 8.08 (s, 1H), 8.64 (s, 1H), 9.52 (s, 1H), 10.28 (s, 1H); Mass Spectrum: M + NH$_4^+$ 516.

(g) The reactants were 6-chloro-N-[2-methyl-5-(4-cyano-benzamido)phenyl]pyridine-3-carboxamide and 1-benzylpiperidin-4-ylamine. The product gave the following data: Mass Spectrum: M + NH$_4^+$ 562.

(h) The reactants were 6-chloro-N-[2-methyl-5-(2-morpholino-pyrid-4-ylcarbonylamino)phenyl]pyridine-3-carboxamide (Example 18) and ethylenediamine. The product gave the following data: Mass Spectrum: M + H$^+$ 476.

TABLE III-continued (i) The reactants were 6-chloro-N-[2-methyl-5-(2-morpholino-pyrid-4-ylcarbonylamino)phenyl]pyridine-3-carboxamide and 2-dimethylaminoethylamine. The product gave the following data: NMR Spectrum: (DMSOd$_6$) 2.17 (s, 6H), 2.19 (s, 3H), 2.41 (t, 2H), 3.32–3.42 (m, 2H), 3.5–3.57 (m, 4H), 3.71 (m, 4H), 6.54 (d, 1H), 7.0 (t, 1H), 7.1 (d, 1H), 7.24 (m, 2H), 7.58 (d, 1H), 7.77 (s, 1H), 7.85 (d, 1H), 8.26 (d, 1H), 8.64 (s, 1H), 9.51 (s, 1H), 10.25 (s, 1H); Mass Spectrum: M + H$^+$ 504.

(j) The reactants were 6-chloro-N-[2-methyl-5-(2-morpholino-pyrid-4-ylcarbonylamino)phenyl]pyridine-3-carboxamide and N-(2-dimethylaminoethyl)-N-methylamine. The product gave the following data: NMR Spectrum: (DMSOd$_6$) 2.18 (s, 6H), 2.19 (s, 3H), 2.42 (t, 2H), 3.07 (s, 3H), 3.50–3.55 (m, 4H), 3.69–3.73 (m, 6H), 6.67 (d, 1H), 7.11 (d, 1H), 7.22 (m, 2H), 7.58 (d, 1H), 7.79 (s, 1H), 8.01 (d, 1H), 8.26 (d, 1H), 8.72 (s, 1H), 9.57 (s, 1H), 10.26 (s, 1H); Mass Spectrum: M + H$^+$ 518.

(k) The reactants were 6-chloro-N-[2-methyl-5-(2-morpholino-pyrid-4-ylcarbonylamino)phenyl]pyridine-3-carboxamide and 2-amino-2-methylpropylamine. The product gave the following data: NMR Spectrum: (DMSOd$_6$) 1.02 (s, 6H), 2.19 (s, 3H), 3.23–3.3 (m, 2H), 3.54 (m, 4H), 3.71 (m, 4H), 6.61 (d, 1H), 7.0 (t, 1H), 7.1 (d, 1H), 7.24 (m, 2H), 7.58 (d, 1H), 7.78 (s, 1H), 7.85 (d, 1H), 8.26 (d, 1H), 8.61 (s, 1H), 9.51 (s, 1H), 10.25 (s, 1H); Mass Spectrum: M + H$^+$ 504.

(l) The reactants were 6-chloro-N-[2-methyl-5-(2-morpholino-pyrid-4-ylcarbonylamino)phenyl]pyridine-3-carboxamide and 2-diethylaminoethylamine. The product gave the following data: NMR Spectrum: (DMSOd$_6$) 0.96 (t, 6H), 2.19 (s, 3H), 2.53 (m, 6H), 3.35 (m, 2H), 3.52 (m, 4H), 3.71 (m, 4H), 6.49 (d, 1H), 6.96 (t, 1H), 7.08 (d, 1H), 7.22 (m, 2H), 7.54 (d, 1H), 7.78 (s, 1H), 7.85 (d, 1H), 8.26 (d, 1H), 8.64 (s, 1H), 9.52 (s, 1H), 10.26 (s, 1H); Mass Spectrum: M + H$^+$ 532.

(m) The reactants were 6-chloro-N-[2-methyl-5-(2-morpholino-pyrid-4-ylcarbonylamino)phenyl]pyridine-3-carboxamide and 1,3-diaminopropane. The product gave the following data: Mass Spectrum: M + H$^+$ 490.

(n) The reactants were 6-chloro-N-[2-methyl-5-(2-morpholino-pyrid-4-ylcarbonylamino)phenyl]pyridine-3-carboxamide and 3-dimethylaminopropylamine. The product gave the following data: NMR Spectrum: (DMSOd$_6$) 1.65 (m, 2H), 2.13 (s, 6H), 2.19 (s, 3H), 2.26 (t, 2H), 3.32–3.42 (m, 2H), 3.5–3.57 (m, 4H), 3.69–3.73 (m, 4H), 6.49 (d, 1H), 7.09–7.18 (m, 2H), 7.22 (m, 2H), 7.58 (d, 1H), 7.77 (s, 1H), 7.85 (d, 1H), 8.26 (d, 1H), 8.64 (s, 1H), 9.51 (s, 1H), 10.25 (s, 1H); Mass Spectrum: M + H$^+$ 518.

(o) The reactants were 6-chloro-N-[2-methyl-5-(2-morpholino-pyrid-4-ylcarbonylamino)phenyl]pyridine-3-carboxamide and 3-methylaminopropylamine. The product gave the following data: Mass Spectrum: M + H$^+$ 518.

(p) The reactants were 6-chloro-N-[2-methyl-5-(2-morpholino-pyrid-4-ylcarbonylamino)phenyl]pyridine-3-carboxamide and 3-morpholinopropylamine. The product gave the following data: NMR Spectrum: (DMSOd$_6$) 1.64–1.76 (m, 2H), 2.19 (s, 3H), 2.35 (m, 6H), 3.35 (m, 2H), 3.54 (m, 8H), 3.71 (m, 4H), 6.49 (d, 1H), 7.04–7.24 (m, 4H), 7.54 (d, 1H), 7.78 (s, 1H), 7.85 (d, 1H), 8.26 (d, 1H), 8.64 (s, 1H), 9.51 (s, 1H), 10.25 (s, 1H); Mass Spectrum: M + H$^+$ 560.

(q) The reactants were 6-chloro-N-[2-methyl-5-(2-morpholino-pyrid-4-ylcarbonylamino)phenyl]pyridine-3-carboxamide and N-(3-dimethylaminopropyl)-N-methylamine. The product gave the following data: NMR Spectrum: (DMSOd$_6$) 1.65 (m, 2H), 2.13 (s, 6H), 2.19 (s, 3H), 2.19–2.24 (m, 2H), 3.07 (s, 3H), 3.53 (m, 4H), 3.58 (t, 2H), 3.71 (m, 4H), 6.68 (d, 1H), 7.11 (d, 1H), 7.22 (m, 2H), 7.58 (d, 1H), 7.79 (s, 1H), 8.01 (d, 1H), 8.26 (d, 1H), 8.72 (s, 1H), 9.57 (s, 1H), 10.26 (s, 1H); Mass Spectrum: M + H$^+$ 532.

(r) The reactants were 6-chloro-N-[2-methyl-5-(2-morpholino-pyrid-4-ylcarbonylamino)phenyl]pyridine-3-carboxamide and 2-(N-methylpyrrolidin-2-yl)ethylamine. The product gave the following data: NMR Spectrum: (DMSOd$_6$) 1.38–1.48 (m, 2H), 1.56–1.65 (m, 2H), 1.8–1.96 (m, 2H), 2.0–2.3 (m, 2H), 2.19 (m, 7H), 3.27–3.3 (m, 2H), 3.52 (m, 4H), 3.72 (m, 4H), 6.49 (d, 1H), 7.14 (m, 2H), 7.22 (m, 2H), 7.54 (d, 1H), 7.78 (s, 1H), 7.85 (d, 1H), 8.26 (d, 1H), 8.64 (s, 1H), 9.51 (s, 1H), 10.26 (s, 1H); Mass Spectrum: M + H$^+$ 544.

(s) The reactants were 6-chloro-N-[2-methyl-5-(2-morpholinopyrid-4-ylcarbonylamino)phenyl]pyridine-3-carboxamide and 1,4-diaminobutane. The product gave the following data: Mass Spectrum: M + H$^+$ 504.

(t) The reactants were 6-chloro-N-[2-methyl-5-(2-morpholinopyrid-4-ylcarbonylamino)phenyl]pyridine-3-carboxamide and 1-methyl-piperazine. The product gave the following data: Mass Spectrum: M + H$^+$ 516.

(u) The reactants were 6-chloro-N-[2-methyl-5-(2-morpholino-pyrid-4-ylcarbonylamino)phenyl]pyridine-3-carboxamide and 1-ethylpiperazine. The product gave the following data: NMR Spectrum: (DMSOd$_6$) 1.05 (t, 3H), 2.2 (s, 3H), 2.3–2.4 (m, 2H), 2.4–2.5 (m, 4H), 3.5–3.55 (m, 4H), 3.55–3.65 (m, 4H), 3.7–3.75 (m, 4H), 6.9 (d, 1H), 7.1–7.15 (m, 1H), 7.2–7.25 (m, 2H), 7.55–7.6 (m, 1H), 7.8 (s, 1H), 8.0–8.1 (m, 1H), 8.25–8.3 (m, 1H), 8.75 (s, 1H), 9.65 (s, 1H), 10.3 (s, 1H); Mass Spectrum: M + H$^+$ 530.

(v) The reactants were 6-chloro-N-[2-methyl-5-(2-morpholino-pyrid-4-ylcarbonylamino)phenyl]pyridine-3-carboxamide and 1-methylhomopiperazine. The product gave the following data: Mass Spectrum: M + H$^+$ 530.

(w) The reactants were 6-chloro-N-[2-methyl-5-(2-morpholino-pyrid-4-ylcarbonylamino)phenyl]pyridine-3-carboxamide and 1-(2-hydroxyethyl)piperazine. The product gave the following data: Mass Spectrum: M + H$^+$ 546.

(x) The reactants were 6-chloro-N-[2-methyl-5-(2-morpholino-pyrid-4-ylcarbonylamino)phenyl]pyridine-3-carboxamide and 1,3-diamino-2-hydroxypropane. The product gave the following data: Mass Spectrum: M + H$^+$ 506.

(y) The reactants were 2-chloro-N-[2-methyl-5-(3-trifluoromethyl-benzamido)phenyl]-pyridine-4-carboxamide [Example 19(3)] and morpholine. The product gave the following data: NMR Spectrum: (DMSOd$_6$) 2.2 (s, 3H), 3.53 (m, 4H), 3.72 (m, 4H), 7.14 (d, 1H), 7.27 (d, 2H), 7.58 (d, 1H), 7.74–7.82 (m, 2H), 7.94 (d, 1H), 8.24–8.29 (m, 3H), 10.03 (s, 1H), 10.45 (s, 1H); Mass Spectrum: M + H$^+$ 485.

(z) The reactants were 2-chloro-N-[2-methyl-5-(3-trifluoromethyl-benzamido)phenyl]-pyridine-4-carboxamide and ethylenediamine. The product gave the following data: NMR Spectrum: (DMSOd$_6$) 2.2 (s, 3H), 2.69 (m, 2H), 3.26 (m, 2H), 6.76 (t, 1H), 6.92 (d, 2H), 7.25 (d, 1H), 7.61 (d, 1H), 7.77 (m, 2H), 7.95 (d, 1H), 8.09 (d, 1H), 8.26 (m, 2H), 9.91 (s, 1H), 10.45 (s, 1H); Mass Spectrum: M + H$^+$ 458.

(aa) The reactants were 2-chloro-N-[2-methyl-5-(4-cyano-benzamido)phenyl]pyridine-4-carboxamide [Example 19(4)] and morpholine. The product gave the following data: NMR Spectrum: (DMSOd$_6$) 2.2 (s, 3H), 3.53 (m, 4H), 3.74 (m, 4H), 7.12 (d, 1H), 7.27 (d, 2H), 7.58 (d, 1H), 7.82 (s, 1H), 8.01 (d, 2H), 8.1 (d, 2H), 8.25 (d, 1H), 10.06 (s, 1H), 10.43 (s, 1H); Mass Spectrum: M + H$^+$ 442.

(bb) The reactants were 2-chloro-N-[2-methyl-5-(4-cyano-benzamido)phenyl]pyridine-4-carboxamide and ethylenediamine. The product gave the following data: NMR Spectrum: (DMSOd$_6$) 2.19 (s, 3H), 2.7 (m, 2H), 3.26 (m, 2H), 6.8 (t, 1H), 6.92 (d, 2H), 7.2–7.3 (m, 1H), 7.58 (d, 1H), 7.81 (s, 1H), 7.9–8.0 (m, 3H), 8.08 (m, 2H), 9.92 (s, 1H), 10.25 (s, 1H); Mass Spectrum: M + H$^+$ 415.

(cc) The reactants were 2-chloro-N-[2-methyl-5-(4-cyano-benzamido)phenyl]pyridine-4-carboxamide and 1-methyl-piperazine. The product gave the following data: NMR Spectrum (DMSOd$_6$) 2.19 (s, 3H), 2.22 (s, 3H), 2.43 (m, 4H), 3.53 (m, 8H), 3.71 (m, 4H), 7.09 (m, 2H), 7.26 (m, 3H), 7.57 (d, 1H), 7.78 (s, 1H), 8.26 (m, 2H), 10.01 (s, 1H), 10.3 (s, 1H); Mass Spectrum: M + H$^+$ 516.

(dd) The reactants were 2-chloro-N-[2-methyl-5-(4-cyano-benzamido)phenyl]pyridine-4-carboxamide and 1-(2-hydroxy-ethyl)piperazine. The product gave the following data: NMR Spectrum: (DMSOd$_6$) 2.19 (s, 3H), 2.43 (t, 2H), 2.48–2.52 (m, TABLE III-continued 4H), 3.5–3.56 (m, 10H), 3.69–3.73 (m, 4H), 7.07–7.12 (m, 2H), 7.26 (m, 3H), 7.57 (d, 1H), 7.78 (s, 1H), 8.26 (m, 2H), 10.01 (s, 1H), 10.3 (s, 1H); Mass Spectrum: M + H⁺ 546.

EXAMPLE 23

N-[5-(4-trifluoromethylbenzamido)-2-methylphenyl] quinoline-6-carboxamide

Using an analogous procedure to that described in Example 4, 4-trifluoromethylbenzoyl chloride was reacted with N-(5-amino-2methylphenyl)-quinoline-6-carboxamide in the presence of triethylamine. The reaction mixture was stirred at ambient temperature for 18 hours and then evaporated. The residue was purified by column chromatography on silica using increasingly polar mixtures of methylene chloride and methanol as eluent. There was thus obtained the title compound in 52% yield; Mass Spectrum: M+H⁺ 450.

EXAMPLE 24

6-chloro-N-[5-(3-fluoro-5-morpholinobenzamido)-2-methylphenyl]pyridine-3-carboxamide Using an analogous procedure to that described in Example 2 except that the reaction mixture was heated to 100° C. for 4 hours, 6-chloropyridine-3-carbonyl chloride was reacted with N-(3-amino-4-methylphenyl)-3-fluoro-5-morpholinobenzamide to give the title compound in 74% yield; NMR Spectrum: (DMSOd₆): 2.2 (s, 3H), 3.18–3.22 (t, 4H), 3.75–3.85 (t, 4H), 6.9–7.0 (m, 1H), 7.1–7.15 (d, 1H), 7.2–7.3 (m, 2H), 7.55–7.6 (m, 1H) 7.65–7.7 (d, 1H), 7.8 (s, 1H), 8.3–8.4 (m, 1H), 8.95 (d, 1H), 10.15 (s, 1H), 10.17 (s, 1H); Mass Spectrum M+H⁺ 469 and 471.

The N-(3-amino4-methylphenyl)-3-fluoro-5-morpholinobenzamide used as a starting material was obtained as follows:

A solution of 3,5-difluorobenzoyl chloride (2.82 g) in methylene chloride (20 ml) was added to a stirred mixture of 4-methyl-3-nitroaniline (2.28 g), triethylamine (4.35 ml) and methylene chloride (80 ml). The resultant mixture was stirred at ambient temperature for 16 hours. The precipitate was isolated, washed with methylene chloride and dried. There was thus obtained N-(4-methyl-3-nitrophenyl)-3,5-difluorobenzamide; NMR Spectrum: (DMSOd₆) 2.43 (s, 3H), 7.43 (m, 2H), 7.63 (m, 2H), 7.95 (m, 2H), 8.43 (d, 1H), 10.42 (s, 1H); Mass Spectrum: M+H⁺ 293.

A mixture of a portion (1 g) of the material so obtained and morpholine (5 ml) was stirred and heated to 100° C. for 48 hours and then to 120° C. for 24 hours. The reaction mixture was cooled and poured into water (100 ml). The resultant solid was isolated, washed with water and dried. The material so obtained was purified by column chromatography on silica using a 1:1 mixture of isohexane and ethyl acetate as eluent. There was thus obtained N-(4methyl-3-nitrophenyl)-3-fluoro-5-morpholinobenzamide as a solid (0.53 g); NMR Spectrum: (DMSOd₆) 2.46 (s, 3H), 3.22 (t, 4H), 3.75 (t, 4H), 6.98 (m, 1H), 7.12 (d, 1H), 7.27 (s, 1H), 7.46 (d, 1H), 7.96 (m, 1H), 8.43 (d, 1H), 10.48 (s, 1H); Mass Spectrum: M+H⁺ 360.

A portion (0.483 g) of the compound so obtained was dissolved in ethyl acetate (40 ml) and hydrogenated over 10% palladium-on-carbon catalyst (0.6 g) under an atmosphere of hydrogen until the uptake of hydrogen ceased. The catalyst was removed by filtration and the filtrate was evaporated. The residue was triturated under diethyl ether (25 ml). The resultant solid was collected, washed with diethyl ether and dried. There was thus obtained the required starting material (0.341 g); NMR Spectrum: (DMSOd₆) 1.99 (s, 3H), 3.19 (t, 4H), 3.76 (t, 4H), 4.8 (s, 2H), 6.75 (d, 1H), 6.82 (d, 1H), 6.9 (d, 1H), 7.02 (s, 1H), 7.04 (d, 1H), 7.23 (s, 1H), 9.81 (s, 1H).

EXAMPLE 25

6-chloro-N-[2-methyl-5-(3-morpholino-5-trifluoromethylbenzamido)phenyl]pyridine-3-carboxamide Using an analogous procedure to that described in Example 2 except that the reaction mixture was heated to 100° C. for 2 hours, 6-chloropyridine-3-carbonyl chloride was reacted with N-(3-amino4-methylphenyl)-3-morpholino-5-trifluoromethylbenzamide. The reaction mixture was partitioned between ethyl acetate and water. The organic phase was dried over magnesium sulphate and evaporated. The residue was triturated under a mixture of isohexane and diethyl ether. There was thus obtained the title compound in 63% yield; NMR Spectrum: (DMSOd₆): 2.2 (s, 3H), 3.3 (m, 4H) 3.75 (t, 4H), 7.25 (d, 1H), 7.35 (s, 1H), 755–7.65 (m, 1H), 7.65 (s, 1H), 7.7–7.75 (m, 2H), 7.8 (d, 1H), 8.35–8.4 (m, 1H), 8.95 (d, 1H), 10.15 (s, 1H), 10.33 (s, 1H); Mass Spectrum M+H⁺ 519 and 521.

The N-(3-amino4methylphenyl)-3-morpholino-5-trifluoromethylbenzamide used as a starting material was obtained as follows:

Ethyl 3-morpholino-5-trifluoromethylbenzoate was prepared from ethyl 3-fluoro-5-trifluoromethylbenzoate by the method described by Brown et al., Tetrahedron Lett., 1999, 40, 1219. The material so obtained compound gave the following data:- NMR Spectrum: (CDCl₃) 1.36 (t, 3H), 3.19 (t, 4H), 3.81 (t, 4H), 4.34 (m, 2H), 7.22 (d, 1H), 7.76 (s, 1H).

A mixture of ethyl 3-morpholino-5-trifluoromethylbenzoate (0.67 g), 1N aqueous sodium hydroxide solution (3.3 ml) and ethanol (6 ml) was stirred and heated to reflux for 15 minutes and then left to stand for 16 hours. The ethanol was evaporated and the residue was dissolved in water (6 ml). Hydrochloric acid (1 M, 3.3 ml) was added and the resultant solid was isolated, washed with water and dried. There was thus obtained 3-morpholino-5-trifluoromethylbenzoic acid as a solid (0.464 g); NMR Spectrum: (DMSOd6) 3.25 (t, 4H), 3.73 (t, 4H), 7.4 (s, 1H), 7.53 (s, 1H), 7.65 (s, 1H), 13.3 (s, 1H).

A solution of 3-morpholino-5-trifluoromethylbenzoyl chloride (11.43 g; obtained by the reaction of the benzoic acid with oxalyl chloride using a conventional procedure) in methylene chloride (200 ml) was added to a stirred mixture of 4-methyl-3-nitroaniline (5.47 g), triethylamine (10 ml) and methylene chloride (200 ml). The resultant mixture was stirred at ambient temperature for 18 hours. The reaction mixture was washed with water and with a saturated aqueous sodium bicarbonate solution, dried (MgSO₄) and evaporated. The resultant solid was stirred with diethyl ether (300 ml) for 16 hours. The resultant solid was collected, washed with diethyl ether and dried. There was thus obtained N-(4-methyl-3-nitrophenyl)-3-morpholino-5-fluorobenzamide as a solid (10.4 g); NMR Spectrum: (CDCl₃) 2.58 (s, 3H), 3.22 (t, 4H), 3.83 (t, 4H), 7.21 (s, 2H), 7.32 (d, 1H), 7.41 (s, 1H), (s, 1H),7.82 (m, 1H), 8.02 (s, 1H), 8.23 (d, 1H).

The compound so obtained was dissolved in ethyl acetate (500 ml) and hydrogenated over 10% palladium-on-carbon catalyst (1.1 g) under 3 atmospheres pressure of hydrogen until the uptake of hydrogen ceased. The catalyst was removed by filtration and the filtrate was evaporated. The residue was triturated under ethyl acetate to give the required starting material (8.1 g); NMR Spectrum: (CDCl$_3$) 2.01 (s, 3H), 3.23 (t, 4H), 3.75 (t, 4H), 4.81 (s, 2H), 6.77 (m, 1H), 6.83 (d, 1H), 7.02 (d, 1H), 7.25 (s, 1H), 7.58 (s, 1H), 7.63 (s, 1H), 9.9 (s, 1H).

EXAMPLE 26

Using an analogous procedure to that described in Example 21, either 6-chloro-N-[5-(3-fluoro-5-morpholinobenzamido)-2-methylphenyl]pyridine-3carboxamide or 6chloro-N-[2-methyl-5-(3-morpholino-5-trifluoromethylbenzamido)phenyl]pyridine-3-carboxamide as appropriate was reacted with the appropriate amine to give the compounds described in Table IV.

TABLE IV

| No. | X | Y | Note |
|---|---|---|---|
| 1 | 2-dimethylaminoethylamino | fluoro | (a) |
| 2 | 2-dimethylaminoethylamino | trifluoromethyl | (b) |
| 3 | N-methyl-N-(2-methylaminoethyl)-amino | fluoro | (c) |
| 4 | N-methyl-N-(2-methylaminoethyl)-amino | trifluoromethyl | (d) |
| 5 | N-methyl-N-(2-dimethylamino-ethyl)amino | fluoro | (e) |
| 6 | N-methyl-N-(2-dimethylamino-ethyl)amino | trifluoromethyl | (f) |
| 7 | 2-amino-2-methylpropylamino | fluoro | (g) |
| 8 | 2-amino-2-methylpropylamino | trifluoromethyl | (h) |
| 9 | 3-aminopropylamino | fluoro | (i) |
| 10 | 3-aminopropylamino | trifluoromethyl | (j) |
| 11 | 3-dimethylaminopropylamino | trifluoromethyl | (k) |
| 12 | N-methyl-N-(3-methylamino-propyl)amino | trifluoromethyl | (l) |
| 13 | N-methyl-N-(3-dimethylamino-propyl)amino | fluoro | (m) |
| 14 | N-methyl-N-(3-dimethylamino-propyl)amino | trifluoromethyl | (n) |
| 15 | 4-aminobutylamino | fluoro | (o) |
| 16 | 4-aminobutylamino | trifluoromethyl | (p) |
| 17 | 4-dimethylaminobutylamino | trifluoromethyl | (q) |
| 18 | 4-methylpiperazin-1-yl | fluoro | (r) |
| 19 | 4-methylpiperazin-1-yl | trifluoromethyl | (s) |
| 20 | homopiperazin-1-yl | fluoro | (t) |
| 21 | homopiperazin-1-yl | trifluoromethyl | (u) |
| 22 | 3-morpholinopropylamino | fluoro | (v) |
| 23 | 3-morpholinopropylamino | trifluoromethyl | (w) |

Notes (a) The product gave the following data: NMR Spectrum: (DMSOd$_6$) 2.2–2.25 (m, 9H), 2.4–2.5 (m, 2H), 3.2–3.3 (m, 4H), 3.4–3.5 (m, 2H), 3.75–3.8 (m, 4H), 6.6 (d, 1H), 6.95–7.05 (m, 2H), 7.1–7.2 (m, 1H), 7.2–7.3 (m, 1H), 7.35 (s, 1H), 7.55–7.6 (m, 1H), 7.8 (s, 1H), 7.9–7.95 (m, 1H), 8.7 (s, 1H), 9.5 (s, 1H), 10.15 (s, 1H); Mass Spectrum: M + H$^+$ 521.

(b) The product gave the following data: NMR Spectrum: (DMSOd$_6$) 2.15–2.25 (m, 9H), 2.4–2.5 (m, 2H), 3.4–3.5 (m, 2H), 3.75–3.85 (m, 4H), 6.55–6.6 (m, 1H), 7.0–7.05 (m, 1H), 7.2–7.3 (m, 1H), 7.4 (s, 1H), 7.6–7.65 (m, 1H), 7.7 (s, 1H), 7.75 (s, 1H), 7.8 (s, 1H), 7.9–7.95 (m, 1H), 8.7 (s, 1H), 9.55 (s, 1H), 10.3 (s, 1H); Mass Spectrum: M + H$^+$ 571.

(c) The product gave the following data: Mass Spectrum: M + H$^+$ 521.

(d) The product gave the following data: Mass Spectrum: M + H$^+$ 571.

(e) The product gave the following data: NMR Spectrum: (DMSOd$_6$) 2.1–2.15 (m, 3H), 2.15–2.25 (m, 8H), 2.4–2.5 (m, 2H), 3.1 (s, 3H), 3.2–3.3 (m, 4H), 3.7–3.75 (m, 2H), 3.75–3.8 (m, 4H), 6.7 (d, 1H), 6.95–7.0 (m, 1H), 7.1–7.2 (m, 1H), 7.2–7.3 (m, 1H), 7.35 (s, 1H), 7.55–7.6 (m, 1H), 7.8 (s, 1H), 8.0–8.1 (m, 1H), 8.75 (m, 1H), 9.6 (s, 1H), 10.15 (s, 1H); Mass Spectrum: M + H$^+$ 535.

(f) The product gave the following data: NMR Spectrum: (DMSOd$_6$) 2.2–2.3 (m, 9H), 2.4–2.5 (m, 2H), 3.1 (s, 3H), 3.25–3.35 (m, 4H), 3.7–3.8 (m, 2H), 3.8–3.9 (m, 4H), 6.65–6.75 (m, 1H), 7.2–7.3 (m, 1H), 7.4 (s, 1H), 7.55–7.6 (m, 1H), 7.65 (s, 1H), 7.75 (s, 1H), 7.8 (s, 1H), 8.0–8.1 (m, 1H), 8.75 (s, 1H), 9.6 (s, 1H), 10.3 (s, 1H); Mass Spectrum: M + H$^+$ 585.

(g) The product gave the following data: NMR Spectrum: (DMSOd$_6$) 1.05 (s, 6H), 2.2 (s, 3H), 3.2–3.4 (m, 4H), 3.75–3.8 (m, 4H), 6.65 (d, 1H), 6.95–7.05 (m, 2H), 7.1–7.2 (m, 1H), 7.2–7.3 (m, 1H), 7.35 (s, 1H), 7.55–7.6 (m, 1H), 7.8 (s, 1H), 7.9–7.95 (m, 1H), 8.65 (s, 1H), 9.55 (s, 1H), 10.15 (s, 1H); Mass Spectrum: M + H$^+$ 521.

(h) The product gave the following data: Mass Spectrum: M + H$^+$ 571.

(i) The product gave the following data: Mass Spectrum: M + H$^+$ 507.

(j) The product gave the following data: Mass Spectrum: M + H$^+$ 557.

(k) The product gave the following data: NMR Spectrum: (DMSOd$_6$) 1.65–1.75 (m, 2H), 2.15 (s, 6H), 2.2 (s, 6H), 2.25–2.3 (m, 2H), 3.25–3.35 (m, 4H), 3.75–3.8 (m, 4H), 6.5–6.55 (m, 1H), 7.15–7.2 (m, 1H), 7.2–7.3 (m, 1H), 7.4 (s, 1H), 7.58–7.62 (m, 1H), 7.7 (s, 1H), 7.75 (s, 1H), 7.8 (s, 1H), 7.9–7.95 (m, 1H), 8.7 (s, 1H), 9.55 (s, 1H), 10.3 (s, 1H); Mass Spectrum: M + H$^+$ 585.

(l) The product gave the following data: Mass Spectrum: M + H$^+$ 585.

(m) The product gave the following data: NMR Spectrum: (DMSOd$_6$) 1.6–1.7 (m, 2H), 2.1 (s, 6H), 2.1–2.2 (m, 5H), 3.0 (s, 3H), 3.1–3.2 (m, 4H), 3.45–3.55 (m, 2H), 3.6–3.7 (m, 4H), 6.6–6.65 (m, 1H), 6.85–6.9 (m, 1H), 7.0–7.05 (m, 1H), 7.1–7.15 (m, 1H), 7.2 (s, 1H), 7.45–7.5 (m, 1H), 7.7 (s, 1H), 7.95–8.0 (m, 1H), 8.65 (s, 1H), 9.5 (s, 1H), 10.05 (s, 1H); Mass Spectrum: M + H$^+$ 549.

(n) The product gave the following data: NMR Spectrum: (DMSOd$_6$) 1.65–1.75 (m, 2H), 2.15 (s, 6H), 2.2–2.3 (m, 5H), 3.1 (s, 3H), 3.3–3.4 (m, 4H), 3.6–3.7 (m, 2H), 3.75–3.85 (m, 4H), 6.65–6.75 (m, 1H), 7.2–7.3 (m, 1H), 7.4 (s, 1H), 7.55–7.65 (m, 1H), 7.7 (s, 1H), 7.75 (s, 1H), 7.8 (s, 1H), 8.0–8.05 (m, 1H), 8.75 (s, 1H), 9.6 (s, 1H), 10.3 (s, 1H); Mass Spectrum: M + H$^+$ 599.

(o) The product gave the following data: Mass Spectrum: M + H$^+$ 521.

(p) The product gave the following data: Mass Spectrum: M + H$^+$ 571.

(q) The product gave the following data: Mass Spectrum: M + H$^+$ 599.

(r) The product gave the following data: NMR Spectrum: (DMSOd$_6$) 2.2–2.3 (m, 6H), 2.40–2.45 (m, 4H), 3.2–3.3 (m, 4H), 3.6–3.7 (m, 4H), 3.7–3.8 (m, 4H), 6.9 (d, 1H), 6.95–7.05 (m, 1H), 7.15–7.2 (m, 1H), 7.2–7.25 (m, 1H), 7.3 (s, 1H), 7.55–7.6 (m, 1H), 7.8 (s, 1H), 8.05–8.1 (m, 1H), 8.75 (s, 1H), 9.65 (s, 1H), 10.15 (s, 1H); Mass Spectrum: M + H$^+$ 533.

(s) The product gave the following data: Mass Spectrum: M + H$^+$ 583.

TABLE IV-continued

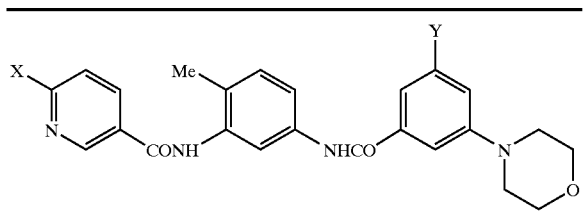

| No. | X | Y | Note |
|---|---|---|---|

(t) The product gave the following data: NMR Spectrum: (DMSOd$_6$) 1.75–1.85 (m, 2H), 2.2 (s, 3H), 2.65–2.75 (m, 4H), 2.85–2.9 (m, 2H), 3.2–3.3 (m, 5H), 3.7–3.85 (m, 9H), 6.75 (d, 1H), 6.95–7.0 (m, 1H), 7.1–7.2 (m, 1H), 7.2–7.3 (m, 1H), 7.35 (s, 1H), 7.55–7.6 (m, 1H), 7.8 (s, 1H), 8.0–8.1 (m, 1H), 9.6 (s, 1H), 10.15 (s, 1H); Mass Spectrum: M + H$^+$ 533.

(u) The product gave the following data: Mass Spectrum: M + H$^+$ 583.

(v) The product gave the following data: NMR Spectrum: (DMSOd$_6$) 1.7–1.8 (m, 2H), 2.2 (s, 3H), 2.3–2.4 (m, 6H), 3.2–3.3 (m, 4H), 3.3–3.4 (m, 2H), 3.5–3.6 (m, 4H), 3.75–3.8 (m, 4H), 6.5–6.55 (m, 1H), 6.95–7.0 (m, 1H), 7.1–7.2 (m, 2H), 7.2–7.25 (m, 1H), 7.3 (s, 1H), 7.55–7.6 (m, 1H), 7.8 (s, 1H), 7.9–7.95 (m, 1H), 8.7 (s, 1H), 9.55 (s, 1H), 10.2 (s, 1H); Mass Spectrum: M + H$^+$ 577.

(w) The product gave the following data: NMR Spectrum: (DMSOd$_6$) 1.7–1.8 (m, 2H), 2.2 (s, 3H), 2.3–2.45 (m, 7H), 3.5–3.65 (m, 4H), 3.75–3.85 (m, 4H), 6.5–6.55 (m, 1H), 7.15–7.2 (m, 1H), 7.2–7.3 (m, 1H), 7.4 (s, 1H), 7.55–7.6 (m, 1H), 7.7 (s, 1H), 7.75 (s, 1H), 7.8 (s, 1H), 7.9–7.95 (m, 1H), 8.65 (s, 1H), 9.55 (s, 1H), 10.3 (s, 1H); Mass Spectrum: M + H$^+$ 627.

EXAMPLE 27

6-chloro-N-[2-chloro-5-(3-fluoro-5-morpholinobenzamido)phenyl]pyridine-3-carboxamide Using an analogous procedure to that described in Example 2, 6-chloropyridine-3-carbonyl chloride was reacted with N-(3-amino-4-chlorophenyl)-3-fluoro-5-morpholinobenzamide to give the title compound in 48% yield; NMR Spectrum: (DMSOd$_6$) 3.23 (m, 4H0m 3.74 (m, 4H0, 6.97 (d, 1H), 7.12 (d, 1H, 7.26 (s, 1H), 7.54 (d, 1H), 7.71 (d, 2H), 8.07 (s, 1H), 8.35 (d, 1H), 8.95 (s, 1H), 10.37 (m, 2H); Mass Spectrum: M+H$^+$487.

The N-(3-amino-4-chlorophenyl)-3-fluoro-5-morpholinobenzamide used as a starting material was obtained as follows:

3,5-Diflurobenzoyl chloride (12.6 ml) was added slowly to a stirred mixture of 2,4-diaminochlorobenzene (14.3 g), triethylmine (15.3 ml) and methylene chloride (150 ml) and the result mixtrue was stirred at ambient temperature for 2 hours. The mixture was evaporated and the residue was triturated under water. The resultatnt solid was isolated, washed with a saturated aqueos sodium bicarbonate solution and dried under vacuum. The material so obtained was dissolved in a minimum amount of ethyl acetate and precipitated by the addition of isohexane. The resultatn solid was isolated, washed with one equivalent of dilute aqueous hydrochloric acid and dried under vacuum. There was thus obtained N-(3-amino-4-cholorophenyl)-3,5-difluorobenzamide (26.83 g); NMR Spectrum: (DMSOd$_6$) 5.37 (br s, 2H), 6.88 (d, 1H), 7.13 (d, 1H), 7.32 (d, 1H), 7.46 (m, 1H), 7.63 (d, 2H), 10.16 (s, 1H); Mass Specturm: M+H$^+$283.

A mixture of a portion (10 g) of the material so obtained and morpholine (36 ml) was stirred and heated to 100° C. for 15 days. The mixture was poured into a mixture of ice and water and the resultant solid was isolated and washed with water. The solid wqas dissolved in ethyl acetate and the solution was dried over magnesium sulphate. The filtered solution was reduced in volume by evaporation under vacuum until precipitation was observed. A small quantity of diethyl ether was added followed by ioshexane. The resultant solid was isolated and dried under vacuum to give N-(3-amino-4-chlorophenyl)-3-fluoro-5-morpholinobenzamide (11.23 g); NMR Specturm: (DMSOd$_6$) 3.21 (m, 4H), 3.73 (m, 4H),

EXAMPLE 28

6-chloro-N-[2-chloro-5-(2-morpholinopyrid-4-ylcarbonylamino)phenyl]pyridine-3-carboxamide Using an analogous procedure to that described in Example 2 except that the reaction mixture was heated to 80° C. for 16 hours, 6-chloropyridine-3-carbonyl chloride was reacted with N-(3-amino4-chlorophenyl)-2-morpholinopyridine4-carboxamide. The reaction mixture was evaporated and the residue was triturated under water. The resultant solid was isolated, washed with a saturated aqueous sodium bicarbonate solution and dried in a vacuum oven. The material so obtained was purified by column chromatography on an ion exchange column (isolute CBA column from International Sorbent Technology Limited, Hengoed, Mid-Glamorgan, UK) using methanol as eluent. There was thus obtained the title compound (0.493 g) in 58% yield; NMR Spectrum: (DMSOd$_6$) 3.51 (m, 4H), 3.71 (m, 4H), 7.09 (d, 1H), 7.23 (s, 1H), 7.55 (d, 1H), 7.71 (d, 2H), 8.06 (s, 1H), 8.27 (d, 1H), 8.35 (d, 1H), 8.96 (s, 1H), 10.39 (s, 1H), 10.49 (s, 1H); Mass Spectrum: M+H$^+$ 472.

The N-(3-amino4-chlorophenyl)-2-morpholinopyridine-4carboxamide used as a starting material was obtained as follows:

A solution of 2-chloropyridine4carbonyl chloride [obtained by the reaction of oxalyl chloride (2.1 ml) and 2-chloropyridine-4-carboxylic acid (3.15 g) in a mixture of methylene chloride (50 ml) and DMF (a few drops)] in methylene chloride (10 ml) was added slowly to a stirred mixture of 2,4-diaminochlorobenzene (2.85 g) and triethylamine (7 ml) and the reaction mixture was stirred at ambient temperature for 16 hours. The reaction mixture was washed with a saturated aqueous sodium bicarbonate solution, dried over magnesium sulphate and evaporated. The residue was triturated under methanol and there was thus obtained N-[2-chloro-5-(2-chloropyrid-4-ylcarbonylamino)phenyl]-2-chloropyridine-4-carboxamide (1.46 g); NMR Spectrum: (DMSOd$_6$) 7.56 (d, 1H), 7.72 (d, 1H), 7.87 (m, 2H), 7.98 (s, 2H), 8.10 (s, 1H), 8.63 (t, 2H); Mass Spectrum: M+H$^+$ 421.

The filtrate from the trituration was evaporated and the residue was purified by column chromatography on an ion exchange column (isolute SCX column from International Sorbent Technology Limited, Hengoed, Mid-Glamorgan, UK) using a 99:1 mixture of methanol and a saturated aqueous ammonium hydroxide solution as eluent. There was thus obtained N-(3-amino-4-chlorophenyl)-2-chloropyridine-4-carboxamide (1.65 g); NMR Spectrum: (DMSOd$_6$) 5.41 (br s, 2H), 6.87 (d, 1H), 7.15 (d, 1H), 7.33 (s, 1H), 7.82 (d, 1H), 7.94 (s, 1H), 8.58 (d, 1H), 10.37 (s, 1H); Mass Spectrum: M+H$^+$ 282.

A mixture of N-(3-amino-4-chlorophenyl)-2-chloropyridine-4-carboxamide (1.53 g) and morpholine (10 ml) was stirred and heated to 120° C. for 16 hours. The reaction mixture was poured into a mixture of ice and water and the resultant solid was isolated, washed with water and dried in a vacuum oven. There was thus obtained the required starting material as a solid (1.62 g); NMR Spectrum: (DMSOd$_6$) 3.51 (m, 4H), 3.72 (m, 4H), 5.36 (br s, 2H), 6.86 (d, 1H), 7.08 (d, 1H), 7.15 (d, 1H), 7.20 (s, 1H), 7.33 (s, 1H), 8.25 (d, 1H), 10.13 (s, 1H); Mass Spectrum: M+H$^+$ 333.

EXAMPLE 29

N-[2-chloro-5-(2-morpholinopyrid-4-ylcarbonylamino)phenyl]-6-[N-(3-dimethylaminopropyl)-N-methylamino]pyridine-3-carboxamide Using an analogous procedure to that described in Example 21, 6-chloro-N-[2-chloro-5-(2-morpholinopyrid-4-ylcarbonylamino)phenyl]pyridine-3-carboxamide was reacted with N-(3-dimethylaminopropyl)-N-methylamine to give the title compound in 73% yield; NMR Spectrum: (DMSOd$_6$) 1.67 (m, 2H), 2.12 (s, 6H), 2.21 (t, 2H), 3.07 (s, 3H), 3.51 (m, 4H), 3.58 (m, 2H), 3.71 (m, 4H), 6.69 (d, 1H), 7.1 (d, 1H), 7.23 (s, 1H), 7.5 (d, 1H), 8.04 (m, 2H), 8.28 (d, 1H), 8.72 (s, 1H), 9.7 (s, 1H), 10.44 (s, 1H); Mass Spectrum: M+H$^+$ 552 and 554.

EXAMPLE 30

N-[2-chloro-5-(2-morpholinopyrid-4-ylcarbonylamino)phenyl]-6-(4dimethylaminobutylamino)pyridine-3-carboxamide Using an analogous procedure to that described in Example 21, 6-chloro-N-[2-chloro-5-(2morpholinopyrid-4-ylcarbonylamino)phenyl]pyridine-3-carboxamide was reacted with 4-dimethylaminobutylamine to give the title compound in 61% yield; NMR Spectrum: (DMSOd$_6$) 1.49 (m, 4H), 2.09 (s, 6H), 2.19 (t, 2H), 3.51 (m, 4H), 3.71 (m, 4H), 6.49 (d, 1H), 7.1 (d, 1H), 7.23 (m, 2H), 7.5 (d, 1H), 7.68 (d, 1H), 7.89 (d, 1H), 8.06 (s, 1H), 8.64 (s, 1H), 9.64 (s, 1H), 10.44 (s, 1H); Mass Spectrum: M+H$^+$ 552 and 554.

EXAMPLE 31

2-chloro-N-[2-chloro-5-(2-morpholinopyrid-4-ylcarbonylamino)phenyl]pyridine-4-carboxamide Using an analogous procedure to that described in Example 2, except that the reaction mixture was heated to 80° C. for 5 hours, 2-chloropyridine-4-carbonyl chloride was reacted with N-(3-amino-4-chlorophenyl)-2-morpholinopyridine-4-carboxamide to give the title compound in 95% yield; NMR Spectrum: (DMSOd6) 3.53 (m, 4H), 3.75 (m, 4H), 7.11 (d, 1H), 7.27 (s, 1H), 7.56 (d, 1H), 7.73 (d, l1H), 7.88 (d, 1H), 7.98 (s, 1H), 8.06 (s, 1H), 8.26 (d, 1H), 8.64 (d, 1H), 10.53 (m, 2H); Mass Spectrum: M+H$^+$ 472.

EXAMPLE 32

N-[2-chloro-5-(2-morpholinopyrid-4-ylcarbonylamino)phenyl]-2-N-(3-dimethylaminopropyl)-N-methylamino]pyridine-4-carboxamide Using an analogous procedure to that described in Example 21, 2-chloro-N-[2-chloro-5-(2-morpholinopyrid-4-ylcarbonylamino)phenyl]pyridine-4-carboxamide was reacted with N-(3-dimethylaminopropyl)-N-methylamine to give the title compound in 46% yield; NMR Spectrum: (DMSOd$_6$) 1.67 (m, 2H), 2.11 (s, 6H), 2.21 (m, 2H), 3.04 (s, 3H), 3.51 (m, 6H), 3.71 (m, 4H), 6.97 (d, 1H), 7.09 (m, 2H), 7.23 (s, 1H), 7.54 (d, 1H), 7.71 (d, 1H), 8.04 (s, 1H), 8.20 (d, 1H), 8.27 (d, 1H), 10.13 (s, 1H), 10.47 (s, 1H); Mass Spectrum: M+H$^{30}$ 552.

EXAMPLE 33

2-[N-(2-dimethylaminoethyl)-N-methylamino]-N-[2-methyl-5-(2-morpholinopyrid-4-ylcarbonylamino)phenyl]pyridine-4-carboxamide Using an analogous procedure to that described in Example 21, 2-chloro-N-[2-methyl-5-(2-morpholinopyrid-4-ylcarbonylamino)phenyl]pyridine-4-carboxamide was reacted with N-(2-dimethylaminoethyl)-N-methylamine to give the title compound in 44% yield; NMR Spectrum: (DMSOd6) 2.17 (s, 6H), 2.19 (s, 31), 2.4 (t, 2H), 3.05 (s, 3H), 3.5–3.54 (m, 4H) 3.65–3.72 (m, 6H), 6.75 (s, 1H), 6.94 (d, 1H), 7.02 (s, 1H), 7.1 (d, 1H), 7.24 (d, 2H), 7.58 (d, 1H), 7.78 (s, 1H), 8.19 (d, 1H), 8.26 (d, 1H), 9.96 (s, 1H), 10.28 (s, 1H); Mass Spectrum: M+H$^+$ 518.

EXAMPLE 34

2-[N-(3-dimethylaminopropyl)-N-methylamino]-N-[2-methyl-5-(2-morpholinopyrid-4-ylcarbonylamino)phenyl]pyridine-4-carboxamide Using an analogous procedure to that described in Example 21, 2-chloro-N-[2-methyl-5-(2-morpholinopyrid-4-ylcarbonylamino)phenyl]pyridine-4-carboxamide was reacted with N-(3-dimethylaminopropyl)-N-methylamine to give the title compound in 56% yield; Mass Spectrum: M+H$^+$ 532.

EXAMPLE 35

N-[2-chloro-5-(2-morpholinopyrid-4-ylcarbonylamino)phenyl]-2-morpholinopyridine-4-carboxamide Using an analogous procedure to that described in Example 21, N-[2-chloro-5-(2-chloropyrid-4-ylcarbonylamino)phenyl]-2-chloropyridine-4-carboxamide was reacted with morpholine to give the title compound in 84% yield; NMR Spectrum: (DMSOd$_6$) 3.52 (m, 8H), 3.73 (m, 8H), 7.12 (m, 2H), 7.26 (d, 2H), 7.55 (d, 1H), 7.73 (d, 1H), 8.3 (m, 2H), 10.21 (s, 1H), 10.48 (s, 1H); Mass Spectrum: M+H$^+$ 523.

EXAMPLE 36

N-[2-chloro-5-(2-piperidinopyrid-4-ylcarbonylamino)phenyl]-2-piperidinopyridine-4-carboxamide Using an analogous procedure to that described in Example 21, N-[2-chloro-5-(2-chloropyrid-4-ylcarbonylamino)phenyl]-2-chloropyridine-4-carboxamide was reacted with piperidine to give the title compound in 96% yield; NMR Spectrum: (DMSOd$_6$) 1.6 (m, 12H), 3.58 (m, 8H), 7.01 (m, 2H), 7.24 (d, 2H), 7.54 (d, 1H), 7.73 (d, 1H), (m, 2H), 10.09 (br s, 1H), 10.44 (br s, 1H); Mass Spectrum: M+H$^+$ 519.

EXAMPLE 37

N-[2-chloro-5-(2-morpholinopyrid-4-ylcarbonylamino)phenyl]-2-(4-methylpiperazin-1-yl)pyridine-4-carboxamide Using an analogous procedure to that described in Example 21, 2-chloro-N-[2chloro-5-(2-morpholinopyrid-4- ylcarbonylamino)phenyl]pyridine-4-carboxamide was reacted with N-methylpiperazine to give the title compound in 69% yield; NMR Spectrum: (DMSOd$_6$) 2.21 (s, 3H), 2.4 (m, 4H), 3.53 (m, 8H), 3.71 (m, 4H), 7.09 (m, 2H), 7.25 (d, 2H), 7.53 (d, 1H), 7.71 (d, 1H), 8.02 (s, 1H), 8.26 (t, 1H), 10.19 (s, 1H), 10.48 (s, 1H); Mass Spectrum: M+H$^+$ 536.

EXAMPLE 38

N-[2-chloro-5-(2-morpholinopyrid-4-ylcarbonylamino)phenyl]-2-[4-(2-hydroxyethyl)piperazin-1-yl]pyridine-4-carboxamide Using an analogous procedure to that described in Example 21, 2-chloro-N-[2-chloro-5-(2-morpholinopyrid-4-ylcarbonylamino)phenyl]pyridine-4-carboxamide was reacted with N-(2-hydroxyethyl)piperazine to give the title compound in 62% yield; NMR Spectrum: (DMSOd$_6$) 2.45 (m, 8H), 3.53 (m, 8H), 3.71 (m, 4H), 4.4 (t, 1H), 7.07 (m, 2H) 7,25 (d, 2H), 7.54 (d, 1H), 7.71 (d, 1H), 8.02 (s, 1H), 8.26 (t, 2H), 10.19 (s, 1H), 10.47 (s, 1H); Mass Spectrum: M+H$^+$ 566.

EXAMPLE 39

N-[5-(3-dimethylaminobenzamido)-2-methylphenyl]quinoline-6-carboxamide

Diisopropylethylamine (0.174 ml) was added to a stirred mixture of 3-morpholinobenzoic acid (0.104 g), N-(5-amino-2-methylphenyl)quinoline-6carboxamide (0.14 g), 2-(7-azabenzotriazol-1-yl)-1,1,3,3-tetramethyluronium hexafluorophosphate(V) (0.23 g) and DMF (1 ml) and the resultant mixture was stirred at ambient temperature for 16 hours. The reaction mixture was poured into water and the resultant solid was isolated, washed with a saturated aqueous sodium bicarbonate solution and dried in a vacuum oven. There was thus obtained the title compound (0.216 g); NMR Spectrum: (DMSOd6) 2.25 (s, 3H), 3.18 (m, 4H), 3.75 (m, 4H), 7.14 (d, 1H), 7.25 (d, 1H), 7.36 (m, 2H), 7.44 (s, 1H), 7.62 (m, 2H), 7.86 (s, 1H), 8.13 (d, 1H), 8.28 (d, 1H), 8.52 (d, 1H), 8.65 (s, 1H), 9.0 (s, 1H), 10.14 (m, 2H); Mass Spectrum: M+H$^+$ 467.

EXAMPLE 40

Pharmaceutical Compositions

The following illustrate representative pharmaceutical dosage forms of the invention as defined herein (the active ingredient being termed "Compound X"), for therapeutic or prophylactic use in humans:

| (a) Tablet 1 | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |

| | |
|---|---|
| -continued | |
| 1-Dodecylazacycloheptan-2-one | 50 μl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. An amide derivative of the Formula I

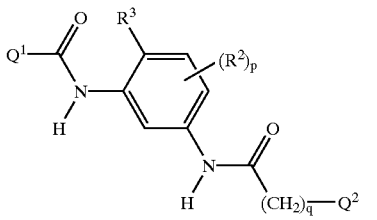

wherein $R^3$ is (1–6C)alkyl or halogeno;

$Q^1$ is an aromatic 6-membered nitrogen containing heterocyclic ring, which is optionally substituted with 1, 2, 3 or 4 substituents selected from hydroxy, halogeno, trifluoromethyl, cyano, mercapto, nitro, amino, carboxy, carbamoyl, formyl, (1–6C)alkyl, (2–6C)alkenyl, (2–6C)akynyl, (1–6C)alkoxy, (1–3C)alkylenedioxy, (1–6C)alkylthio, (1–6C)alkylsulphinyl, (1–6C)alkgylsulphonyl, (1–6C)alkylamino, di-[(1–6C)alkyl]amino, (1–6C)alkoxycarbonyl, N-1–6C) alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarmoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(1–6C)akyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(-6C)alkoxy, heteroarylamino, N-(1–6C)alkyl-heteroarylamino, hetaroayl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-(1–6C)aklyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C)alkanoylamino, and wherein any of the substituents on $Q^1$ defined hereinbefore which contain a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino, di-[(1–6C)alkyl] amino and heterocyclyl;

and wherein any aryl, heteroaryl or heterocyclyl group in a substituent on $Q^1$ may optionally bear 1 or 2 substituents selected from hydroxy, halogeno, (1–6C)alkyl, (1–6C)alkoxy, carboxy, (1–6C)alkoxycarbonyl, N-(1–6C)alkylcarbamoyl, N,N-di-[(1–6C)alkyl) carbamoyl, (2–6C)alkanoyl, amino, (1–6C)alkylamino, di-[(1–6C)alkyl]amino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl; $R^2$ is hydroxy, halogeno, trifluoromethyl, cyano, mercapto, nitro, amino, carboxy, (1–6C)alkoxycarbonyl, (1–6C)alkyl, (2–6C)alkenyl, (2–6C)alkynyl, (1–6C)alkoxy, (1–6C)alklamino or di-[(1–6C)alkyl]amino;

is 0, 1 or 2;

q is 0, 1, 2, 3 or 4; and

Q2 is phenyl which is optionally substituted with 1, 2, 3 or 4 substituents selected from hydroxy, halogeno, trifluoromethyl, cyano, mercapto, nitro, amino, carboxy, carbamoyl, formyl, (1–6C)alkyl, (2–6C)alkenyl, (2–6C)alkynyl, (1–6C)alkoxy, (1–3C)alkylenedioxy, (1–6C)alkylthio, (1–6C)alkylsulphinyl (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (1–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl di-[(1–6C)alkyl]amino-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl di-[(1–6C)alkyl]amino-(2–6C)alkylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkly]amino-(2–6C)alkanoylamino, aryl, aryl-(1–6C)alkyl, aryl-(1–6C)alkoxy, aryloxy, arylamino, N-(1–6C)alkyl-arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryl, heteroaryl-(1–6C)alkyl, heteroaryloxy, heteroaryl-(1–6C)alkoxy, heteroarylamino, N-(1–6C)alkyl-heteroarylamino, heteroaryl-(1–6C)alkylamino, N(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyl, heterocyclyl-(1–6C)alkyl, heterocyclyloxy, heterocyclyl-(1–6C)alkoxy, heterocyclylamino, N-(1–6C)alkyl-heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphatnoyl and heterocyclyl-(2–6C)alkanoylamino, and wherein any of the substituents on $Q^2$ defined hereinbefore which contain a $CH_2$ group which is attached to 2 carbon atoms or a $CH_3$ group wich is attached to a carbon atom may optionally bear on each said $CH_2$ or $CH_3$ group a substituent selected from hydroxy, amino, (1–6C)alkoxy, (1–6C)alkylamino, di-[(1–6C)alkyl]amino and heterocyclyl; and wherein any aryl, heteroaryl or heterocyclyl group in a substituent on Q2 may optionally bear 1 or 2 substituents selected from hydroxy, halogeno, (1–6C)alkyl, (1–6C)alkoxy, carboxy, (1–6C)alkoxycarbonyl, N-(1–6C)alkylcarbomyl, N,N-di-[(1–6C)alkyl]carbamoyl, (2–6C)alkanoyl, amino, (1–6C)alkylamino, di-[(1–6C)alkyl]amino, halogeno-(1–6C)alkyl, hydroxy-(1–6C)alkly, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, aryl and aryl-(1–6C)alkyl;

or a pharmaceutically-acceptable salt or in-vivo-cleavable ester thereof.

2. An amide derivative of the Formula I according to claim 1 wherein $R^3$ is methyl, ethyl, chloro or bromo;

$Q^1$ is pyridyl, pyridazinyl, pyrimidinyl or pyrazinyl which optionally bears 1 or 2 substituents selected from hydroxy, fluoro, chloro, trifluoromethyl, cyano, methyl, ethyl, methoxy and ethoxy;

p is 0;

q is 0; and $Q^2$ is phenyl which bears 1 or 2 substituents selected from hydroxy, fluoro, chloro, trifluoromethyl, cyano, amino, methyl, ethyl, methoxy, ethoxy, methylenedioxy, methylamino, ethylamino, dimethylamino, diethylamino, acetyl, propionyl, chloromethyl, methoxymethyl, 2-methoxyethyl, methylaminomethyl, ethylaminomethyl, dimethylaminomethyl, diethylaminomethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, cyanomethoxy, carboxymethoxy, methoxycarbonylmethoxy, ethoxycarbonylmethoxy, tert-butoxycarbonylmethoxy, 2-aminoethoxy, 3-aminopropoxy, 2-methylaminoethoxy, 2-ethylaminoetoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-chloroethylamino, 2-hydroxyethylamino, 2-methoxyethylamino, 2-ethoxyethylamino, 2-aminoethylamino, 2-methylaminoethylamino, 2-ethylaminoethylamino, 2-dimethylaminoethylamino, 2-diethylaminoethylamino, N-(2-chloroethyl)-N-methylamino, N-(2-hydroxyethyl)-N-methylamino, N-(2-methoxyethyl)-N-methylamino, N-(2-ethoxyethyl)-N-methylamino, N-(2-aminoethyl)-N-metylamino, N-(2-methylaminoethyl)-N-methylamino, N-(2-dimethylaminoethyl)-N-metylamino, N-(3-aminopropyl)-N-methylamino, N-(3-methylaminopropyl)-N-methylamino, N-(3-ethylaminopropyl)-N-methylamino, N-(3-dimethylaminopropyl)-N-methylamino, N-(3-diethylaminopropyl)-N-methylamino, phenyl, benzyl, benzyloxy, 2-pyridylmethoxy, 2-(imidazol-1-yl)ethoxy, 3-(imidazol-1-yl)propoxy, pyrrolidin-1-yl, piperidino, morpholino, piperazin-1-yl, 4methylpiperazin-1-yl, 4-acetylpiperazin-1-yl pyrzolidin-1-ylmethyl, piperidinomethyl, morpholinomethyl, piperazin-1-ylmethyl, 4-methylpiperazin-1-ylmethyl, 4-acetylpiperazin-1-ylmethyl, piperidin-4-yloxy, 1-acetylpiperidin-4-yloxy, 2-(pyrrolidin-1-yl)ethoxy, 3-(pyrrolidin-1-yl)propoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy and 3-(4acetylpiperazin-1-yl)propoxy;
or a pharmaceutically-acceptable salt thereof.

3. An amide derivative of the Formula I according to claim 1 wherein $Q^1$ is substituted by a basic substituent selected from the substituents for $Q^1$ defined in claim 1.

4. An amide derivative of the Formula I according to claim 1
wherein $Q^1$ is substituted by a basic substituent selected from the substituents for $Q^1$ defined in claim 1 and $Q^2$ is a phenyl group which also bears a basic substituent selected from the substituents for $Q^2$ defined in claim 1.

5. An amide derivative of the Formula I according to claim 1
wherein
$R^3$ is methyl, ethyl, chloro or bromo;
$Q^1$ is 2-, 3- or 4-pyridyl which bears 1 basic substituent selected from amino, methylamino, ethylamino, dimethylamino, diethylamino, methylaminomethyl, ethylaminomethyl, dimethylaminomethyl, diethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-aminoethylamino, 3-aminopropylamino, 2-amino-2-methylpropylamino, 4-aminobutylamino, 3-methylaminopropylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-dimethylaminopropyl)-N-methylamino, 4-pyridyl, 2-pyridylmethyl, 2-pyridylmethoxy, pyrrolidin-1-yl, piperidino, morpholino, piperazin-1-yl, 4-methylpiperazin-1-yl, 4-ethylpiperazin-1-yl, 4-acetylpiperazin-1-yl, homopiperazin-1-yl, 4-methylhomopiperazin-1-yl, pyrrolidin-1-ylmethyl, piperidinomethyl, morpholinomethyl, piperazin-1-ylmethyl, 4-methylpiperazin-1-ylmethyl, 4-acetylpiperazin-1-ylmethyl, 4-(2-hydroxyethyl)piperazin-1-yl, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-(4-acetylpiperazin-1-yl)ethoxy, 3-(4-acetylpiperazin-1-yl)propoxy, 1-benzylpiperidin-4-ylamino, 2-pyrrolidin-1-ylethylamino, 3-pyrrolidin-1-ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino, 3-amino-2-hydroxypropoxy, 2-hydroxy-3-methylaminopropoxy, 3 dimethylamino-2-hydroxypropoxy, 3-amino-2-hydroxypropylamino, 2-hydroxy-3-methylaminopropylamino, 3-dimethylamino-2-hydroxypropylamino, 3-[N-(3-dimethylaminopropyl)-N-methylamino]-2-hydroxypropoxy, 2-hydroxy-3-pyrrolidin-1-ylpropoxy, 2-hydroxy-3-piperidinopropoxy, 2-hydroxy-3-morpholinopropoxy, 2-hydroxy-3-pyrrolidin-1-ylpropylamino, 2-hydroxy-3-piperidinopropylamino, 2-hydroxy-3-morpholinopropylamino, 3-[N-(3-dimethylaminopropyl)-N-methylamino]-2-hydroxypropylamino, 2-aminoethylaminomethyl, 3-aminopropylaminomethyl, 2-methylaminoethylaminomethyl, 3-methylaminopropylaminomethyl, 2-dimethylaminoethylaminomethyl, 3-dimethylaminopropylaminomethyl, 2-pyrrolidin-1-ylethylaminomethyl, 3-pyrrolidin-1-ylpropylaminomethyl, 2-piperidinoethylaminomethyl, 3-piperidinopropylaminomethyl, 2-morpholinoethylaminomethyl, 3-morpholinopropylaminomethyl, 2-piperazin-1-ylethylaminomethyl, 3-piperazin-1-ylpropylaminomethyl, 2-(4-methylpiperazin-1-yl)ethylaminomethyl and 3-(4-methylpiperazin-1-yl)propylaminomethyl, and wherein $Q^1$ may optionally bear 1 further substituent selected from hydroxy, fluoro, chloro, trifluoromethyl, cyano, methyl, ethyl, methoxy and ethoxy;

p is 0;

q is 0; and $Q^2$ is phenyl which optionally bears 1 or 2 substituents selected from hydroxy, fluoro, chloro, trifluoromethyl, cyano, amino, methyl, ethyl, methoxy, ethoxy, methylamino. dimethylamino, aminomethyl, methylaminomethyl, dimethylaminomethyl, 2-aminoethoxy, 3-aminopropoxy, 2-methylaminoethoxy, 3-methylaminopropoxy, 2-dimethylaminoethoxy, 3-dimethylaminopropoxy, 2-aminoethylamino, 3-aminopropylamino, 4-aminobutylamino, 3-methylaminopropylamino, 2-dimethylaminoethylamino, 3-dimethylaminopropylamino, 4-dimethylaminobutylamino, N-(2-dimethylaminoethyl)-N-methylamino, N-(3-dimethylaminopropyl)-N-methylamino, 4-pyridyl, 2-pyridylmethoxy, pyrrolidin-1-yl, morpholino, piperidino, piperazin-1-yl, 4-methylpiperazin-1-yl, 4-ethylpiperazin-1-yl, 4-acetylpiperazin-1-yl, homopiperazin-1-yl, 4-methylhomopiperazin-1-yl, pyrrolidin-1-ylmethyl, piperidinomethyl, morpholinomethyl, piperazin-1-ylmethyl, 4-ethylpiperazin-1-ylmethyl, 2-pyrrolidin-1-ylethoxy, 3 -pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)
ethoxy, 3-(4-methylpiperazin-1-yl)propoxy,
2-pyrrolidin-1-ylethylamino, 3-pyrrolidin
1-ylpropylamino, 2-morpholinoethylamino,
3-morpholinopropylamino, 2-piperidinoethylamino,
3-piperidinopropylamino, 2-piperazin-1-ylethylamino,
3-piperazin-1-ylpropylamino, 2-(4-methylpiperazin-1-
yl)ethylamino and 3-(4-methylpiperazin-1-yl)
propylamino;
or a pharmaceutically-acceptable salt thereof.

6. An amide derivative of the Formula I according to claim 1
wherein
$R^3$ is methyl or chloro;
$Q^1$ is 3-pyridyl or 4-pyridyl which bears a substituent selected from 2-aminoethylamino, 3-aminopropylamino, 2-amino-2-methylpropylamino, 4-aminobutylamino, 3-methylaminopropylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, 4-methylhomopiperazin-1-yl, 1-benzylpiperidin-4-ylamino, 2-pyrrolidin-1-ylethylamino, 3-pyrrolidin-ylpropylamino, -morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino or 3-amino-2-hydroxypropylamino;
p is 0;
q is 0; and
$Q^2$ is phenyl which bears a substituent selected from pyrrolidin-1-yl, morpholino and piperidino;
or a pharmaceutically-acceptable salt thereof.

7. An amide derivative of the Formula I according to claim 1
wherein
$R^3$ is methyl or chloro;
$Q^1$ is 3-pyridyl or 4-pyridyl which bears a substituent selected from 2-aminoethylamino, 3-aminopropylamino, 2-amino-2-methylpropylamino, 4-aminobutylamino, 3-methylaminopropylamino, 2-dimethylaminoethylamino, 2-diethylaminoethylamino, 3-dimethylaminopropylamino, 4-dimethylaminobutylamino, N-(2-dimethylaminoethyl)-N-methylamino, N-(3-dimethylaminopropyl)-N-methylamino, pyrrolidin-1-yl, morpholino, piperidino, piperazin-1-yl, 4-methylpiperazin-1-yl, 4-ethylpiperazin-1-yl, 4-(2-hydroxyethyl)piperazin-1-yl, homopiperazin-1-yl, 4-methylhomopiperazin-1-yl, 1-benzylpiperidin-4-ylamino, 2-pyrrolidin-1-ylethylamino, 3-pyrrolidin-1-ylpropylamino, 2-morpholinoethylamino, 3-morpholinopropylamino, 2-piperidinoethylamino, 3-piperidinopropylamino, 2-piperazin-1-ylethylamino, 3-piperazin-1-ylpropylamino, 2-(4-methylpiperazin-1-yl)ethylamino, 3-(4-methylpiperazin-1-yl)propylamino, 2-(1-methylpyrrolidin-2-yl)ethylamino, 3-(1-methylpyrrolidin-2-yl)propylamino or 3-amino-2-hydroxypropylamino;
p is 0;
q is 0; and
Q2 is phenyl which bears a substituent selected from pyrrolidin-1-yl, morpholino and piperidino and which optionally bears a fuirther substituent selected from fluoro and trifluoromethyl; or a pharmaceutically-acceptable salt thereof.

8. An amide derivative of the Formula I according to claim 1 selected from:
6-(3-morpholinopropylamino)-N-[2-methyl-5-(3-fluoro-5-morpholinobenzamido)phenyl]-pyridine-3-carboxamide, and
6-(4-methylpiperazin-1-yl)-N-[2-methyl-5-(3-fluoro-5-morpholinobenzamido)phenyl]-pyridine-3-carboxamide;
or a pharmaceutically-acceptable salt thereof.

9. A process for the preparation of an amide derivative of the Formula I, or a pharmaceutically-acceptable salt or in-vivo-cleavable ester thereof, according to claim 1 which comprises
(a) reacting an aniline of the Formula II

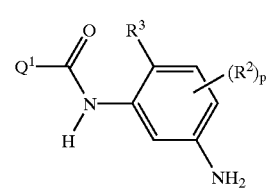

with an acid of the Formula III, or a reactive derivative thereof,

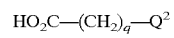

under standard amide bond forming conditions, wherein variable groups are as defined in claim 1 and wherein any functional group is protected if necessary, and:
(i) removing any protecting groups; and
(ii) optionally forming a pharmaceutically-acceptable salt or in-vivo-cleavable ester;
(b) reacting an acid of the Formula V, or an activated derivative thereof,

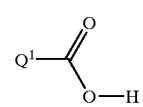

with an aniline of the Formula VII

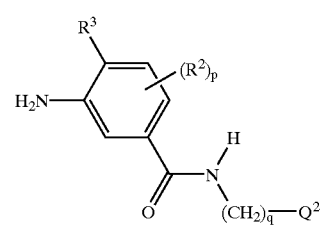

under standard amide bond forming conditions, wherein variable groups are as defined in claim 1 and wherein any functional group is protected, if necessary, and:
   (i) removing any protecting groups;
   (ii) optionally forming a pharmaceutically-acceptable salt or in-vivo-cleavable ester;
(c) for the preparation of a compound of the Formula I wherein a substituent on $Q^1$ or $Q^2$ is (1–6C)alkoxy or substituted (1–6C)alkoxy, (1–6C)alkylthio, (1–6C)alkylamino, di-[(1–6C)alkyl]amino or substituted (1–6C)alkylamino, the alkylation, conveniently in the presence of a suitable base, of an amide derivative of the Formula I wherein a substituent on $Q^1$ or $Q^2$ is hydroxy, mercapto or amino as appropriate;
(d) for the preparation of a compound of the Formula I wherein a substituent on $Q^1$ or $Q^2$ is (1–6C)alkanoylamino or substituted (2–6C)alkanoylamino, the acylation of a compound of the Formula I wherein a substituent on $Q^1$ or $Q^2$ is amino;
(e) for the preparation of a compound of the Formula I wherein a substituent on $Q^1$ or $Q^2$ is (1–6C)alkanesulphonylamino, the reaction of a compound of the Formula I wherein a substituent on $Q^1$ or $Q^2$ is amino with a (1–6C)alkanesulphonic acid, or an activated derivative thereof;
(f) for the preparation of a compound of the Formula I wherein a substituent on $Q^1$ or $Q^2$ is carboxy, carboxy-(1–6C)alkyl, carboxy-(1–6C)alkoxy, carboxy-(1–6C)alkylamino, N-(1–6C)alkyl-carboxy-(1–6C)alkylamino or carboxy-(2–6C)alkanoylamino, the cleavage of a compound of the Formula I wherein a substituent on $Q^1$ or $Q^2$ is (1–6C)alkoxycarbonyl, (1–6C)alkoxycarbonyl-(1–6C)alkyl, (1–6C)alkoxycarbonyl-(1–6C)alkoxy, (1–6C)alkoxycarbonyl-(1–6C)alkylamino, N-(1–6C)alkyl-(1–6C)alkoxycarbonyl-(1–6C)alkylamino or (1–6C)alkoxycarbonyl-(2–6C)alkanoylamino as appropriate; or
(g) for the preparation of a compound of the Formula I wherein a substituent on $Q^1$ or $Q^2$ is amino,(1–6C)alkylamino, di-[(1–6C)alkyl)]amino, substituted (1–6C)alkylamino, substituted N-(1–6C)alkyl-(1–6C)alkylamino or a N-linked heterocyclyl group, the reaction, conveniently in the presence of a suitable base, of an amide derivative of the Formula I wherein a substituent on $Q^1$ or $Q^2$ is a suitable leaving group with an appropriate amine or a N-containing heterocycle.

10. A pharmaceutical composition which comprises an amide derivative of the Formula I, or a pharmaceutically-acceptable or in-vivo-cleavable ester thereof, according to claim 1 in association with a pharmaceutically-acceptable diluent or carrier.

11. A method of treating a disease or medical condition mediated by a cytokine which comprises administering to a warm-blooded animal an effective amount of a compound of the Formula I, or a pharmaceutically-acceptable salt or in vivo cleavable ester thereof, according to claim 1.

* * * * *